(12) United States Patent
Blackley

(10) Patent No.: US 10,088,464 B2
(45) Date of Patent: *Oct. 2, 2018

(54) SYSTEMS AND METHODS FOR ANALYZING PHARMACEUTICALS

(71) Applicant: Lunatech, LLC, Studio City, CA (US)

(72) Inventor: Jonathan Seamus Blackley, South Pasadena, CA (US)

(73) Assignee: LunaTech, LLC, Encino, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 15/184,467

(22) Filed: Jun. 16, 2016

(65) Prior Publication Data

US 2016/0370340 A1 Dec. 22, 2016

Related U.S. Application Data

(60) Provisional application No. 62/180,507, filed on Jun. 16, 2015.

(51) Int. Cl.
*G01N 33/00* (2006.01)
*G01N 33/15* (2006.01)

(52) U.S. Cl.
CPC ......... *G01N 33/15* (2013.01); *G01N 33/0004* (2013.01)

(58) Field of Classification Search
CPC .......................... G01N 33/0004; G01N 33/15
See application file for complete search history.

(56) References Cited

U.S. PATENT DOCUMENTS

| | | | |
|---|---|---|---|
| 5,071,771 A * | 12/1991 | Barbour | G01N 27/622 250/282 |
| 5,363,842 A * | 11/1994 | Mishelevich | A61B 8/0875 128/200.14 |
| 5,457,316 A * | 10/1995 | Cohen | G01N 27/622 250/282 |
| 5,741,984 A * | 4/1998 | Danylewych-May | A61B 10/0096 73/864 |
| 5,781,289 A * | 7/1998 | Sabsabi | G01N 33/15 356/318 |
| 5,846,708 A * | 12/1998 | Hollis | B01J 19/0046 257/253 |

(Continued)

OTHER PUBLICATIONS

Dunn, Jamie D., et al. "Using a portable ion mobility spectrometer to screen dietary supplements for sibutramine." Journal of pharmaceutical and biomedical analysis 54.3 (2011): 469-474.*

(Continued)

*Primary Examiner* — Harshad R Patel
*Assistant Examiner* — Punam Roy
(74) *Attorney, Agent, or Firm* — Susan L. McCain; Hankin Patent Law, APC

(57) ABSTRACT

An apparatus is disclosed comprising an intake, configured to receive an emission from a pharmaceutical, a sensor, coupled to the intake, configured for detecting one or more constituents in the emission, a processor, configured for, collecting data from the sensor regarding the one or more constituents, and analyzing the data to determine an analysis result, and a display device, coupled to the vaporizer component, configured for displaying the analysis result.

18 Claims, 24 Drawing Sheets

(56) References Cited

U.S. PATENT DOCUMENTS

| | | | | |
|---|---|---|---|---|
| 5,937,852 | A * | 8/1999 | Butler | A61M 15/00 128/202.22 |
| 6,012,450 | A * | 1/2000 | Rubsamen | A61M 15/0045 128/200.14 |
| 6,297,499 | B1 * | 10/2001 | Fenn | H01J 49/167 250/288 |
| 6,351,983 | B1 * | 3/2002 | Haas | G01N 30/7206 250/281 |
| 6,513,524 | B1 * | 2/2003 | Storz | A61M 11/041 128/203.26 |
| 6,571,790 | B1 * | 6/2003 | Weinstein | A61F 17/00 128/200.14 |
| 6,772,756 | B2 * | 8/2004 | Shayan | A61M 11/041 128/202.21 |
| 6,830,046 | B2 * | 12/2004 | Blakley | A61M 15/0065 128/200.14 |
| 6,884,997 | B2 * | 4/2005 | Kashima | H01J 49/049 250/281 |
| 6,978,657 | B1 * | 12/2005 | Baumann | G01N 1/2214 73/28.04 |
| 7,002,145 | B2 * | 2/2006 | Ishikawa | G01N 1/2214 250/288 |
| 7,009,049 | B2 * | 3/2006 | Bergnes | C07D 239/90 544/253 |
| 7,343,779 | B1 * | 3/2008 | Yu | G01N 30/08 422/89 |
| 7,820,108 | B2 * | 10/2010 | Lampotang | A61B 5/00 422/83 |
| 7,972,865 | B2 * | 7/2011 | Yi | G01N 27/18 310/306 |
| 8,752,411 | B2 * | 6/2014 | Chiarugi | G01N 1/2226 73/19.1 |
| 8,757,147 | B2 | 6/2014 | Terry et al. | |
| 8,820,330 | B2 | 9/2014 | Bellinger | |
| 8,851,083 | B2 | 10/2014 | Oglesby et al. | |
| 8,955,522 | B1 | 2/2015 | Bowen et al. | |
| 9,048,076 | B2 * | 6/2015 | Stott | H01J 49/0459 |
| 9,121,755 | B2 * | 9/2015 | Izzia | G01J 3/0202 |
| 9,155,848 | B2 * | 10/2015 | Emarlou | A61M 11/041 |
| 9,408,416 | B2 | 8/2016 | Monsees et al. | |
| 9,498,002 | B1 | 11/2016 | Soreide | |
| 9,585,981 | B2 | 3/2017 | Wynalda, Jr. | |
| 2002/0124631 | A1 * | 9/2002 | Sunshine | G01N 33/0009 73/23.2 |
| 2004/0048853 | A1 * | 3/2004 | Bergnes | C07D 403/06 514/218 |
| 2005/0085740 | A1 * | 4/2005 | Davis | A61B 5/08 600/532 |
| 2007/0267031 | A1 * | 11/2007 | Hon | A24F 47/008 131/273 |
| 2010/0251802 | A1 * | 10/2010 | Patel | G01N 29/022 73/19.1 |
| 2013/0276799 | A1 * | 10/2013 | Davidson | A24F 47/004 131/273 |
| 2015/0313282 | A1 * | 11/2015 | Ademe | A24F 47/008 131/329 |
| 2016/0041076 | A1 * | 2/2016 | Chericoni | G01N 1/4044 436/501 |
| 2016/0157524 | A1 * | 6/2016 | Bowen | A24F 47/008 128/200.14 |
| 2017/0020195 | A1 * | 1/2017 | Cameron | A24F 47/008 |
| 2017/0074857 | A1 * | 3/2017 | Dennis | G01N 33/497 |

OTHER PUBLICATIONS

Chang, Michael J., et al. "Investigations on the direct introduction of cigarette smoke for trace elements analysis by inductively coupled plasma mass spectrometry." Spectrochimica Acta Part B: Atomic Spectroscopy58.11 (2003): 1979-1996.*

Schripp, Tobias, et al. "Does e-cigarette consumption cause passive vaping?." Indoor air 23.1 (2013): 25-31.*

Nowrangi, Derek S., Jiping Tang, and John H. Zhang. "Argon gas: a potential neuroprotectant and promising medical therapy." Medical gas research 4.1 (2014): 3.*

Haddi, Z., et al. "A portable electronic nose system for the identification of cannabis-based drugs." Sensors and Actuators B: Chemical 155.2 (2011): 456-463.*

* cited by examiner

SYSTEMS AND METHODS FOR ANALYZING
PHARMACEUTICALS

CROSS REFERENCE TO RELATED PATENT
APPLICATION

This application claims priority to U.S. Provisional Application No. 62/180,507 filed Jun. 16, 2015, here incorporated by reference in its entirety.

BACKGROUND

Manufacturing and dispensing of prescription medications is tightly controlled in some parts of the world, and not so tightly in other parts. But even where medications are tightly controlled, formulations may contain supposedly inert ingredients or trace amounts of contamination, that are either unknown to the manufacturer, or that the manufacturer is not required to report, or fails to report for any reason. These supposedly inert substances or trace elements may make a difference in compatibility or suitability for some sensitive individuals, for example, persons with particular allergies or metabolic anomalies. In addition, potency and other factors may vary from batch to batch, and with age depending on storage conditions and place of manufacture. It is also possible for counterfeit medications to enter the stream of commerce, and go undetected. Even medications bearing identical labels may have differences, and generic substitutes may differ from patented brands in ways that are important to particular patients. Accordingly, medications delivered to the patient may vary in important ways, even if labeled identically or similarly. Currently, however, such variations in formulation or current state are extremely expensive to discover using laboratory analysis, if discoverable at all. In addition, unlabeled medications may sometimes require identification, and there is often no reliable, economically feasible way to discover an identity of an unlabeled medication. Thus, pharmacists, doctors, and patients must rely on blind faith and trial and error, when it comes to differences between medication batches, and must either discard unlabeled medications or risk adverse effects.

It would be desirable, therefore, to develop new technologies for such applications, that overcomes these and other limitations of the prior art, and enables pharmacists, doctors and patients to discover more information about medications being consumed.

SUMMARY

It is to be understood that both the following general description and the following detailed description are exemplary and explanatory only and are not restrictive. In an aspect, an apparatus is disclosed comprising an intake, configured to receive an emission from a pharmaceutical, a sensor, coupled to the intake, configured for detecting one or more constituents in the emission, a processor, configured for, collecting data from the sensor regarding the one or more constituents, and analyzing the data to determine an analysis result, and a display device, coupled to the vaporizer component, configured for displaying the analysis result.

In an aspect, a method is disclosed comprising receiving an emission from a pharmaceutical, exposing the emission to a sensor, collecting data from the sensor regarding one or more constituents in the emission, analyzing the data to determine an analysis result, and displaying the analysis result.

Additional advantages will be set forth in part in the description which follows or can be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The features, nature, and advantages of the present disclosure will become more apparent from the detailed description set forth below when taken in conjunction with the drawings, in which like reference characters are used to identify like elements correspondingly throughout the specification and drawings.

DETAILED DESCRIPTION

Figure 1:
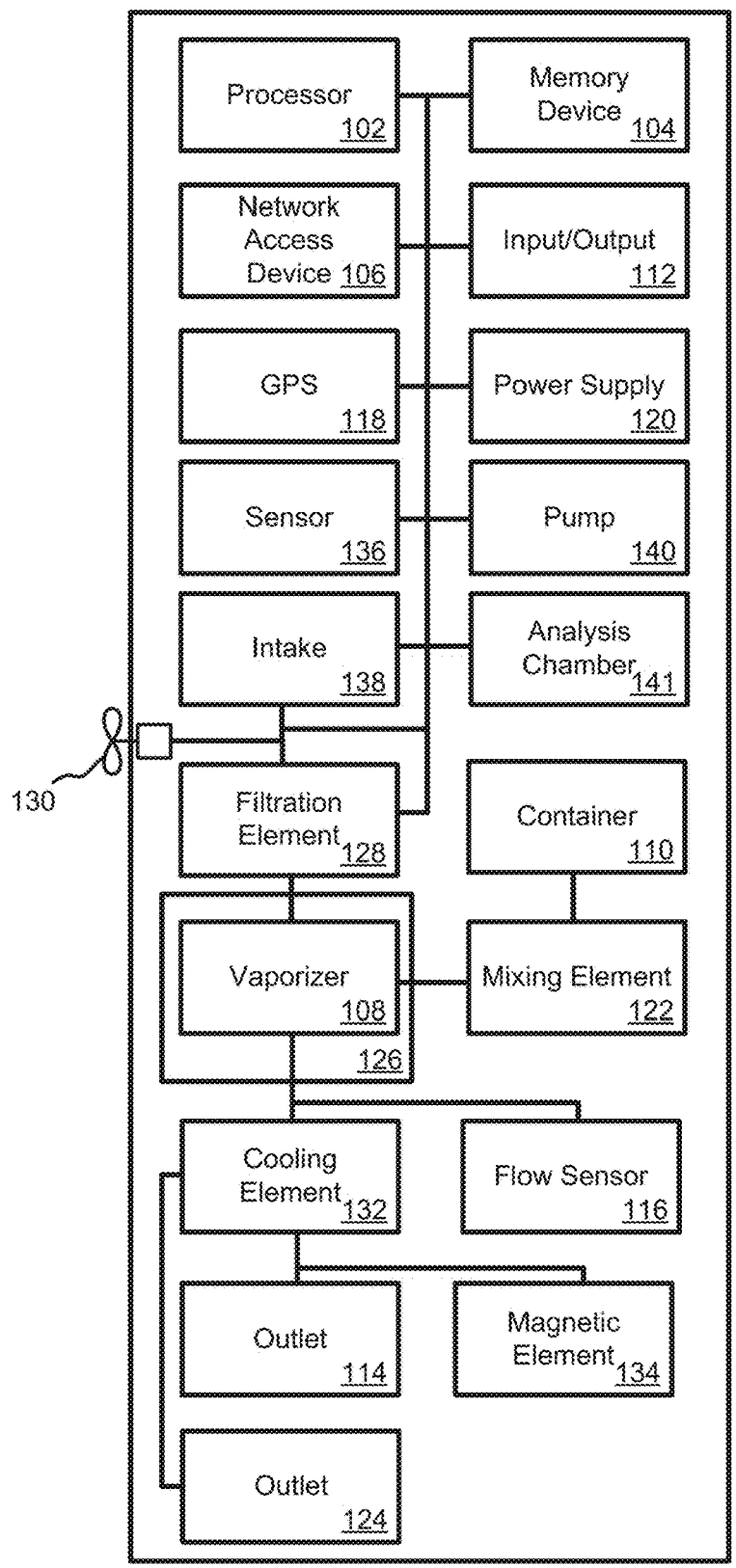
FIG. 1 illustrates a block diagram of an exemplary robotic vapor device.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges can be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium can be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions can be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Various aspects are now described with reference to the drawings. In the following description, for purposes of explanation, numerous specific details are set forth in order to provide a thorough understanding of one or more aspects. It can be evident, however, that the various aspects can be practiced without these specific details. In other instances, well-known structures and devices are shown in block diagram form in order to facilitate describing these aspects.

While embodiments of the disclosure are directed to vaporizing devices, it should be appreciated that aspects of the technology can be adapted by one of ordinary skill to nebulizing devices designed to produce an inhalable mist or aerosol.

The present disclosure relates to a system and method for testing prescription medication, and more specifically, to a system and method for characterizing a prescription medication according to its constituent compounds.

In an aspect of the disclosure, a pharmaceutical testing system that can determine the presence or concentration of active compounds or substances of concern in a sample of medication, and can provide a report. The pharmaceutical testing system may include a suction mechanism configured to draw an output from a sample conditioning chamber. The suction mechanism is in fluid communication with at least one of a chemical testing assembly, an exhaust port to ambient air, or a network communication device. The pharmaceutical testing apparatus may further include a processor operatively coupled to at least one of the suction mechanism, the chemical testing assembly, or the network communication device. Optionally, the suction mechanism may be configured to draw the air from the airspace through a personal vaporizer interposed between a suction inlet and the airspace. In other words, a commonplace personal vaporizer, of which high-quality models may currently be had for a few hundred dollars, may serve as a sample conditioning chamber in which an unidentified or uncharacterized prescription medication may be placed and heated, and from which useful information may be derived. Other, more versatile equipment for conditioning samples may also be used, for obtaining additional or more accurate data.

The processor may be further configured to receive measurement data from the chemical testing assembly. The chemical testing assembly may include at least one of a gas sensor circuit, or a GC/MS assembly.

The processor may be configured to perform at least one of analyzing the measurement data, sending the measurement data to a network node, or receiving an analysis of the measurement data from the network node. Accordingly, the pharmaceutical testing apparatus may further include a user interface port, wherein the processor is configured to determine a material to be measured based on an input from the user interface port. The user interface port may be configured to couple to at least one of a vaporizer or a mobile computing device. The processor may be configured to activate a gas or vapor sensor circuit based on the material to be measured.

In an aspect, the suction mechanism further comprises at least one of a variable stroke piston, variable stroke bellows, or a gas pump. The mechanism may further be configured to draw air or vapor at a variable rate. For example, the suction mechanism may be configured to draw air into an interior volume at a rate controlled at least in part by the processor.

In addition, the processor may be configured to identify the constituent compounds and the relative quantities of each within a prescription medication. For instance, the processor may be operatively coupled to a testing assembly configured to collect a product comprising at least one of smoke, vapor, or offgas from a prescription medication, which as noted above, may be heated in a vaporizer or sample conditioning chamber. The processor may be configured to analyze the collected product. Moreover, multiple prescription medications may be compounded together. As such, the processor may be configured to identify the constituent prescription medications of the compounded prescription medication.

The analyzing may include evaluating, classifying, comparing, validating, refuting a prior classification of, and/or cataloging the prescription medication. The processor may be operatively coupled to a remote processor by a network, to databases, to user display devices, and the like. In various embodiments, the processor may perform analyzing that includes transmitting by the processor data to a remote processor for at least one of analyzing, classifying, comparing, validating, refuting a prior classification of, and cataloging the prescription medication. In various embodiments, the analyzing may include determining analysis data, the data including at least one of mass spectrometry, PH testing, genetic testing, particle and cellular testing, synthetic molecular analysis, sensor based testing, diagnostic testing, and wellness testing.

The processor may be configured to perform various operations. For instance, the processor may be configured to determine whether the prescription medication is known or unknown, or may identify one or more prescription medication, or may evaluate the purity of the prescription medication, or determine impurity levels and identify impurities, or determine whether proper molecular elements of the prescription medication are in balanced or unbalanced molecular form, and/or the like.

For instance, the processor may work with the testing assembly to produce analysis data as the result of analysis. The analysis may include comparing characteristics of a product to a matching database of known characteristics of known prescription medications and match the product to a known prescription medication no that the analysis data is the characteristic comparison. The analysis may include comparing characteristics of the product to a matching database of known characteristics of known prescription medications and determining at least a first difference between the product and at least one known prescription medication so that the analysis data is the first difference. The analysis data may comprise an identification of the identity of a prescription medication and a validation of the composition of a prescription medication. The analysis data may include a determination of a molecular structure of a prescription medication. The device may include an instant matching database of known characteristics of known prescription medications and the molecular structure of a prescription medication may be determined by comparing the characteristics of the prescription medication to the instant matching database of known characteristics of known prescription medications. In further embodiments, the matching database may be a remote database operatively coupled to the processor by a network. The analysis may include determining a purity of the prescription medication. The analysis may include determining an identity of a first impurity of the prescription medication. The first impurity may be lead, feces, fillers, cellulose, pathogens, placebo ingredients, sugars, and/or proper molecular elements of the prescription medication but in unbalanced molecular form.

The processor may intemperate with a user interface device that may be configured to display in response to the data various indicators. For instance, the processor may direct the user interface device to display in response to the data at least one of lighted signal lights, gauges boxes, forms, check marks, avatars, visual images, graphic designs, lists, active calibrations or calculations, 2D interactive fractal designs, 3D fractal designs, 2D representations of a vapor device, 3D representations of a vapor devices and/or the like.

In various embodiments, the processor may communicate with a remote authorized system user interface device. The remote authorized system user interface device may be operatively coupled to the processor by a network, wherein the data is displayed by the remote authorized system user interface device. In further embodiments, a user interface display may be operatively coupled to the processor whereby the data is displayed. In further embodiments, the data may be displayed by both a remote authorized system user interface device and a user interface device.

The processor may interoperate with a chemical testing assembly to perform various methods. For instance, A method for analyzing prescription medication may include receiving, by a chemical testing assembly, at least one of smoke, vapor, fluid, solid, or offgas from a prescription medication into the chemical testing assembly, analyzing, by an analysis module of a processor operatively coupled to the chemical testing assembly, the prescription medication, and transmitting, by a communications module of the processor, data characterizing the prescription medication, in response to the analyzing.

The analyzing may further include determining the quantity of a an impurity in the at least one of smoke, vapor, extracted fluid or offgas. Impurities may include, for example, formaldehyde or other preservatives, trace metals such as antimony or arsenic, plastics or plastic modifiers, insect parts or animal dander, and numerous other things.

The analyzing may include comparing the quantity of the detected impurity to a stored impurity threshold for the material under test. The method may also include indicating, by at least one of an user interface device and a remote authorized system user device, a user-readable warning in response to the quantity of the detected impurity exceeding the stored impurity threshold.

The method may further include decarboxylating at least a portion of the prescription medication by the chemical testing assembly, wherein the receiving is in response to the decarboxylating.

FIG. 1 is a block diagram of an exemplary electronic robotic vapor device 100 as described herein. The electronic robotic vapor device 100 can be, for example, an e-cigarette, an e-cigar, an electronic vapor device, a hybrid electronic communication handset coupled/integrated vapor device, a robotic vapor device, a modified vapor device "mod," a micro-sized electronic vapor device, and the like. The robotic vapor device 100 can comprise any suitable housing for enclosing and protecting the various components disclosed herein. The robotic vapor device 100 can comprise a processor 102. The processor 102 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 can be coupled (e.g., communicatively, operatively, etc. . . . ) to auxiliary devices or modules of the robotic vapor device 100 using a bus or other coupling. The robotic vapor device 100 can comprise a power supply 120. The power supply 120 can comprise one or more batteries and/or other power storage device (e.g., capacitor) and/or a port for connecting to an external power supply. For example, an external power supply can supply power to the robotic vapor device 100 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like.

The robotic vapor device 100 can comprise a memory device 104 coupled to the processor 102. The memory device 104 can comprise a random access memory (RAM) configured for storing program instructions and data for execution or processing by the processor 102 during control of the robotic vapor device 100. When the robotic vapor device 100 is powered off or in an inactive state, program instructions and data can be stored in a long-term memory, for example, a non-volatile magnetic optical, or electronic memory storage device (not shown). Either or both of the RAM or the long-term memory can comprise a non-transitory computer-readable medium storing program instructions that, when executed by the processor 102, cause the robotic vapor device 100 to perform all or part of one or more methods and/or operations described herein. Program instructions can be written in any suitable high-level language, for example, C, C++, C# or the Java™, and compiled to produce machine-language code for execution by the processor 102. In an aspect, the memory device 104 can store one or more chemical signatures corresponding to one or more materials. FIG. 21-FIG. 24 illustrates chemical signatures 2100, 2200, 2300, and 2400 obtained via mass spectrometry for example pharmaceuticals. Other physico-chemical properties of pharmaceuticals can be used for chemical signatures.

Table 1

In an aspect, the robotic vapor device 100 can comprise a network access device 106 allowing the robotic vapor device 100 to be coupled to one or more ancillary devices (not shown) such as via an access point (not shown) of a wireless telephone network, local area network, or other coupling to a wide area network, for example, the Internet. In that regard, the processor 102 can be configured to share data with the one or more ancillary devices via the network access device 106. The shared data can comprise, for example, usage data and/or operational data of the robotic vapor device 100, a status of the robotic vapor device 100, a status and/or operating condition of one or more the components of the robotic vapor device 100, text to be used in a message, a product order, payment information, and/or any other data. Similarly, the processor 102 can be configured to receive control instructions from the one or more ancillary devices via the network access device 106. For example, a configuration of the robotic vapor device 100, an operation of the robotic vapor device 100, and/or other settings of the robotic vapor device 100, can be controlled by the one or more ancillary devices via the network access device 106. For example, an ancillary device can comprise a server that can provide various services and another ancillary device can comprise a smartphone for controlling operation of the robotic vapor device 100. In some aspects, the smartphone or another ancillary device can be used as a primary input/output of the robotic vapor device 100 such that data is received by the robotic vapor device 100 from the server, transmitted to the smartphone, and output on a display of the smartphone. In an aspect, data transmitted to the ancillary device can comprise a mixture of vaporizable material and/or instructions to release vapor. For example, the robotic vapor device 100 can be configured to determine a need for the release of vapor into the atmosphere. The robotic vapor device 100 can provide instructions via the network access device 106 to an ancillary device (e.g., another vapor device) to release vapor into the atmosphere.

In an aspect, the robotic vapor device 100 can also comprise an input/output device 112 coupled to one or more of the processor 102, the vaporizer 108, the network access device 106, and/or any other electronic component of the robotic vapor device 100. Input can be received from a user or another device and/or output can be provided to a user or another device via the input/output device 112. The input/output device 112 can comprise any combinations of input and/or output devices such as buttons, knobs, keyboards, touchscreens, displays, light-emitting elements, a speaker, and/or the like. In an aspect, the input/output device 112 can comprise an interface port (not shown) such as a wired interface, for example a serial port, a Universal Serial Bus (USB) port, an Ethernet port, or other suitable wired connection. The input/output device 112 can comprise a wireless interface (not shown), for example a transceiver using any suitable wireless protocol, for example Win (IEEE 802.11), Bluetooth®, infrared, or other wireless standard. For example, the input/output device 112 can communicate with a smartphone via Bluetooth® such that the inputs and outputs of the smartphone can be used by the user to interface with the robotic vapor device 100. In an aspect, the input/output device 112 can comprise a user interface. The user interface user interface can comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an aspect, the input/output device 112 can be coupled to an adaptor device to receive power and/or send/receive data signals from an electronic device. For example, the input/output device 112 can be configured to receive power from the adaptor device and provide the power to the power supply 120 to recharge one or more batteries. The input/output device 112 can exchange data signals received from the adaptor device with the processor 102 to cause the processor to execute one or more functions.

In an aspect, the input/output device 112 can comprise a touchscreen interface and/or a biometric interface. For example, the input/output device 112 can include controls that allow the user to interact with and input information and commands to the robotic vapor device 100. For example, with respect to the embodiments described herein, the input/output device 112 can comprise a touch screen display. The input/output device 112 can be configured to provide the content of the exemplary screen shots shown herein, which are presented to the user via the functionality of a display. User inputs to the touch screen display are processed by, for example, the input/output device 112 and/or the processor 102. The input/output device 112 can also be configured to process new content and communications to the system 100. The touch screen display can provide controls and menu selections, and process commands and requests. Application and content objects can be provided by the touch screen display. The input/output device 112 and/or the processor 102 can receive and interpret commands and other inputs, interface with the other components of the robotic vapor device 100 as required. In an aspect, the touch screen display can enable a user to lock, unlock, or partially unlock or lock, the robotic vapor device 100. The robotic vapor device 100 can be transitioned from an idle and locked state into an open state by, for example, moving or dragging an icon on the screen of the robotic vapor device 100, entering in a password/passcode, and the like. The input/output device 112 can thus display information to a user such as a puff count, an amount of vaporizable material remaining in the container 110, battery remaining, signal strength, combinations thereof, and the like.

In an aspect, the input/output device 112 can comprise an audio user interface. A microphone can be configured to receive audio signals and relay the audio signals to the input/output device 112. The audio user interface can be any interface that is responsive to voice or other audio commands. The audio user interface can be configured to cause an action, activate a function, etc, by the robotic vapor device 100 (or another device) based on a received voice (or other audio) command. The audio user interface can be deployed directly on the robotic vapor device 100 and/or via other electronic devices (e.g., electronic communication devices such as a smartphone, a smart watch, a tablet, a laptop, a dedicated audio user interface device, and the like). The audio user interface can be used to control the functionality of the robotic vapor device 100. Such functionality can comprise, but is not limited to, custom mixing of vaporizable material (e.g., eLiquids) and/or ordering custom made eLiquid combinations via an eCommerce service (e.g., specifications of a user's custom flavor mix can be transmitted to an eCommerce service, so that an eLiquid provider can mix a custom eLiquid cartridge for the user). The user can then reorder the custom flavor mix anytime or even send it to friends as a present, all via the audio user interface. The user can also send via voice command a mixing recipe to other users. The other users can utilize the mixing recipe (e.g., via an electronic vapor device having multiple chambers for eLiquid) to sample the same mix via an auto-order to the other users' devices to create the received mixing recipe. A custom mix can be given a title by a user and/or can be defined by parts (e.g., one part liquid A and two parts liquid B). The audio user interface can also be utilized to create and send a custom message to other users, to join eVapor clubs, to receive eVapor chart information, and to conduct a wide range of social networking, location services and eCommerce activities. The audio user interface can be secured via a password (e.g., audio password) which features at least one of tone recognition, other voice quality recognition and, in one aspect, can utilize at least one special cadence as part of the audio password.

The input/output device 112 can be configured to interface with other devices, for example, exercise equipment, computing equipment, communications devices and/or other vapor devices, for example, via a physical or wireless connection. The input/output device 112 can thus exchange data with the other equipment. A user may sync their robotic vapor device 100 to other devices, via programming attributes such as mutual dynamic link library (DLL) 'hooks'. This enables a smooth exchange of data between devices, as can a web interface between devices. The input/output device 112 can be used to upload one or more profiles to the other devices. Using exercise equipment as an example, the one or more profiles can comprise data such as workout routine data (e.g., timing, distance, settings, heart rate, etc. . . . ) and vaping data (e.g., eLiquid mixture recipes, supplements, vaping timing, etc. . . . ). Data from usage of previous exercise sessions can be archived and shared with new electronic vapor devices and/or new exercise equipment so that history and preferences may remain continuous and provide for simplified device settings, default settings, and recommended settings based upon the synthesis of current and archival data.

In an aspect, the robotic vapor device 100 can comprise a vaporizer 108. The vaporizer 108 can be coupled to one or more containers 110. Each of the one or more containers 110 can be configured to hold one or more vaporizable or non-vaporizable materials. The vaporizer 108 can receive the one or more vaporizable or non-vaporizable materials from the one or more containers 110 and heat the one or more vaporizable or non-vaporizable materials until the one or more vaporizable or non-vaporizable materials achieve a vapor state. In various embodiments, instead of heating the one or more vaporizable or non-vaporizable materials, the vaporizer 108 can nebulize or otherwise cause the one or more vaporizable or non-vaporizable materials in the one or more containers 110 to reduce in size into particulates. In various embodiments, the one or more containers 110 can comprise a compressed liquid that can be released to the vaporizer 108 via a valve or another mechanism. In various embodiments, the one or more containers 110 can comprise a wick (not shown) through which the one or more vaporizable or non-vaporizable materials is drawn to the vaporizer 108. The one or more containers 110 can be made of any suitable structural material, such as, an organic polymer, metal, ceramic, composite, or glass material. In an aspect, the vaporizable material can comprise one or more of a Propylene Glycol (PG) based liquid, a Vegetable Glycerin (VG) based liquid, a water based liquid, combinations thereof, and the like. In an aspect, the vaporizable material can comprise Tetrahydrocannabinol (THC), Cannabidiol (CBD), cannabinol (CBN), combinations thereof, and the like. In a further aspect, the vaporizable material can comprise an extract from *duboisia hopwoodii*.

In an aspect, the robotic vapor device 100 can comprise a mixing element 122. The mixing element 122 can be coupled to the processor 102 to receive one or more control signals. The one or more control signals can instruct the mixing element 122 to withdraw specific amounts of fluid from the one or more containers 110. The mixing element can, in response to a control signal from the processor 102, withdraw select quantities of vaporizable material in order to create a customized mixture of different types of vaporizable material. The liquid withdrawn by the mixing element 122 can be provided to the vaporizer 108.

The robotic vapor device 100 may include a plurality of valves, wherein a respective one of the valves is interposed between the vaporizer 108 and a corresponding one of outlet 114 and/or outlet 124 (e.g., one or more inlets of flexible tubes). Each of the valves may control a flow rate through a respective one of the flexible tubes. For example, each of the plurality of valves may include a lumen of adjustable effective diameter for controlling a rate of vapor flow there through. The assembly may include an actuator, for example a motor, configured to independently adjust respective ones of the valves under control of the processor. The actuator may include a handle or the like to permit manual valve adjustment by the user. The motor or actuator can be coupled to a uniform flange or rotating spindle coupled to the valves and configured for controlling the flow of vapor through each of the valves. Each of the valves can be adjusted so that each of the flexible tubes accommodate the same (equal) rate of vapor flow, or different rates of flow. The processor 102 can be configured to determine settings for the respective ones of the valves each based on at least one of: a selected user preference or an amount of suction applied to a corresponding one of the flexible tubes. A user preference can be determined by the processor 102 based on a user input, which can be electrical or mechanical. An electrical input can be provided, for example, by a touchscreen, keypad, switch, or potentiometer (e.g., the input/output 112). A mechanical input can be provided, for example, by applying suction to a mouthpiece of a tube, turning a valve handle, or moving a gate piece.

The robotic vapor device 100 may further include at least one light-emitting element positioned on or near each of the outlet 114 and/or the outlet 124 (e.g., flexible tubes) and configured to illuminate in response to suction applied to the outlet 114 and/or the outlet 124. At least one of an intensity of illumination or a pattern of alternating between an illuminated state and a non-illuminated state can be adjusted based on an amount of suction. One or more of the at least one light-emitting element, or another light-emitting element, may illuminate based on an amount of vaporizable material available. For example, at least one of an intensity of illumination or a pattern of alternating between an illuminated state and a non-illuminated state can be adjusted based on an amount of the vaporizable material within the robotic vapor device 100. In some aspects, the robotic vapor device 100 may include at least two light-emitting elements positioned on each of the outlet 114 and/or the outlet 124. Each of the at least two light-emitting elements may include a first light-emitting element and an outer light-emitting element positioned nearer the end of the outlet 114 and/or the outlet 124 than the first light-emitting element. Illumination of the at least two light-emitting elements may indicate a direction of a flow of vapor.

In an aspect, input from the input/output device 112 can be used by the processor 102 to cause the vaporizer 108 to vaporize the one or more vaporizable or non-vaporizable materials. For example, a user can depress a button, causing the vaporizer 108 to start vaporizing the one or more vaporizable or non-vaporizable materials. A user can then draw on an outlet 114 to inhale the vapor. In various aspects, the processor 102 can control vapor production and flow to the outlet 114 based on data detected by a flow sensor 116.

For example, as a user draws on the outlet 114, the flow sensor 116 can detect the resultant pressure and provide a signal to the processor 102. In response, the processor 102 can cause the vaporizer 108 to begin vaporizing the one or more vaporizable or non-vaporizable materials, terminate vaporizing the one or more vaporizable or non-vaporizable materials, and/or otherwise adjust a rate of vaporization of the one or more vaporizable or non-vaporizable materials. In another aspect, the vapor can exit the robotic vapor device 100 through an outlet 124. The outlet 124 differs from the outlet 114 in that the outlet 124 can be configured to distribute the vapor into the local atmosphere, rather than being inhaled by a user. In an aspect, vapor exiting the outlet 124 can be at least one of aromatic, medicinal, recreational, and/or wellness related. In an aspect, the robotic vapor device 100 can comprise any number of outlets. In an aspect, the outlet 114 and/or the outlet 124 can comprise at least one flexible tube. For example, a lumen of the at least one flexible tube can be in fluid communication with one or more components (e.g., a first container) of the robotic vapor device 100 to provide vapor to a user. In more detailed aspects, the at least one flexible tube may include at least two flexible tubes. Accordingly, the robotic vapor device 100 may further include a second container configured to receive a second vaporizable material such that a first flexible tube can receive vapor from the first vaporizable material and a second flexible tube receive vapor from the second vaporizable material. For example, the at least two flexible tubes can be in fluid communication with the first container and with second container. The robotic vapor device 100 may include an electrical or mechanical sensor configured to sense a pressure level, and therefore suction, in an interior of the flexible tube. Application of suction may activate the robotic vapor device 100 and cause vapor to flow.

In another aspect, the robotic vapor device 100 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid. In an aspect, the robotic vapor device 100 can be configured to permit a user to select between using a heating element of the vaporizer 108 or the piezoelectric dispersing element. In another aspect, the robotic vapor device 100 can be configured to permit a user to utilize both a heating element of the vaporizer 108 and the piezoelectric dispersing element.

In an aspect, the robotic vapor device 100 can comprise a heating casing 126. The heating casing 126 can enclose one or more of the container 110, the vaporizer 108, and/or the outlet 114. In a further aspect, the heating casing 126 can enclose one or more components that make up the container 110, the vaporizer 108, and/or the outlet 114. The heating casing 126 can be made of ceramic, metal, and/or porcelain. The heating casing 126 can have varying thickness. In an aspect, the heating casing 126 can be coupled to the power supply 120 to receive power to heat the heating casing 126. In another aspect, the heating casing 126 can be coupled to the vaporizer 108 to heat the heating casing 126. In another aspect, the heating casing 126 can serve an insulation role.

In an aspect, the robotic vapor device 100 can comprise a filtration element 128. The filtration element 128 can be configured to remove filter, purify, etc) contaminants from air entering the robotic vapor device 100. The filtration element 128 can optionally comprise a fan 130 to assist in delivering air to the filtration element 128. The robotic vapor device 100 can be configured to intake air into the filtration element 128, filter the air, and pass the filtered air to the vaporizer 108 for use in vaporizing the one or more vaporizable or non-vaporizable materials. In another aspect, the robotic vapor device 100 can be configured to intake air into the filtration element 128, filter the air, and bypass the vaporizer 108 by passing the filtered air directly to the outlet 114 for inhalation by a user.

In an aspect, the filtration element 128 can comprise cotton, polymer, wool, satin, meta materials and the like. The filtration element 128 can comprise a filter material that at least one airborne particle and/or undesired gas by a mechanical mechanism, an electrical mechanism, and/or a chemical mechanism. The filter material can comprise one or more pieces of a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals; etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 128 can comprise electrostatic plates, ultraviolet light, a HEPA filter, combinations thereof, and the like.

In an aspect, the robotic vapor device 100 can comprise a cooling element 132. The cooling element 132 can be configured to cool vapor exiting the vaporizer 108 prior to passing through the outlet 114. The cooling element 132 can cool vapor by utilizing air or space within the robotic vapor device 100. The air used by the cooling element 132 can be either static (existing in the robotic vapor device 100) or drawn into an intake and through the cooling element 132 and the robotic vapor device 100. The intake can comprise various pumping, pressure, fan, or other intake systems for drawing air into the cooling element 132. In an aspect, the cooling element 132 can reside separately or can be integrated the vaporizer 108. The cooling element 132 can be a single cooled electronic element within a tube or space and/or the cooling element 132 can be configured as a series of coils or as a grid like structure. The materials for the cooling element 132 can be metal, liquid, polymer, natural substance, synthetic substance, air, or any combination thereof. The cooling element 132 can be powered by the power supply 120, by a separate battery (not shown), or other power source (not shown) including the use of excess heat energy created by the vaporizer 108 being converted to energy used for cooling by virtue of a small turbine or pressure system to convert the energy. Heat differentials between the vaporizer 108 and the cooling element 132 can also be converted to energy utilizing commonly known geothermal energy principles.

In an aspect, the robotic vapor device 100 can comprise a magnetic element 134. For example, the magnetic element 134 can comprise an electromagnet, a ceramic magnet, a ferrite magnet, and/or the like. The magnetic element 134 can be configured to apply a magnetic field to air as it is brought into the robotic vapor device 100, in the vaporizer 108, and/or as vapor exits the outlet 114.

The input/output device 112 can be used to select whether vapor exiting the outlet 114 should be cooled or not cooled and/or heated or not heated and/or magnetized or not magnetized. For example, a user can use the input/output device 112 to selectively cool vapor at times and not cool vapor at other times. The user can use the input/output device 112 to selectively heat vapor at times and not heat vapor at other times. The user can use the input/output device 112 to selectively magnetize vapor at times and not magnetize vapor at other times. The user can further use the input/output device 112 to select a desired smoothness, temperature, and/or range of temperatures. The user can adjust the temperature of the vapor by selecting or clicking on a clickable setting on a part of the robotic vapor device 100. The user can use, for example, a graphical user interface (GUI) or a mechanical input enabled by virtue of clicking a rotational mechanism at either end of the robotic vapor device 100.

In an aspect, cooling control can be set within the robotic vapor device 100 settings via the processor 102 and system software (e.g., dynamic linked libraries). The memory 104 can store settings. Suggestions and remote settings can be communicated to and/or from the robotic vapor device 100 via the input/output device 112 and/or the network access device 106. Cooling of the vapor can be set and calibrated between heating and cooling mechanisms to what is deemed an ideal temperature by the manufacturer of the robotic vapor device 100 for the vaporizable material. For example, a temperature can be set such that resultant vapor delivers the coolest feeling to the average user but does not present any health risk to the user by virtue of the vapor being too cold, including the potential for rapid expansion of cooled vapor within the lungs and the damaging of tissue by vapor which has been cooled to a temperature which may cause frostbite like symptoms.

In another aspect, the fan 130 can comprise one or more fans. For example, the fan 130 can comprise a fan configured to expel air/vapor from the robotic vapor device 100 and a fan configured to intake air into the robotic vapor device 100. In an aspect, the robotic vapor device 100 can be configured to receive air, smoke, vapor or other material and analyze the contents of the air, smoke, vapor or other material using one or more sensors 136 in order to at least one of analyze, classify, compare, validate, refute, and/or catalogue the same. A result of the analysis can be, for example, an identification of at least one of medical, recreational, homeopathic, olfactory elements, spices, other cooking ingredients, ingredients analysis from food products, fuel analysis, pharmaceutical analysis, genetic modification testing analysis, dating, fossil and/or relic analysis and the like. The robotic vapor device 100 can pass utilize, for example, mass spectrometry, PH testing, genetic testing, particle and/or cellular testing, sensor based testing and other diagnostic and wellness testing either via locally available components or by transmitting data to a remote system for analysis.

In an aspect, a user can create a custom scent by using the robotic vapor device 100 to intake air elements, where the robotic vapor device 100 (or third-party networked device) analyzes the olfactory elements and/or biological elements within the sample and then formulates a replica scent within the robotic vapor device 100 (or third-party networked device) that can be accessed by the user instantly, at a later date, with the ability to purchase this custom scent from a networked e-commerce portal.

The robotic vapor device 100 can comprise an intake 138. The intake 138 can be receptacle for receiving air from an area surrounding the intake 138. In another aspect, the intake can be a receptacle for receiving at least a portion of a detachable vaporizer. In an aspect, the intake 138 can form an airtight seal with a detachable vaporizer. In another aspect, the intake 138 can form a non-airtight seal with a detachable vaporizer. The robotic vapor device 100 can comprise a pump 140 (or other similar suction mechanism) coupled to the intake 138. The pump 140 can be configured to draw air from an area surrounding the intake 138. In an aspect, one or more fan 130 can be configured to assist the pump 140 in drawing air into the robotic vapor device 100.

Air drawn in by the pump 140 through the intake 138 can be passed to an analysis chamber 141. The analysis chamber 141 can be a receptacle within the robotic vapor device 100 configured for holding the drawn air and for exposing the air to one or more sensors 136 in order to at least one of analyze, classify, compare, validate, refute, and/or catalogue the same. A result of the analysis can be, for example, a performance indicator for a detachable vaporizer (any measure indicative of whether a detachable vaporizer is performing as expected), an identification of at least one of medical, recreational, homeopathic, olfactory elements, spices, other cooking ingredients, ingredients analysis from food products, fuel analysis, pharmaceutical analysis, and the like.

In some embodiments, the analysis chamber 141 may surround or enclose a test bed such that the best bed may be a part of the structure of the analysis chamber 141. The robotic vapor device 100 can receive a sample (e.g., a material) into the analysis chamber 141 on the test bed. For example, a door in the housing of the robotic vapor device 100 can be opened, the sample placed in the analysis chamber 141 on the test bed, and the door closed. The sample can be any material, fluid, solid, gel, and/or vapor. In an aspect, the sample can comprise at least one of a biological tissue, one or more cells, a synthetic material, material from one or more bodily organs, a whole organism, a partial organism, or another carbon based or non-carbon based material. The robotic vapor device 100 can stress the sample by vaporizing or nebulizing a stressor material stored in the one or more containers 110 using the vaporizer 108 and applying the vaporized/nebulized stressor material to the sample in the test bed. The stressor can comprise at least one of a substance for changing a temperature of the sample, a diseased material, a fungus, a bacteria, a virus, another implementation of a disease or pathogen, a medication, a recreational substance, a wellness substance or particle, a substance for creating or adjusting a magnetic field, a substance generating light, a substance generating radiation, a carcinogen, air, and/or another stressor. Instead of or in addition to a stressor, the robotic vapor device 100 may be used to change a makeup of the sample. In that regard, an additive or other chemical or other compound may be used in place of the stressor. Where used herein, a stressor may apply to a stressor, an additive, or any other compound. The robotic vapor device 100 may also include another component (not shown) for applying one or more of these stressors, such as a laser, a magnet, an electrical circuit, a light bulb, a radiation generating device, or the like. The robotic vapor device 100 can vaporize or nebulize one or more stressor materials, apply the stressor material to a sample to be tested, and analyze the result of the test. In that regard, robotic vapor device 100 the mixing element 122 can mix one or more vaporized or nebulized (or vaporizable/nebulizable) stressor materials together prior to application to the sample. The robotic vapor device 100 can mechanically alter the sample (e.g., crush, cut, etc. . . . ). The robotic vapor device 100 can heat or cool the sample. The robotic vapor device 100 can manipulate the sample as disclosed for the purpose of causing an emission from the material (e.g., solid particles, smoke, vapor, fluid, or gas).

The robotic vapor device 100 can utilize, for example, mass spectrometry, gas chromatography, PH testing, particle and/or cellular testing, sensor based testing and other diagnostic and wellness testing either via locally available components or by transmitting data to a remote system for analysis. The mass spectrometry and/or gas chromatography systems disclosed herein can be implemented in a compact form factor, as is known in the art. Mass spectrometry is an analytical chemistry technique that identifies an amount and type of chemicals present in a sample by measuring the mass-to-charge ratio and abundance of gas-phase ions. A mass spectrum (plural spectra) is a plot of the ion signal as a function of the mass-to-charge ratio. The spectra are used to determine the elemental or isotopic signature of a sample, the masses of particles and of molecules, and to elucidate the chemical structures of molecules, such as peptides and other chemical compounds. Mass spectrometry works by ionizing chemical compounds to generate charged molecules or molecule fragments and measuring their mass-to-charge ratios.

In a typical mass spectrometry procedure, a sample of the drawn air, is ionized, for example by bombarding the air/vapor with electrons. This can cause some of the sample's molecules to break into charged fragments. These ions are then separated according to their mass-to-charge ratio, typically by accelerating them and subjecting them to an electric or magnetic field: ions of the same mass-to-charge ratio will undergo the same amount of deflection. The ions are detected by a mechanism capable of detecting charged particles, such as an electron multiplier. Results are displayed as spectra of the relative abundance of detected ions as a function of the mass-to-charge ratio. The atoms or molecules in the sample can be identified by correlating known masses to the identified masses stored on the memory device 104 or through a characteristic fragmentation pattern. Thus, a composition of the drawn air can be determined.

In another aspect, nanosensor technology using nanostructures: single walled carbon nanotubes (SWNTs), combined with a silicon-based microfabrication and micromachining process can be used. This technology provides a sensor array that can accommodate different nanostructures for specific applications with the advantages of high sensitivity, low power consumption, compactness, high yield and low cost. This platform provides an array of sensing elements for chemical detection. Each sensor in the array can comprise a nanostructure—chosen from many different categories of sensing material—and an interdigitated electrode (IDE) as a transducer. It is one type of electrochemical sensor that implies the transfer of charge from one electrode to another. This means that at least two electrodes constitute an electrochemical cell to form a closed electrical circuit. Due to the interaction between nanotube devices and gas molecules, the electron configuration is changed in the nanostructured sensing device, therefore, the changes in the electronic signal such as current or voltage were observed before and during the exposure of gas species (such as NO 2, NH 3, etc.). By measuring the conductivity change of the CNT device, the concentration of the chemical species, such as gas molecules in the air/vapor drawn from the robotic vapor device 100, can be measured.

In another aspect, the one or more sensors 136 can comprise one or more of a biochemical/chemical sensor, a thermal sensor, a radiation sensor, a mechanical sensor, an optical sensor, a mechanical sensor, a magnetic sensor, an electrical sensor, combinations thereof and the like. The biochemical/chemical sensor can be configured to detect one or more biochemical/chemicals causing a negative environmental condition such as, but not limited to, smoke, a vapor, a gas, a liquid, a solid, an odor, combinations thereof, and/or the like. The biochemical/chemical sensor can comprise one or more of a mass spectrometer, a conducting/nonconducting regions sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a solid electrolyte gas sensors, a piezoelectric quartz crystal sensor, and/or combinations thereof.

A semiconductor sensor can be configured to detect gases by a chemical reaction that takes place when the gas comes in direct contact with the sensor. Tin dioxide is the most common material used in semiconductor sensors, and the electrical resistance in the sensor is decreased when it comes in contact with the monitored gas. The resistance of the tin dioxide is typically around 50 k$\Omega$ in air but can drop to around 3.5 k$\Omega$ in the presence of 1% methane. This change in resistance is used to calculate the gas concentration. Semiconductor sensors can be commonly used to detect hydrogen, oxygen, alcohol vapor, and harmful gases such as carbon monoxide. A semiconductor sensors can be used as a carbon monoxide sensors. A semiconductor sensor can be used as a breathalyzer. Because the sensor must come in contact with the gas to detect it, semiconductor sensors work over a smaller distance than infrared point or ultrasonic detectors.

The thermal sensor can be configured to detect temperature, heat, heat flow, entropy, heat capacity, combinations thereof, and the like. Exemplary thermal sensors include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

The radiation sensor can be configured to detect gamma rays, X-rays, ultra-violet rays, visible, infrared, microwaves and radio waves. Exemplary radiation sensors include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors.

The optical sensor can be configured to detect visible, near infrared, and infrared waves. The mechanical sensor can be configured to detect displacement, velocity, acceleration, force, torque, pressure, mass, flow, acoustic wavelength, and amplitude. Exemplary mechanical sensors include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors. The magnetic sensor can be configured to detect magnetic field, flux, magnetic moment, magnetization, and magnetic permeability. The electrical sensor can be configured to detect charge, current, voltage, resistance, conductance, capacitance, inductance, dielectric permittivity, polarization and frequency.

Upon sensing a condition of the air/vapor in the analysis chamber 141, the one or more sensors 136 can provide data to the processor 102 to determine the nature of the condition and to generate/transmit one or more notifications based on the condition. The one or more notifications can be deployed to a detachable vaporizer, to a user's wireless device, a remote computing device, and/or synced accounts. For example, the network device access device 106 can be used to transmit the one or more notifications directly (e.g., via Bluetooth®) to a user's smartphone to provide information to the user. In another aspect, the network access device 106 can be used to transmit sensed information and/or the one or more alerts to a remote server for use in syncing one or more other devices used by the user (e.g., other vapor devices, other electronic devices (smartphones, tablets, laptops, etc. . . . ). In another aspect, the one or more alerts can be provided to the user of the robotic vapor device 100 via vibrations, audio, colors, and the like deployed from the mask, for example through the input/output device 112. The input/output device 112 can comprise one or more LED's of various colors to provide visual information to the user. In another example, the input/output device 112 can comprise one or more speakers that can provide audio information to the user. For example, various patterns of beeps, sounds, and/or voice recordings can be utilized to provide the audio information to the user. In another example, the input/output device 112 can comprise an LCD screen/touchscreen that provides a summary and/or detailed information regarding the condition and/or the one or more notifications.

In another aspect, upon sensing a condition, the one or more sensors 136 can provide data to the processor 102 to determine the nature of the condition and to provide a recommendation for mitigating the condition. Mitigating the conditions can comprise, for example, adjusting one or more operational parameters of a detachable vaporizer and/or the vaporizer 108 (e.g., temperature of vaporization, quantity of one or more vaporizable materials vaporized, etc. . . . ). The processor 102 can access a database stored in the memory device 104 to make such a determination or the network device 106 can be used to request information from a server to verify the sensor findings. In an aspect, the server can provide an analysis service to the robotic vapor device 100. For example, the server can analyze data sent by the robotic vapor device 100 based on a reading from the one or more sensors 136. The server can determine and transmit one or more recommendations to the robotic vapor device 100 to mitigate the sensed condition. The robotic vapor device 100 can use the one or more recommendations to transmit one or more commands to a detachable vaporizer and/or the vaporizer 108 to reconfigure operation of the vaporizer 108.

In an aspect, the processor 102 (or a remote computing device) can generate an analysis result based on data generated by the one or more sensors 136 and/or the processor 102. The analysis result can relate to a blood alcohol level, a blood sugar level, a carbon dioxide level, a volatile organic compound (VOC) level, a chemical signature for a disease, a methane level, a hydrogen level, combinations thereof, and the like. The analysis result can be displayed on a screen of the robotic vapor device 100. In another aspect, the analysis result can be displayed on a screen of an electronic device in communication with the robotic vapor device 100. For example, an electronic device can establish a communication session with the robotic vapor device 100 whereby data can be exchanged and the electronic device can provide a user interface that can control one or more functions of the robotic vapor device 100 and/or display data received from the robotic vapor device 100.

In an aspect, the analysis result can comprise a chemical signature for the sample. The processor 102 can comprise the chemical signature to a database of chemical signatures of known substances to determine a match and thereby identify the sample. In an aspect, the database can be stored in the memory device 104 and/or the database can be stored at a remote computing device. If the database is stored at a remote computing device, the processor 102 can utilize the network access device 106 to query the database at the remote computing device.

In an aspect, the robotic vapor device 100 can comprise a global positioning system (GPS) unit 118. The GPS 118 can detect a current location of the device 100. In some aspects, a user can request access to one or more services that rely on a current location of the user. For example, the processor 102 can receive location data from the GPS 118, convert it to usable data, and transmit the usable data to the one or more services via the network access device 106. GPS unit 118 can receive position information from a constellation of satellites operated by the U.S. Department of Defense. Alternately, the GPS unit 118 can be a GLONASS receiver operated by the Russian Federation Ministry of Defense, or any other positioning device capable of providing accurate location information (for example, LORAN, inertial navigation, and the like). The GPS unit 118 can contain additional logic, either software, hardware or both to receive the Wide Area Augmentation System (WAAS) signals, operated by the Federal Aviation Administration, to correct dithering errors and provide the most accurate location possible. Overall accuracy of the positioning equipment subsystem containing WAAS is generally in the two meter range.

Figure 2:
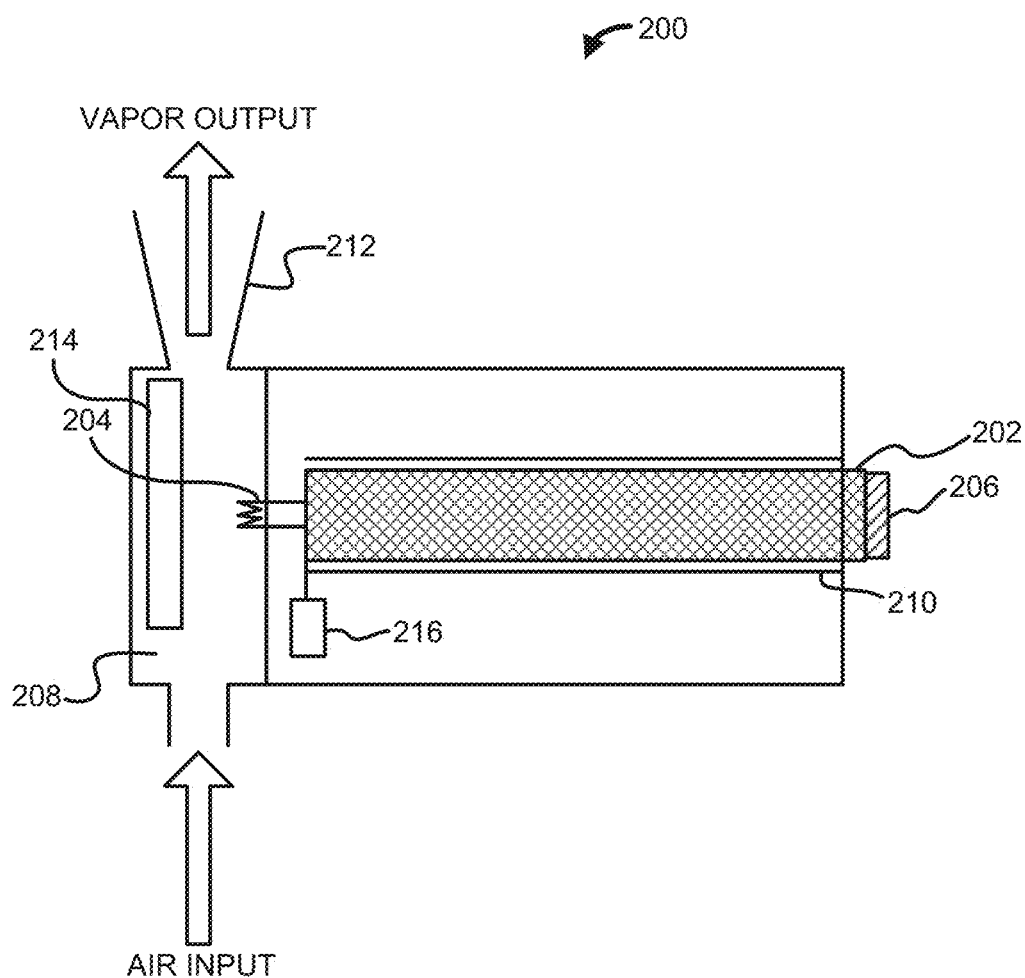
FIG. 2 illustrates an exemplary vaporizer.

FIG. 2 illustrates an exemplary vaporizer 200. The vaporizer 200 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vaporizer 200 can be used internally of the robotic vapor device 100 or can be a separate device. For example, the vaporizer 200 can be used in place of the vaporizer 108.

The vaporizer 200 can comprise or be coupled to one or more containers 202 containing a vaporizable material, for example a fluid. For example, coupling between the vaporizer 200 and the one or more containers 202 can be via a wick 204, via a valve, or by some other structure. Coupling can operate independently of gravity, such as by capillary action or pressure drop through a valve. The vaporizer 200 can be configured to vaporize the vaporizable material from the one or more containers 202 at controlled rates in response to mechanical input from a component of the robotic vapor device 100, and/or in response to control signals from the processor 102 or another component. Vaporizable material (e.g., fluid) can be supplied by one or more replaceable cartridges 206. In an aspect the vaporizable material can comprise aromatic elements. In an aspect, the aromatic elements can be medicinal, recreational, and/or wellness related. The aromatic element can include, but is not limited to, at least one of lavender or other floral aromatic eLiquids, mint, menthol, herbal soil or geologic, plant based, name brand perfumes, custom mixed perfume formulated inside the robotic vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), anew our a sexual nature (e.g., musk, pheromones, etc. . . . ). The one or more replaceable cartridges 206 can contain the vaporizable material. If the vaporizable material is liquid, the cartridge can comprise the wick 204 to aid in transporting the liquid to a mixing chamber 208. In the alternative, some other transport mode can be used. Each of the one or more replaceable cartridges 206 can be configured to fit inside and engage removably with a receptacle (such as the container 202 and/or a secondary container) of the robotic vapor device 100. In an alternative, or in addition, one or more fluid containers 210 can be fixed in the robotic vapor device 100 and configured to be refillable. In an aspect, one or more materials can be vaporized at a single time by the vaporizer 200. For example, some material can be vaporized and drawn through an exhaust port 212 and/or some material can be vaporized and exhausted via a smoke simulator outlet (not shown).

The mixing chamber 208 can also receive an amount of one or more compounds (e.g., vaporizable material) to be vaporized. For example, the processor 102 can determine a first amount of a first compound and determine a second amount of a second compound. The processor 102 can cause the withdrawal of the first amount of the first compound from a first container into the mixing chamber and the second amount of the second compound from a second container into the mixing chamber. The processor 102 can also determine a target dose of the first compound, determine a vaporization ratio of the first compound and the second compound based on the target dose, determine the first amount of the first compound based on the vaporization ratio, determine the second amount of the second compound based on the vaporization ratio, and cause the withdrawal of the first amount of the first compound into the mixing chamber, and the withdrawal of the second amount of the second compound into the mixing chamber.

The processor 102 can also determine a target dose of the first compound, determine a vaporization ratio of the first compound and the second compound based on the target dose, determine the first amount of the first compound based on the vaporization ratio, and determine the second amount of the second compound based on the vaporization ratio. After expelling the vapor through an exhaust port for inhalation by a user, the processor 102 can determine that a cumulative dose is approaching the target dose and reduce the vaporization ratio. In an aspect, one or more of the vaporization ratio, the target dose, and/or the cumulative dose can be determined remotely and transmitted to the robotic vapor device 100 for use.

In operation, a heating element 214 can vaporize or nebulize the vaporizable material in the mixing chamber 208, producing an inhalable vapor/mist that can be expelled via the exhaust port 212. In an aspect, the heating element 214 can comprise a heater coupled to the wick (or a heated wick) 204 operatively coupled to (for example, in fluid communication with) the mixing chamber 210. The heating element 214 can comprise a nickel-chromium wire or the like, with a temperature sensor (not shown) such as a thermistor or thermocouple. Within definable limits, by controlling power to the wick 204, a rate of vaporization can be independently controlled. A multiplexer 216 can receive power from any suitable source and exchange data signals with a processor, for example, the processor 102 of the robotic vapor device 100, for control of the vaporizer 200. At a minimum, control can be provided between no power (off state) and one or more powered states. Other control mechanisms can also be suitable.

In another aspect, the vaporizer 200 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In an aspect, the vaporizer 200 can be configured to permit a user to select between using the heating element 214 or the piezoelectric dispersing element. In another aspect, the vaporizer 200 can be configured to permit a user to utilize both the heating element 214 and the piezoelectric dispersing element.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid.

Figure 3:
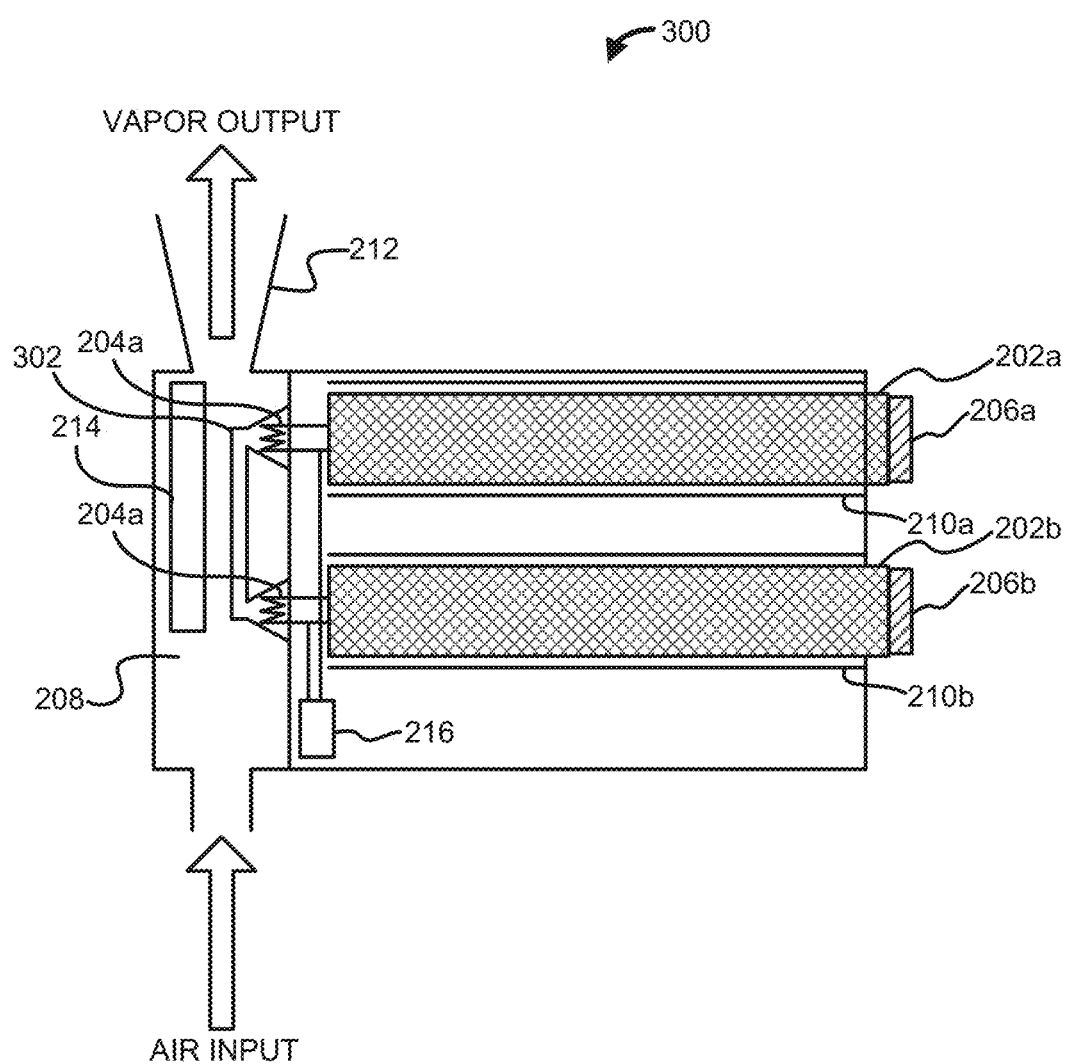
FIG. 3 illustrates an exemplary vaporizer configured for vaporizing a mixture of vaporizable material.

FIG. 3 illustrates a vaporizer 300 that comprises the elements of the vaporizer 200 with two containers 202a and 202b containing a vaporizable material, for example a fluid or a solid. In an aspect, the fluid can be the same fluid in both containers or the fluid can be different in each container. In an aspect the fluid can comprise aromatic elements. The aromatic element can include, but is not limited to, at least one of lavender or other floral aromatic eLiquids, mint, menthol, herbal soil or geologic, plant based, name brand perfumes, custom mixed perfume formulated inside the robotic vapor device 100 and aromas constructed to replicate the smell of different geographic places, conditions, and/or occurrences, for example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). Coupling between the vaporizer 200 and the container 202a and the container 202b can be via a wick 204a and a wick 204b, respectively, via a valve, or by some other structure. Coupling can operate independently of gravity, such as by capillary action or pressure drop through a valve. The vaporizer 300 can be configured to mix in varying proportions the fluids contained in the container 202a and the container 202b and vaporize the mixture at controlled rates in response to mechanical input from a component of the robotic vapor device 100, and/or in response to control signals from the processor 102 or another component. For example, based on a vaporization ratio. In an aspect, a mixing element 302 can be coupled to the container 202a and the container 202b. The mixing element can, in response to a control signal from the processor 102, withdraw select quantities of vaporizable material in order to create a customized mixture of different types of vaporizable material. Vaporizable material (e.g., fluid) can be supplied by one or more replaceable cartridges 206a and 206b. The one or more replaceable cartridges 206a and 206b can contain a vaporizable material. If the vaporizable material is liquid, the cartridge can comprise the wick 204a or 204b to aid in transporting the liquid to a mixing chamber 208. In the alternative, some other transport mode can be used. Each of the one or more replaceable cartridges 206a and 206b can be configured to fit inside and engage removably with a receptacle (such as the container 202a or the container 202b and/or a secondary container) of the robotic vapor device 100. In an alternative, or in addition, one or more fluid containers 210a and 210b can be fixed in the robotic vapor device 100 and configured to be refillable. In an aspect, one or more materials can be vaporized at a single time by the vaporizer 300. For example, some material can be vaporized and drawn through an exhaust port 212 and/or some material can be vaporized and exhausted via a smoke simulator outlet (not shown).

Figure 4:
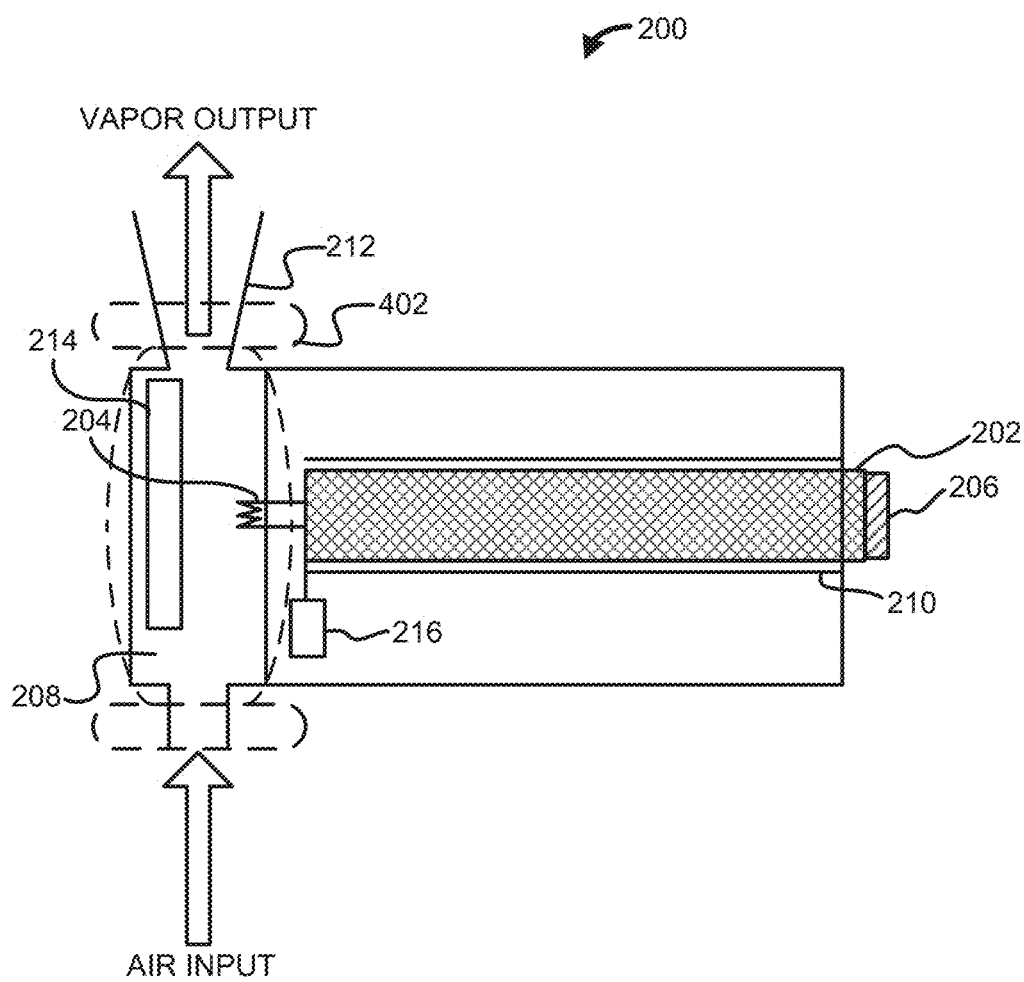
FIG. 4 illustrates an exemplary vaporizer device.

FIG. 4 illustrates a vaporizer 200 that comprises the elements of the vaporizer 200 with a heating casing 402. The heating casing 402 can enclose the heating element 214 or can be adjacent to the heating element 214. The heating casing 402 is illustrated with dashed lines, indicating components contained therein. The heating casing 402 can be made of ceramic, metal, and/or porcelain. The heating casing 402 can have varying thickness. In an aspect, the heating casing 402 can be coupled to the multiplexer 216 to receive power to heat the heating casing 402. In another aspect, the heating casing 402 can be coupled to the heating element 214 to heat the heating casing 402. In another aspect, the heating casing 402 can serve an insulation role.

Figure 5:
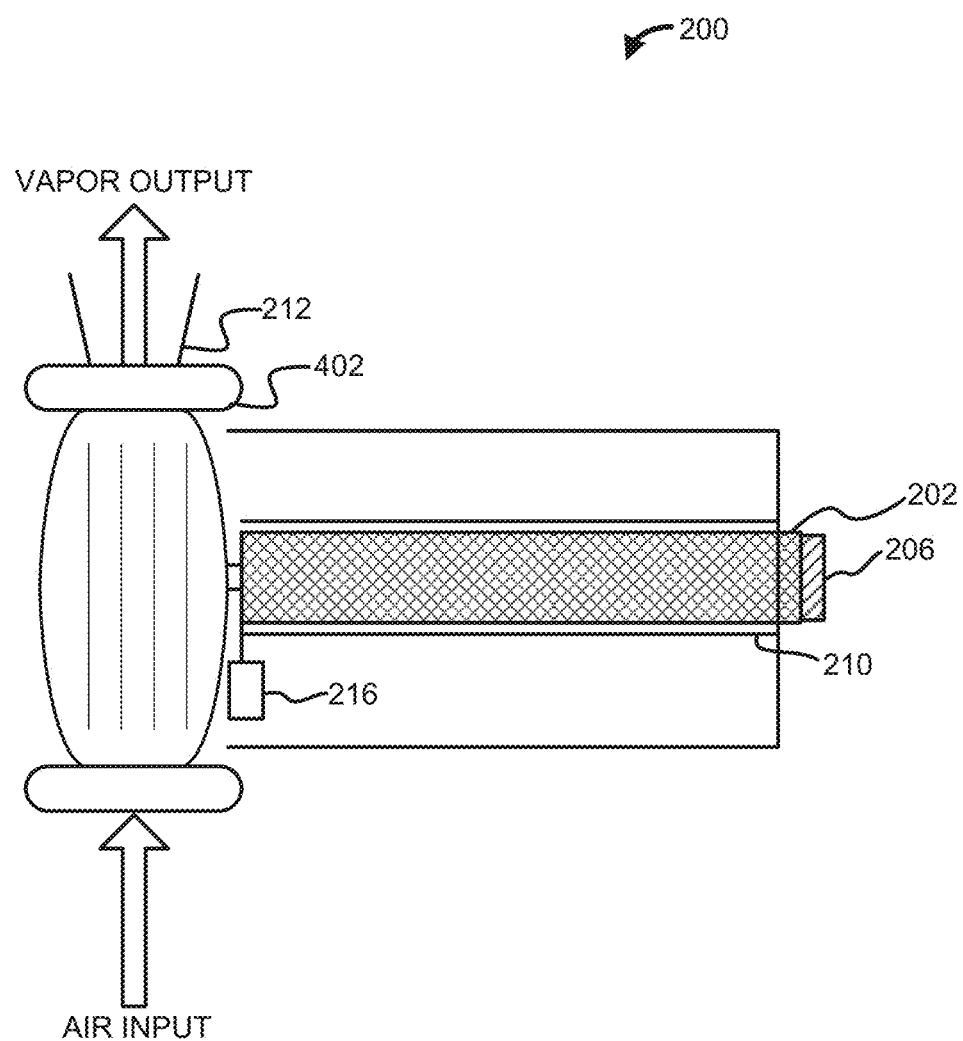
FIG. 5 illustrates another exemplary vaporizer.

FIG. 5 illustrates the vaporizer 200 of FIG. 2 and FIG. 4, but illustrates the heating casing 402 with solid lines, indicating components contained therein. Other placements of the heating casing 402 are contemplated. For example, the heating casing 402 can be placed after the heating element 214 and/or the mixing chamber 208.

Figure 6:
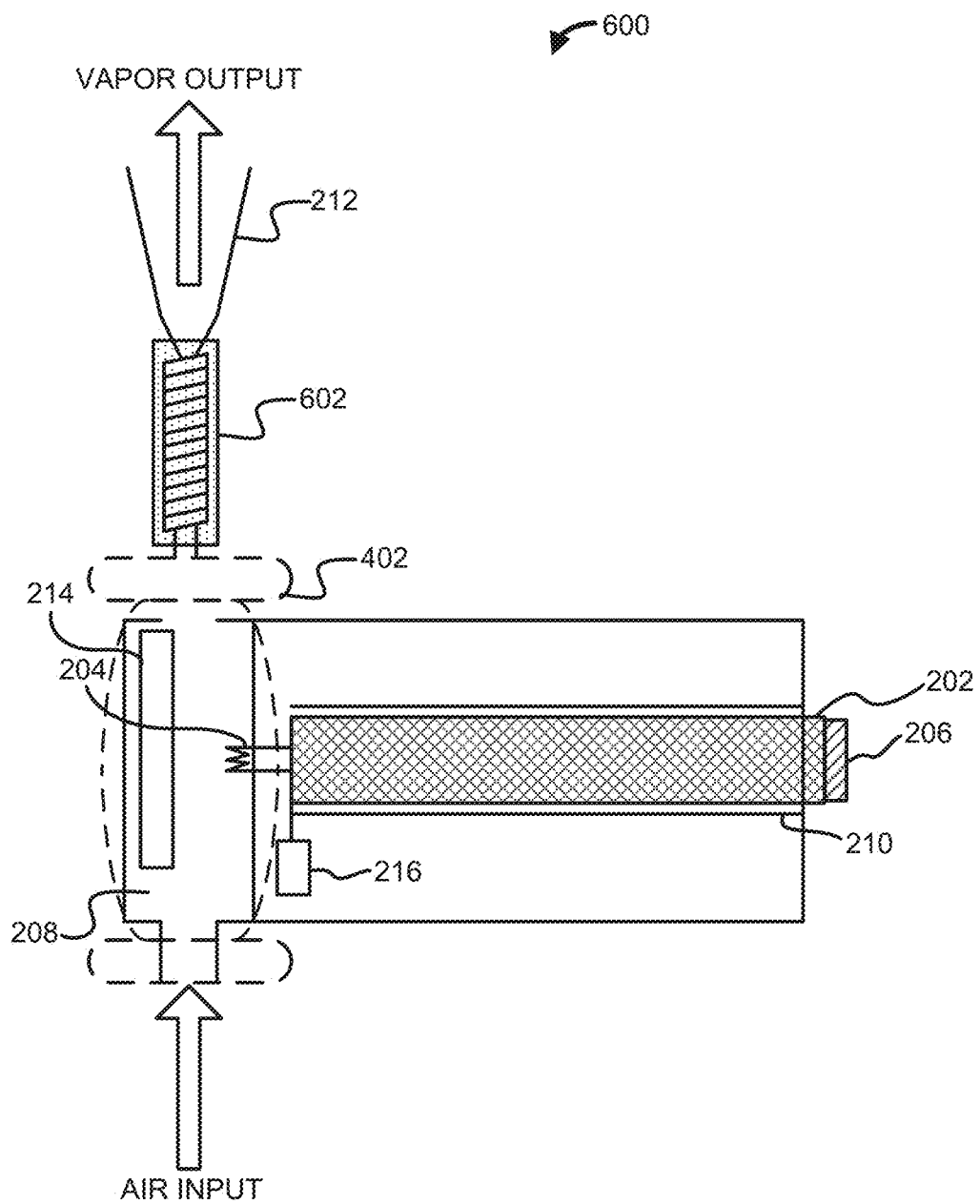
FIG. 6 illustrates another exemplary vaporizer.

FIG. 6 illustrates a vaporizer 600 that comprises the elements of the vaporizer 200 of FIG. 2 and FIG. 4, with the addition of a cooling element 602. The vaporizer 600 can optionally comprise the heating casing 402. The cooling element 602 can comprise one or more of a powered cooling element, a cooling air system, and/or or a cooling fluid system. The cooling element 602 can be self-powered, co-powered, or directly powered by a battery and/or charging system within the robotic vapor device 100 (e.g., the power supply 120). In an aspect, the cooling element 602 can comprise an electrically connected conductive coil, grating, and/or other design to efficiently distribute cooling to the at least one of the vaporized and/or non-vaporized air. For example, the cooling element 602 can be configured to cool air as it is brought into the vaporizer 600/mixing chamber 208 and/or to cool vapor after it exits the mixing chamber 208. The cooling element 602 can be deployed such that the cooling element 602 is surrounded by the heated casing 402 and/or the heating element 214. In another aspect, the heated casing 402 and/or the heating element 214 can be surrounded by the cooling element 602. The cooling element 602 can utilize at least one of cooled air, cooled liquid, and/or cooled matter.

In an aspect, the cooling element 602 can be a coil of any suitable length and can reside proximate to the inhalation point of the vapor (e.g., the exhaust port 212). The temperature of the air is reduced as it travels through the cooling element 602. In an aspect, the cooling element 602 can comprise any structure that accomplishes a cooling effect. For example, the cooling element 602 can be replaced with a screen with a mesh or grid-like structure, a conical structure, and/or a series of cooling airlocks, either stationary or opening, in a periscopic/telescopic manner. The cooling element 602 can be any shape and/or can take multiple forms capable of cooling heated air, which passes through its space.

In an aspect, the cooling element 602 can be any suitable cooling system for use in a vapor device. For example, a fan, a heat sink, a liquid cooling system, a chemical cooling system, combinations thereof, and the like. In an aspect, the cooling element 602 can comprise a liquid cooling system whereby a fluid (e.g., water) passes through pipes in the vaporizer 600. As this fluid passes around the cooling element 602; the fluid absorbs heat, cooling air in the cooling element 602. After the fluid absorbs the heat, the fluid can pass through a heat exchanger which transfers the heat from the fluid to air blowing through the heat exchanger. By way of further example, the cooling element 602 can comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus, the vaporizer 600 can comprise a chamber for receiving the cooling element 602 in the form of a "cold pack." The cold pack can be activated prior to insertion into the vaporizer 600 or can be activated after insertion through use of a button/switch and the like to mechanically activate the cold pack inside the vaporizer 400.

In an aspect, the cooling element 602 can be selectively moved within the vaporizer 600 to control the temperature of the air mixing with vapor. For example, the cooling element 602 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 600 to control the temperature of the air mixing with vapor. For example, the insulation can be moved to cover a portion, none, or all of the cooling element 602 to regulate temperature.

Figure 7:
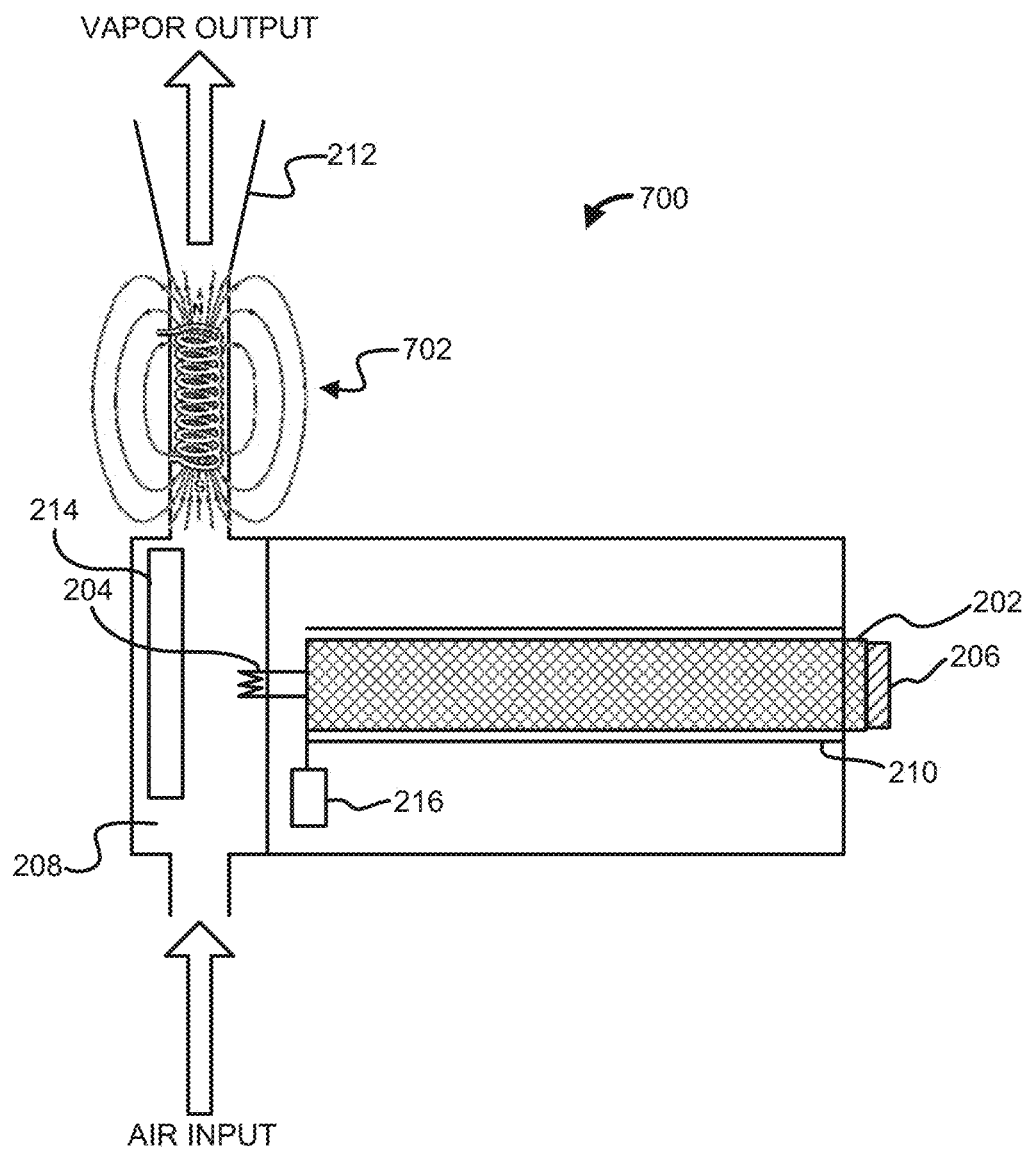
FIG. 7 illustrates another exemplary vaporizer.

FIG. 7 illustrates a vaporizer 700 that comprises elements in common with the vaporizer 200. The vaporizer 700 can optionally comprise the heating casing 402 (not shown) and/or the cooling element 602 (not shown). The vaporizer 700 can comprise a magnetic element 702. The magnetic element 702 can apply a magnetic field to vapor after exiting the mixing chamber 208. The magnetic field can cause positively and negatively charged particles in the vapor to curve in opposite directions, according to the Lorentz force law with two particles of opposite charge. The magnetic field can be created by at least one of an electric current generating a charge or a pre-charged magnetic material deployed within the robotic vapor device 100. In an aspect, the magnetic element 702 can be built into the mixing chamber 208, the cooling element 602, the heating casing 402, or can be a separate magnetic element 702.

Figure 8:
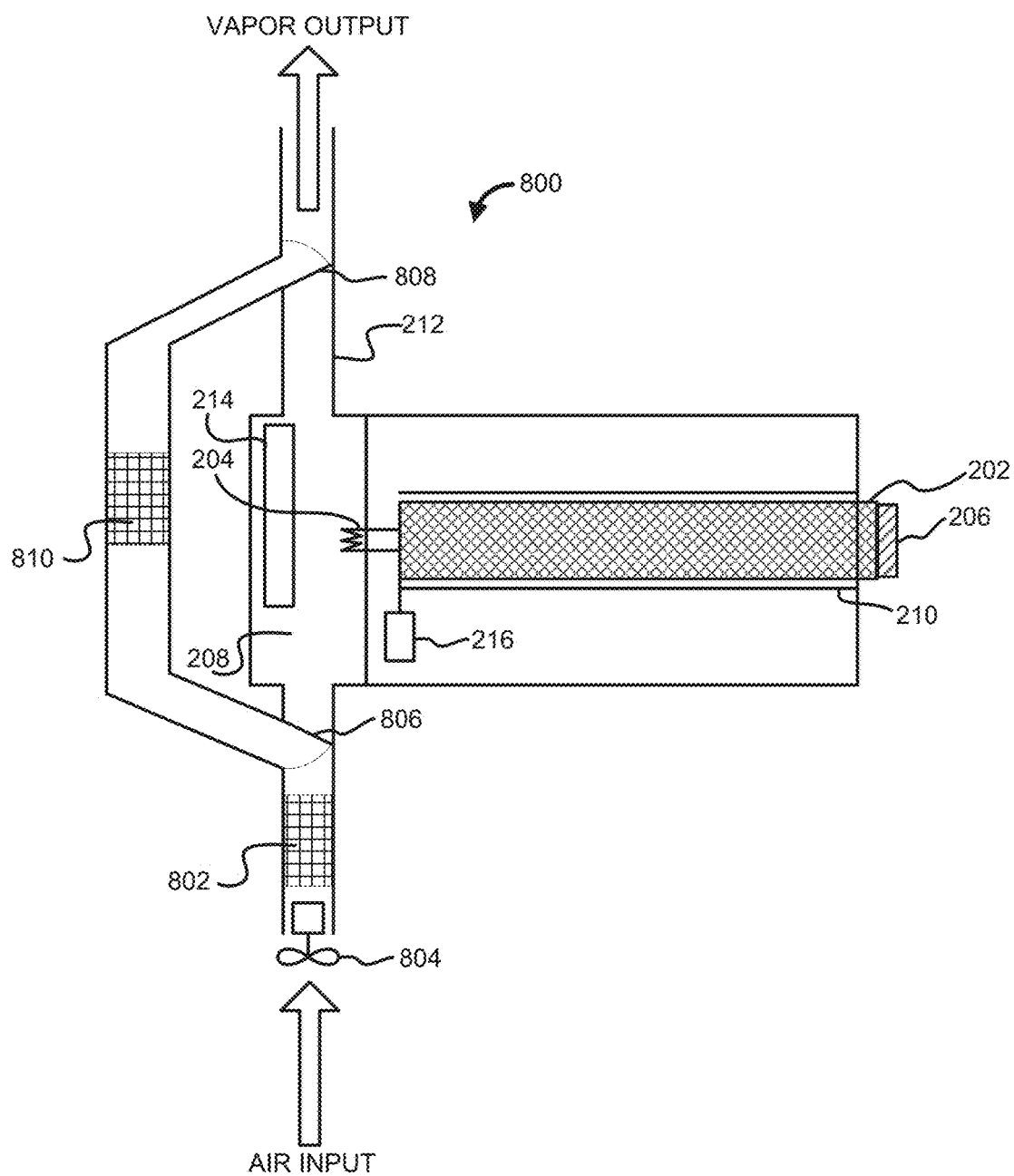
FIG. 8 illustrates an exemplary vaporizer configured for filtering air.

FIG. 8 illustrates a vaporizer 800 that comprises elements in common with the vaporizer 200. In an aspect, the vaporizer 800 can comprise a filtration element 802. The filtration element 802 can be configured to remove (e.g., filter, purify, etc) contaminants from air entering the vaporizer 800. The filtration element 802 can optionally comprise a fan 804 to assist in delivering air to the filtration element 802. The vaporizer 800 can be configured to intake air into the filtration element 802, filter the air, and pass the filtered air to the mixing chamber 208 for use in vaporizing the one or more vaporizable or non-vaporizable materials. In another aspect, the vaporizer 800 can be configured to intake air into the filtration element 802, filter the air, and bypass the mixing chamber 208 by engaging a door 806 and a door 808 to pass the filtered air directly to the exhaust port 212 for inhalation by a user. In an aspect, filtered air that bypasses the mixing chamber 208 by engaging the door 806 and the door 808 can pass through a second filtration element 810 to further remove (e.g., filter, purify, etc) contaminants from air entering the vaporizer 800. In an aspect, the vaporizer 800 can be configured to deploy and/or mix a proper/safe amount of oxygen which can be delivered either via the one or more replaceable cartridges 206 or via air pumped into a mask from external air and filtered through the filtration element 802 and/or the filtration element 810.

In an aspect, the filtration element 802 and/or the filtration element 810 can comprise cotton, polymer, wool, satin, meta materials and the like. The filtration element 802 and/or the filtration element 810 can comprise a filter material that at least one airborne particle and/or undesired gas by a mechanical mechanism, an electrical mechanism, and/or a chemical mechanism. The filter material can comprise one or more pieces of, a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 802 and/or the filtration element 810 can comprise electrostatic plates, ultraviolet light, a HEPA filter, combinations thereof, and the like.

Figure 9:
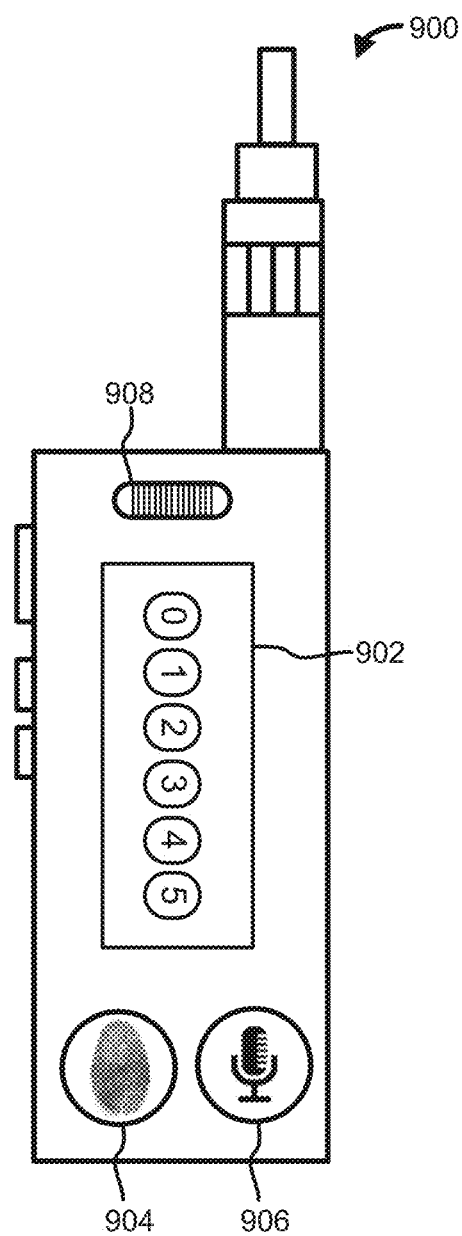
FIG. 9 illustrates an interface of an exemplary electronic vapor device.

FIG. 9 illustrates an exemplary vapor device 900. The exemplary vapor device 900 can comprise the robotic vapor device 100 and/or any of the vaporizers disclosed herein. The exemplary vapor device 900 illustrates a display 902. The display 902 can be a touchscreen. The display 902 can be configured to enable a user to control any and/or all functionality of the exemplary vapor device 900. For example, a user can utilize the display 902 to enter a pass code to lock and/or unlock the exemplary vapor device 900. The exemplary vapor device 900 can comprise a biometric interface 904. For example, the biometric interface 904 can comprise a fingerprint scanner, an eye scanner, a facial scanner, and the like. The biometric interface 904 can be configured to enable a user to control any and/or all functionality of the exemplary vapor device 900. The exemplary vapor device 900 can comprise an audio interface 906. The audio interface 906 can comprise a button that, when engaged, enables a microphone 908. The microphone 908 can receive audio signals and provide the audio signals to a processor for interpretation into one or more commands to control one or more functions of the exemplary vapor device 900. The exemplary vapor device 900 can be coupled to the robotic vapor device 101 for testing and reconfiguration.

Figure 10:
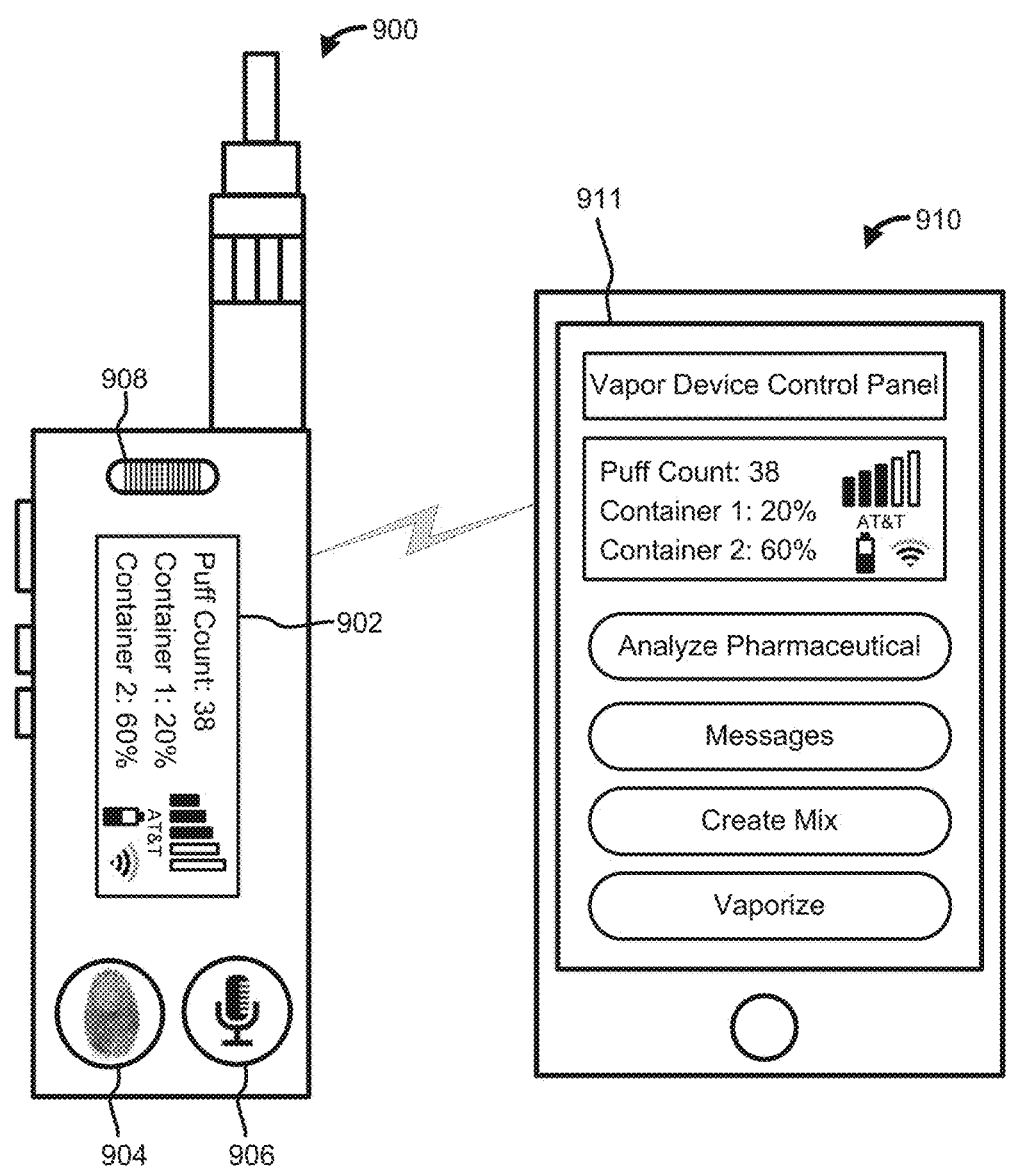
FIG. 10 illustrates another interface of an exemplary electronic vapor device.

FIG. 10 illustrates exemplary information that can be provided to a user via the display 902 of the exemplary vapor device 900 or via a display 911 of an electronic device 910 in communication with the exemplary vapor device 900. The display 902 can provide information to a user such as a puff count, an amount of vaporizable material remaining in one or more containers, battery remaining, signal strength, combinations thereof, and the like. The display 911 can provide the same or different information to the user as available on the display 902. In an aspect, the exemplary vapor device 900 does not comprise the display 902. The display 911 can provide a user interface that provides information and provides control over one or more functions of the exemplary vapor device 900. The one or more functions can comprise one or more of a community function, an e-commerce function, or a vapor device operability function. The community function can comprise at least one of a social networking function, transmitting or receiving a recommendation, transmitting or receiving a message, or transmitting or receiving a location of a user. The e-commerce function can comprise at least one of purchasing a component for use with the vapor device, purchasing a vaporizable or non-vaporizable material for use with the vapor device, purchasing another vapor device or components thereof, selling a component for use with the vapor device or another vapor device, selling a vaporizable or non-vaporizable material for use with the vapor device, or selling the vapor device or another vapor device. The device operability function can comprise at least one of controlling the vapor device, displaying diagnostic information, displaying repair information, displaying calibration information, displaying usage information, or displaying information corresponding to detected constituents of material vaporized by the vapor device.

The user interface can comprise at least one of a lighted signal light, a gauge, a representation of a box, a representation of a form, a check mark, an avatar, a visual image, a graphic design, a list, an active calibration or calculation, a 2-dimensional fractal design, a 3-dimensional fractal design, a 2-dimensional representation of the vapor device or another vapor device, or a 3-dimensional representation of the vapor device or another vapor device. At least one of the 2-dimensional fractal design or the 3-dimensional fractal design can continuously or periodically expand or contract to various scales of the original fractal design.

Figure 11:
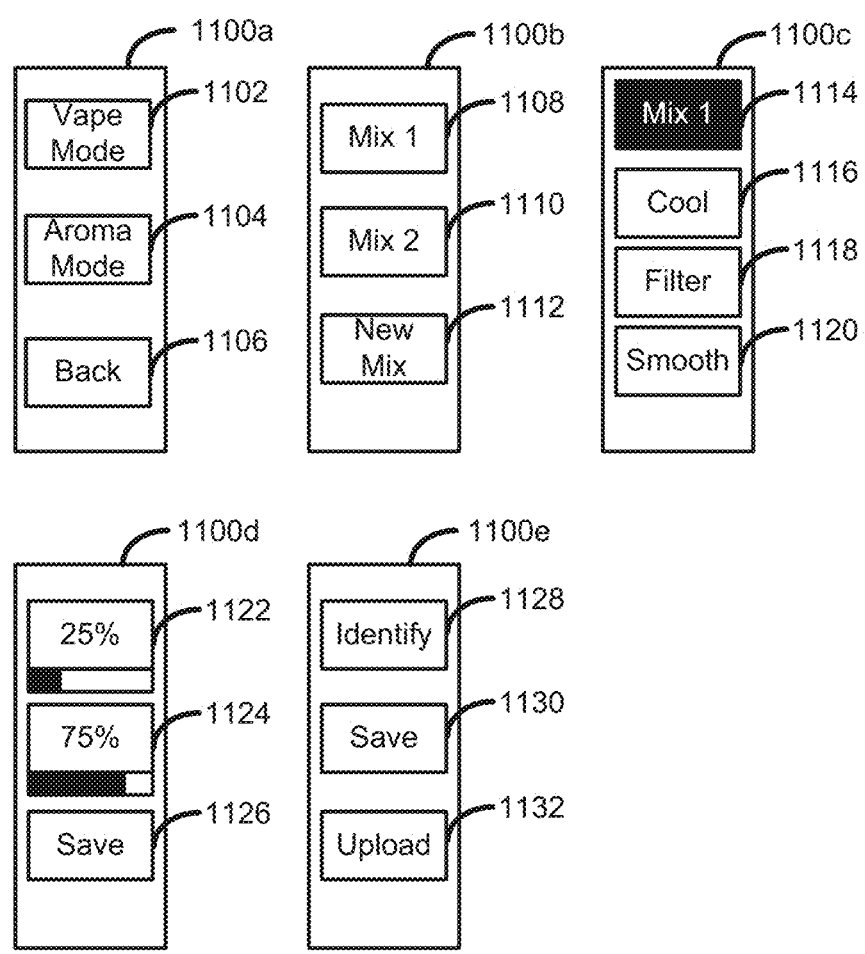
FIG. 11 illustrates several interfaces of an exemplary electronic vapor device.

FIG. 11 illustrates a series of user interfaces that can be provided via the display 902 of the exemplary vapor device 900 or via the display 911 of the electronic device 910 in communication with the exemplary vapor device 900. In an aspect, the exemplary vapor device 900 can be configured for one or more of multi-mode vapor usage. For example, the exemplary vapor device 900 can be configured to enable a user to inhale vapor (vape mode) or to release vapor into the atmosphere (aroma mode). User interface 1100a provides a user with interface elements to select which mode the user wishes to engage, a Vape Mode 1102, an Aroma Mode 1104, or an option to go back 1106 and return to the previous screen. The interface element Vape Mode 1102 enables a user to engage a vaporizer to generate a vapor for inhalation. The interface element Aroma Mode 1104 enables a user to engage the vaporizer to generate a vapor for release into the atmosphere.

In the event a user selects the Vape Mode 1102, the exemplary vapor device 900 will be configured to vaporize material and provide the resulting vapor to the user for inhalation. The user can be presented with user interface 1100b which provides the user an option to select interface elements that will determine which vaporizable material to vaporize. For example, an option of Mix 1 1108, Mix 2 1110, or a New Mix 1112. The interface element Mix 1 1108 enables a user to engage one or more containers that contain vaporizable material in a predefined amount and/or ratio. In an aspect, a selection of Mix 1 1108 can result in the exemplary vapor device 900 engaging a single container containing a single type of vaporizable material or engaging a plurality of containers containing a different types of vaporizable material in varying amounts. The interface element Mix 2 1110 enables a user to engage one or more containers that contain vaporizable material in a predefined amount and/or ratio. In an aspect, a selection of Mix 2 1110 can result in the exemplary vapor device 900 engaging a single container containing a single type of vaporizable material or engaging a plurality of containers containing a different types of vaporizable material in varying amounts. In an aspect, a selection of New Mix 1112 can result in the exemplary vapor device 900 receiving a new mixture, formula, recipe, etc. . . . of vaporizable materials and/or engage one or more containers that contain vaporizable material in the new mixture.

Upon selecting, for example, the Mix 1 1108, the user can be presented with user interface 1100e. User interface 1100c indicates to the user that Mix 1 has been selected via an indicator 1114. The user can be presented with options that control how the user wishes to experience the selected vapor. The user can be presented with interface elements Cool 1116, Filter 1118, and Smooth 1120. The interface element Cool 1116 enables a user to engage one or more cooling elements to reduce the temperature of the vapor. The interface element Filter 1118 enables a user to engage one or more filter elements to filter the air used in the vaporization process. The interface element Smooth 1120 enables a user to engage one or more heating casings, cooling elements, filter elements, and/or magnetic elements to provide the user with a smoother vaping experience.

Upon selecting New Mix 1112, the user can be presented with user interface 1100d. User interface 1100d provides the user with a container one ratio interface element 1122, a container two ratio interface element 1124, and Save 1126. The container one ratio interface element 1122 and the container two ratio interface element 1124 provide a user the ability to select an amount of each type of vaporizable material contained in container one and/or container two to utilize as a new mix. The container one ratio interface element 1122 and the container two ratio interface element 1124 can provide a user with a slider that adjusts the percentages of each type of vaporizable material based on the user dragging the slider. In an aspect, a mix can comprise 100% on one type of vaporizable material or any percent combination (e.g., 50/50, 75/25, 85/15, 95/5, etc. . . . ). Once the user is satisfied with the new mix, the user can select Save 1126 to save the new mix for later use.

In the event a user selects the Aroma Mode 1104, the exemplary vapor device 900 will be configured to vaporize material and release the resulting vapor into the atmosphere. The user can be presented with user interface 1100b, 1100e, and/or 1100d as described above, but the resulting vapor will be released to the atmosphere.

In an aspect, the user can be presented with user interface 1100e. The user interface 1100e can provide the user with interface elements Identify 1128, Save 1130, and Upload 1132. The interface element Identify 1128 enables a user to engage one or more sensors in the exemplary vapor device 900 to analyze the surrounding environment. For example, activating the interface element Identify 1128 can engage a sensor to determine the presence of a negative environmental condition such as smoke, a bad smell, chemicals, etc. Activating the interface element Identify 1128 can engage a sensor to determine the presence of a positive environmental condition, for example, an aroma. The interface element Save 1130 enables a user to save data related to the analyzed negative and/or positive environmental condition in memory local to the exemplary vapor device 900. The interface element Upload 1132 enables a user to engage a network access device to transmit data related to the analyzed negative and/or positive environmental condition to a remote server for storage and/or analysis.

In an aspect, the user interfaces provided via the display 902 of the exemplary vapor device 900 can be used to select a mix of vaporizable material for vaporization. The exemplary vapor device 900 can be coupled to the robotic vapor device 101 and the mix can be vaporized and resultant vapor drawn into the robotic vapor device 101. The robotic vapor device 101 can analyze the vapor and provide information related to the contents of the vapor. The information can be compared to the intended mix to confirm that the exemplary vapor device 900 does not require calibration to properly mix and/or vaporize the mix of vaporizable material.

Figure 12:
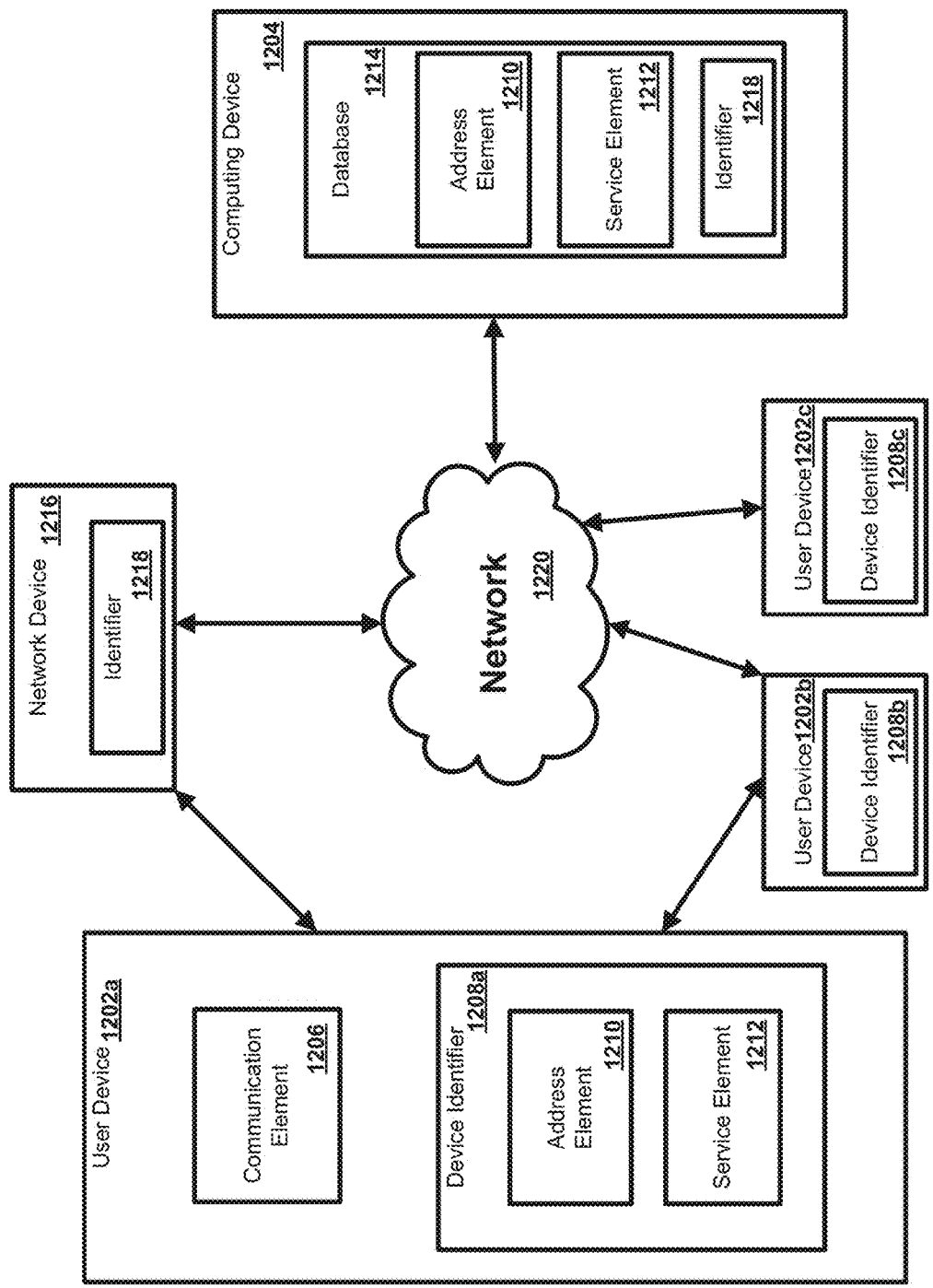
FIG. 12 illustrates an exemplary operating environment.

In one aspect of the disclosure, a system can be configured to provide services such as network-related services to a user device. FIG. 12 illustrates various aspects of an exemplary environment in which the present methods and systems can operate. The present disclosure is relevant to systems and methods for providing services to a user device, for example, electronic vapor devices which can include, but are not limited to, a vape-bot, micro-vapor device, vapor pipe, e-cigarette, hybrid handset and vapor device, and the like. Other user devices that can be used in the systems and methods include, but are not limited to, a smart watch (and any other form of "smart" wearable technology), a smartphone, a tablet, a laptop, a desktop, and the like. In an aspect, one or more network devices can be configured to provide various services to one or more devices, such as devices located at or near a premises. In another aspect, the network devices can be configured to recognize an authoritative device for the premises and/or a particular service or services available at the premises. As an example, an authoritative device can be configured to govern or enable connectivity to a network such as the Internet or other remote resources, provide address and/or configuration services like DHCP, and/or provide naming or service discovery services for a premises, or a combination thereof. Those skilled in the art will appreciate that present methods can be used in various types of networks and systems that employ both digital and analog equipment. One skilled in the art will appreciate that provided herein is a functional description and that the respective functions can be performed by software, hardware, or a combination of software and hardware.

The network and system can comprise a user device 1202a, 1202b, and/or 1202c in communication with a computing device 1204 such as a server, for example. The computing device 1204 can be disposed locally or remotely relative to the user device 1202a, 1202b, and/or 1202c. As an example, the user device 1202a, 1202b, and/or 1202c and the computing device 1204 can be in communication via a private and/or public network 1220 such as the Internet or a local area network. Other forms of communications can be used such as wired and wireless telecommunication channels, for example. In another aspect, the user device 1202a, 1202*b*, and/or 1202*c* can communicate directly without the use of the network 1220 (for example, via Bluetooth®, infrared, and the like).

In an aspect, the user device 1202*a*, 1202*b*, and/or 1202*c* can be an electronic device such as an electronic vapor device (e.g., vape-bot, micro-vapor device, vapor pipe, e-cigarette, hybrid handset and vapor device), a robotic vapor device, a smartphone, a smart watch, a computer, a smartphone, a laptop, a tablet, a set top box, a display device, or other device capable of communicating with the computing device 1204. As an example, the user device 1202*a*, 1202*b*, and/or 1202*c* can comprise a communication element 1206 for providing an interface to a user to interact with the user device 1202*a*, 1202*b*, and/or 1202*c* and/or the computing device 1204. The communication element 1206 can be any interface for presenting and/or receiving information to/from the user, such as user feedback. An example interface can be communication interface such as a web browser (e.g., Internet Explorer, Firefox, Google Chrome, Safari, or the like). Other software, hardware, and/or interfaces can be used to provide communication between the user and one or more of the user device 1202*a*, 1202*b*, and/or 1202*c* and the computing device 1204. In an aspect, the user device 1202*a*, 1202*b*, and/or 1202*c* can have at least one similar interface quality such as a symbol, a voice activation protocol, a graphical coherence, a startup sequence continuity element of sound, light, vibration or symbol. In an aspect, the interface can comprise at least one of lighted signal lights, gauges, boxes, forms, words, video, audio scrolling, user selection systems, vibrations, check marks, avatars, matrix', visual images, graphic designs, lists, active calibrations or calculations, 2D interactive fractal designs, 3D fractal designs, 2D and/or 3D representations of vapor devices and other interface system functions.

In an aspect, the user device 1202*a*, 1202*b*, and/or 1202*c* can form a peer-to-peer network. The user device 1202*a*, 1202*b*, and/or 1202*c* can be configured for measuring air in proximity to each of the user device 1202*a*, 1202*b*, and/or 1202*c* and report any resulting measurement data (e.g., concentration of one or more constituents, and the like) to each of the other of the user device 1202*a*, 1202*b*, and/or 1202*c*. Thus, each of the user device 1202*a*, 1202*b*, and/or 1202*c* can derive a profile for distribution of one or more constituents within an area monitored by the user device 1202*a*, 1202*b*, and/or 1202*c*. Each of the user device 1202*a*, 1202*b*, and/or 1202*c* can make a determination whether to vaporize one or more vaporizable materials (and which vaporizable materials to vaporize) based on an analysis of the total measurement data combined from each of the user device 1202*a*, 1202*b*, and/or 1202*c*. For example, the user device 1202*a* can determine report the presence of constituent A to the user device 1202*b* and/or 1202*c*, the user device 1202*b* can determine report the presence of constituent A to the user device 1202*a* and/or 1202*c*, and the user device 1202*c* can determine report the presence of constituent A to the user device 1202*a* and/or 1202*b*. It may be determined that the presence of constituent A exceeds a threshold established by an air treatment protocol in the proximity of user device 1202*a* and user device 1202*b*. Accordingly, user device 1202*m* and user device 1202*b* can determine to vaporize one or more vaporizable materials to counter the effects of constituent A in amounts relative to the presence of constituent A in proximity to each device. User device 1202*c* can either not vaporize one or more vaporizable materials to counter the effects of constituent A or, depending on the air treatment protocol, the user device 1202*c* can vaporize one or more vaporizable materials to counter the effects of constituent A, despite the presence of constituent A in the proximity of the user device 1202*c* not exceeding a threshold.

As an example, the communication element 1206 can request or query various files from a local source and/or a remote source. As a further example, the communication element 1206 can transmit data to a local or remote device such as the computing device 1204. In an aspect, data can be shared anonymously with the computing device 1204.

In an aspect, the user device 1202*m*, 1202*b*, and/or 1202*c* can be associated with a user identifier or device identifier 1208*a*, 1208*b*, and/or 1208*c*. As an example, the device identifier 1208*a*, 1208*b*, and/or 1208*c* can be any identifier, token, character, string, or the like, for differentiating one user or user device (e.g., user device 1202*a*, 1202*b*, and/or 1202*c*) from another user or user device. In a further aspect, the device identifier 1208*a*, 1208*b*, and/or 1208*c* can identify a user or user device as belonging to a particular class of users or user devices. As a further example, the device identifier 1208*a*, 1208*b*, and/or 1208*c* can comprise information relating to the user device such as a manufacturer, a model or type of device, a service provider associated with the user device 1202*a*, 1202*b*, and/or 1202*c*, a state of the user device 1202*a*, 1202*b*, and/or 1202*c*, a locator, and/or a label or classifier. Other information can be represented by the device identifier 1208*a*, 1208*b*, and/or 1208*c*.

In an aspect, the device identifier 1208*a*, 1208*b*, and/or 1208*c* can comprise an address element 1210 and a service element 1212. In an aspect, the address element 1210 can comprise or provide an internet protocol address, a network address, a media access control (MAC) address, an Internet address, or the like. As an example, the address element 1210 can be relied upon to establish a communication session between the user device 1202*a*, 1202*b*, and/or 1202*c* and the computing device 1204 or other devices and/or networks. As a further example, the address element 1210 can be used as an identifier or locator of the user device 1202*a*, 1202*b*, and/or 1202*c*. In an aspect, the address element 1210 can be persistent for a particular network.

In an aspect, the service element 1212 can comprise an identification of a service provider associated with the user device 1202*a*, 1202*b*, and/or 1202*c* and/or with the class of user device 1202*a*, 1202*b*, and/or 1202*c*. The class of the user device 1202*a*, 1202*b*, and/or 1202*c* can be related to a type of device, capability of device, type of service being provided, and/or a level of service. As an example, the service element 1212 can comprise information relating to or provided by a communication service provider (e.g., Internet service provider) that is providing or enabling data flow such as communication services to and/or between the user device 1202*a*, 1202*b*, and/or 1202*c*. As a further example, the service element 1212 can comprise information relating to a preferred service provider for one or more particular services relating to the user device 1202*a*, 1202*b*, and/or 1202*c*. In an aspect, the address element 1210 can be used to identify or retrieve data from the service element 1212, or vice versa. As a further example, one or more of the address element 1210 and the service element 1212 can be stored remotely from the user device 1202*a*, 1202*b*, and/or 1202*c* and retrieved by one or more devices such as the user device 1202*a*, 1202*b*, and/or 1202*c* and the computing device 1204. Other information can be represented by the service element 1212.

In an aspect, the computing device 1204 can be a server for communicating with the user device 1202*a*, 1202*b*, and/or 1202*c*. As an example, the computing device 1204 can communicate with the user device 1202*a*, 1202*b*, and/or

1202c for providing data and/or services. As an example, the computing device 1204 can provide services such as calibration analysis, vapor analysis, data sharing, data syncing, network (e.g., Internet) connectivity, network printing, media management (e.g., media server), content services, and the like. In an aspect, the computing device 1204 can allow the user device 1202a, 1202b, and/or 1202c to interact with remote resources such as data, devices, and files. As an example, the computing device can be configured as (or disposed at) a central location, which can receive content (e.g., data) from multiple sources, for example, user devices 1202a, 1202b, and/or 1202c. The computing device 1204 can combine the content from the multiple sources and can distribute the content to user (e.g., subscriber) locations via a distribution system.

In an aspect, one or more network devices 1216 can be in communication with a network such as network 1220. As an example, one or more of the network devices 1216 can facilitate the connection of a device, such as user device 1202a, 1202b, and/or 1202c, to the network 1220. As a further example, one or more of the network devices 1216 can be configured as a wireless access point (WAP). In an aspect, one or more network devices 1216 can be configured to allow one or more wireless devices to connect to a wired and/or wireless network using Wi-Fi, Bluetooth or any desired method or standard.

In an aspect, the network devices 1216 can be configured as a local area network (LAN). As an example, one or more network devices 1216 can comprise a dual band wireless access point. As an example, the network devices 1216 can be configured with a first service set identifier (SSID) (e.g., associated with a user network or private network) to function as a local network for a particular user or users. As a further example, the network devices 1216 can be configured with a second service set identifier (SSID) (e.g., associated with a public/community network or a hidden network) to function as a secondary network or redundant network for connected communication devices.

In an aspect, one or more network devices 1216 can comprise an identifier 1218. As an example, one or more identifiers can be or relate to an Internet Protocol (IP) Address IPV4/IPV6 or a media access control address (MAC address or the like. As a further example, one or more identifiers 1218 can be a unique identifier for facilitating communications on the physical network segment. In an aspect, each of the network devices 1216 can comprise a distinct identifier 1218. As an example, the identifiers 1218 can be associated with a physical location of the network devices 1216.

In an aspect, the computing device 1204 can manage the communication between the user device 1202a, 1202b, and/or 1202c and a database 1214 for sending and receiving data therebetween. As an example, the database 1214 can store a plurality of files (e.g., web pages), user identifiers or records, or other information. In one aspect, the database 1214 can store user device 1202a, 1202b, and/or 1202c usage information (including chronological usage), test results, type of vaporizable and/or non-vaporizable material used, frequency of usage, location of usage, recommendations, communications (e.g., text messages, advertisements, photo messages), simultaneous use of multiple devices, and the like). The database 1214 can collect and store data to support cohesive use, wherein cohesive use is indicative of the use of a first electronic vapor devices and then a second electronic vapor device is synced chronologically and logically to provide the proper specific properties and amount of vapor based upon a designed usage cycle. As a further example, the user device 1202a, 1202b, and/or 1202c can request and/or retrieve a file from the database 1214. The user device 1202a, 1202b, and/or 1202c can thus sync locally stored data with more current data available from the database 1214. Such syncing can be set to occur automatically on a set time schedule, on demand, and/or in real-time. The computing device 1204 can be configured to control syncing functionality. For example, a user can select one or more of the user device 1202a, 1202b, and/or 1202c to never by synced, to be the master data source for syncing, and the like. Such functionality can be configured to be controlled by a master user and any other user authorized by the master user or agreement.

In an aspect, data can be derived by system and/or device analysis. Such analysis can comprise at least by one of instant analysis performed by the user device 1202a, 1202b, and/or 1202c or archival data transmitted to a third party for analysis and returned to the user device 1202a, 1202b, and/or 1202c and/or computing device 1204. The result of either data analysis can be communicated to a user of the user device 1202a, 1202b, and/or 1202c to, for example, inform the user of their vapor device configuration, eVapor use and/or lifestyle options. In an aspect, a result can be transmitted back to at least one authorized user interface. For example, a chemical signature of a pharmaceutical can be obtained via the user device 1202a, 1202b, and/or 1202c, stored and/or transmitted to the computing device 1204. The user device 1202a, 1202b, and/or 1202e and/or the computing device 1204 can store a database of known chemical signatures and can compare a chemical signature obtained via the user device 1202a, 1202b, and/or 1202c to the database of known chemical signatures to determine an identify of a pharmaceutical or other substance.

In an aspect, the database 1214 can store information relating to the user device 1202a, 1202b, and/or 1202c such as the address element 1210 and/or the service element 1212. As an example, the computing device 1204 can obtain the device identifier 1208a, 1208b, and/or 1208c from the user device 1202a, 1202b, and/or 1202c and retrieve information from the database 1214 such as the address element 1210 and/or the service elements 1212. As a further example, the computing device 1204 can obtain the address element 1210 from the user device 1202a, 1202b, and/or 1202c and can retrieve the service element 1212 from the database 1214, or vice versa. Any information can be stored in and retrieved from the database 1214. The database 1214 can be disposed remotely from the computing device 1204 and accessed via direct or indirect connection. The database 1214 can be integrated with the computing device 1204 or some other device or system. Data stored in the database 1214 can be stored anonymously and can be destroyed based on a transient data session reaching a session limit.

By way of example, one or more of the user device 1202a, 1202b, and/or 1202c can comprise a robotic vapor device and one or more of the user device 1202a, 1202b, and/or 1202c can comprise a vapor device coupled to the robotic vapor device for testing and/or reconfiguration. The robotic vapor device can draw vapor from the vapor device (e.g., as a user would inhale from the vapor device) and analyze the resulting vapor. In an aspect, the robotic vapor device can transmit testing results and or data to the computing device 1204 for analysis. For example, a determination can be made that the vapor device is generating vapor at a temperature above a recommend limit. A reconfiguration command can be sent to the vapor device (e.g., via the robotic vapor device and/or the computing device 1204) to lower the temperature at which vaporization occurs. Any number of other functions/features/aspects of operation of the vapor device can be tested/analyzed and reconfigured.

Figure 13:
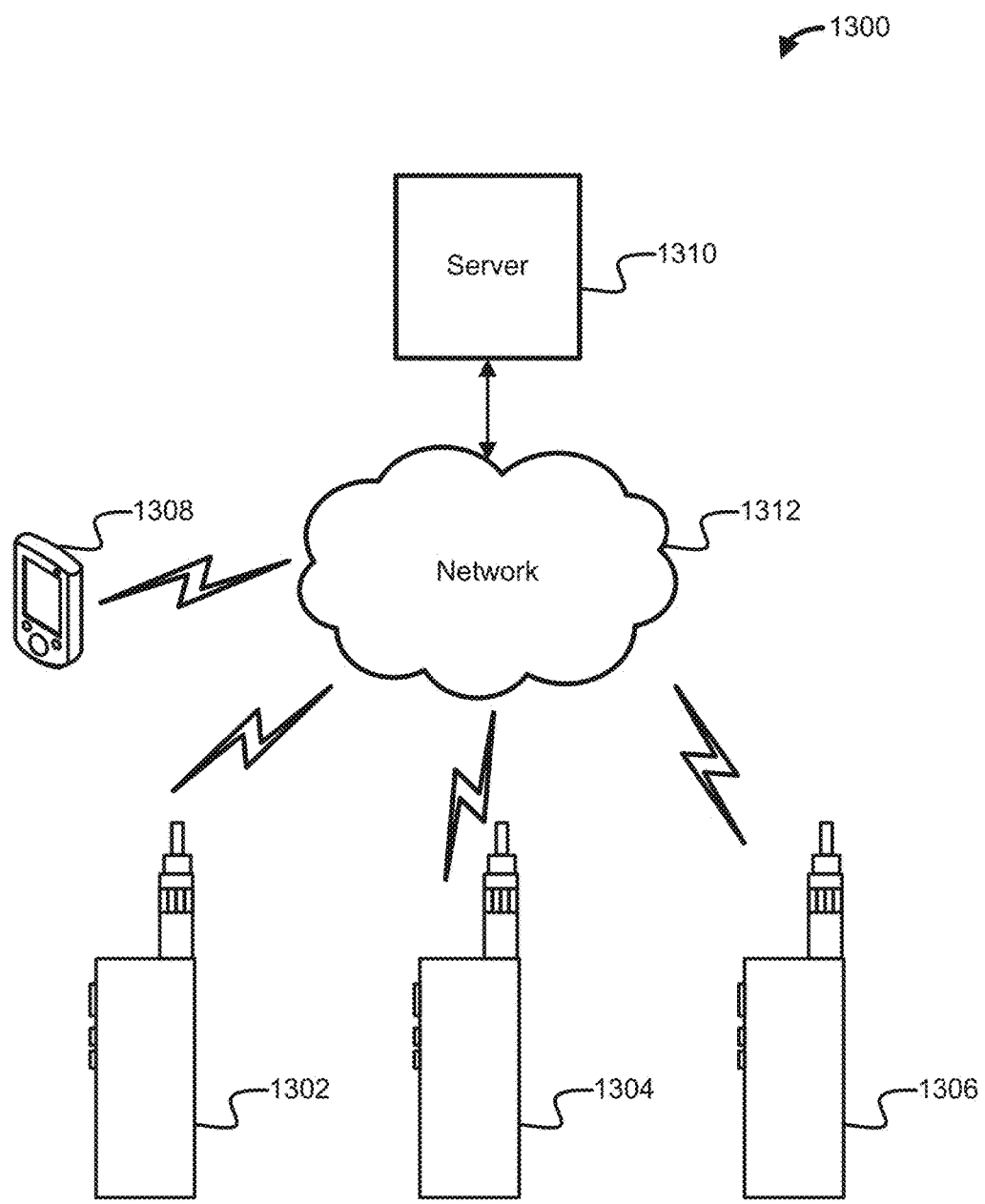
FIG. 13 illustrates another exemplary operating environment.

FIG. 13 illustrates an ecosystem 1300 configured for sharing and/or syncing data such as usage information (including chronological usage), testing data, reconfiguration data, type of vaporizable and/or non-vaporizable material used, frequency of usage, location of usage, recommendations, communications (e.g., text messages, advertisements, photo messages), simultaneous use of multiple devices, and the like) between one or more devices such as a vapor device 1302, a vapor device 1304, a vapor device 1306, and an electronic communication device 1308. In an aspect, the vapor device 1302, the vapor device 1304, the vapor device 1306 can be one or more of an e-cigarette, an e-cigar, an electronic vapor modified device, a hybrid electronic communication handset coupled/integrated vapor device, a micro-sized electronic vapor device, or a robotic vapor device. In an aspect, the electronic communication device 1308 can comprise one or more of a smartphone, a smart watch, a tablet, a laptop, and the like.

In an aspect data generated, gathered, created, etc., by one or more of the vapor device 1302, the vapor device 1304, the vapor device 1306, and/or the electronic communication device 1308 can be uploaded to and/or downloaded from a central server 1310 via a network 1312, such as the Internet. Such uploading and/or downloading can be performed via any form of communication including wired and/or wireless. In an aspect, the vapor device 1302, the vapor device 1304, the vapor device 1306, and/or the electronic communication device 1308 can be configured to communicate via cellular communication, WiFi communication, Bluetooth® communication, satellite communication, and the like. The central server 1310 can store uploaded data and associate the uploaded data with a user and/or device that uploaded the data. The central server 1310 can access unified account and tracking information to determine devices that are associated with each other, for example devices that are owned/used by the same user. The central server 1310 can utilize the unified account and tracking information to determine which of the vapor device 1302, the vapor device 1304, the vapor device 1306, and/or the electronic communication device 1308, if any, should receive data uploaded to the central server 1310. For example, the central server 1310 can receive reconfiguration data generated as a result of analysis of the vapor device 1302 the vapor device 1304, the vapor device 1306 by a robotic vapor device. The reconfiguration data can be shared with one or more of the vapor device 1302, the vapor device 1304, the vapor device 1306 to reconfigure the vapor device 1302, the vapor device 1304, and/or the vapor device 1306.

In an aspect, the vapor device 1302, the vapor device 1304, and/or the vapor device 1306 can be in communication with the electronic communication device 1308 to enable the electronic communication device 1308 to generate a user interface to display information about and to control one or more functions/features of the vapor device 1302, the vapor device 1304, and/or the vapor device 1306. The electronic communication device 1308 can request access to one or more of the vapor device 1302, the vapor device 1304, and/or the vapor device 1306 from the central server 1310. The central server 1310 can determine whether or not the electronic communication device 1308 (or a user thereof) is authorized to access the one or more of the vapor device 1302, the vapor device 1304, and/or the vapor device 1306. If the central server 1310 determines that access should be granted, the central server 1310 can provide an authorization token to the electronic communication device 1308 (or to the vapor device 1302, the vapor device 1304, and/or the vapor device 1306 on behalf of the electronic communication device 1308). Upon receipt of the authorization token, the one or more of the vapor device 1302, the vapor device 1304, and/or the vapor device 1306 can partake in a communication session with the electronic communication device 1308 whereby the electronic communication device 1308 generates a user interface that controls one or more functions/features of and displays information about the one or more of the vapor device 1302, the vapor device 1304, and/or the vapor device 130.

Figure 14:
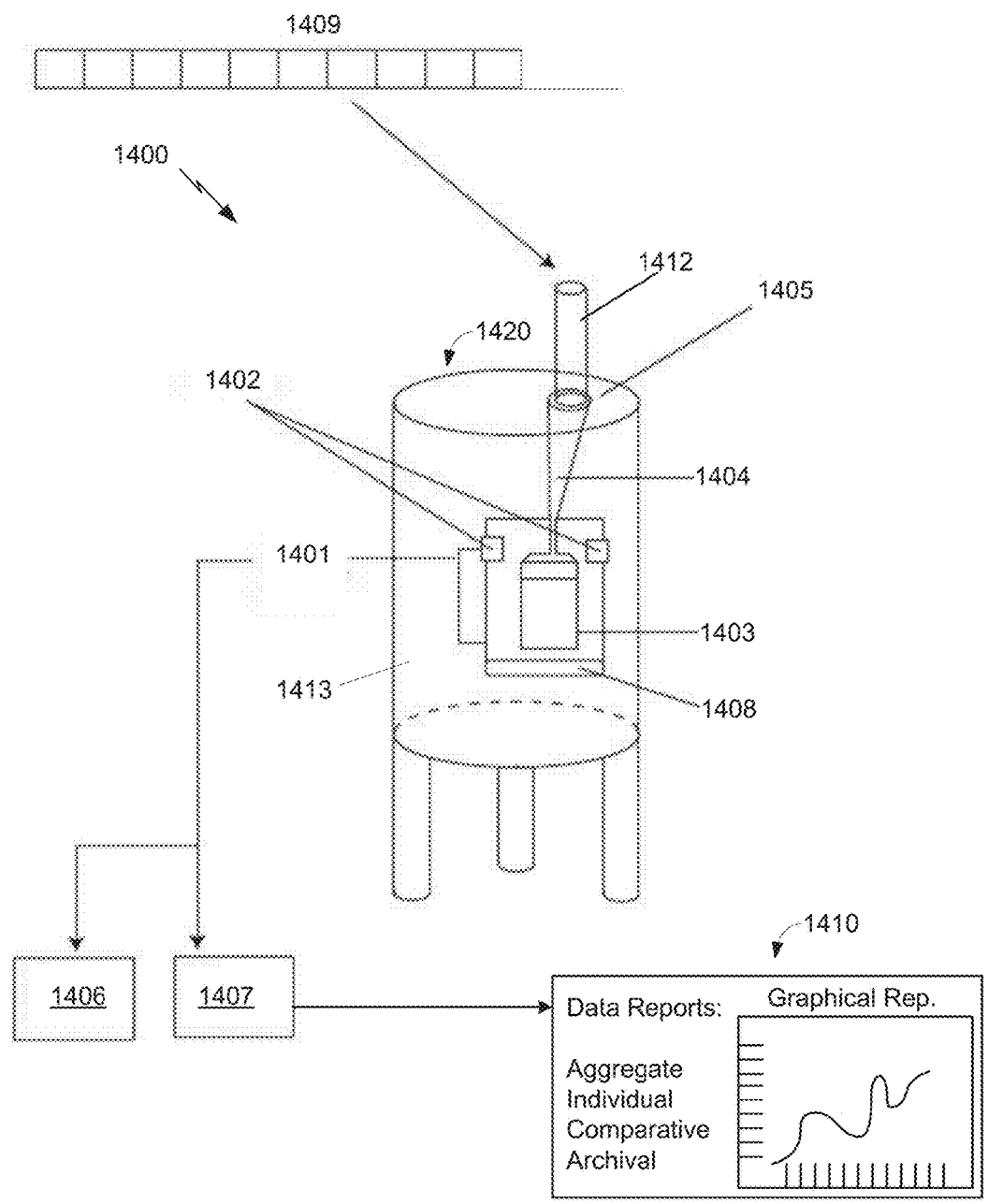
FIG. 14 is a schematic diagram illustrating an analysis device for analyzing prescription medications.

Aspects of the present disclosure pertain to the manufacture, design, implementation, and installation of a robotic sensing intake and distribution vapor device 1420, shown in FIG. 14. The robotic pharmaceutical testing device 1420 may also be called a "robotic vapor device" (RVD), or a "chemical analysis device" or "Vape-Bot"™ for brevity. Whatever it is called, the device 1420 may be equipped to test and analyze medications 1409 or other substances emitted from a personal vaporizer 1412 and/or emitted from a prescription medication or compound of multiple prescription medications. It may also perform other functions, for example air treatment, beyond the scope of the present disclosure. The materials emitted from a sample may be drawn by a suction pump 1405 along a vapor path 1404 into an analysis chamber 1403, and/or emitted from a prescription medication directly placed within an analysis chamber 1403. Besides regulated forms of capsules, syrups, injectable liquids or pills, prescription medications or pharmaceuticals to be tested may also include, broadly speaking for example, nutritional supplements, veterinary medications or supplements, dried or processed herbs, tinctures, essences, oils, and foods, regulated or not.

The analysis chamber 1403 may be warmed by a power source 1408, such as to decarboxylate various components of the prescription medication(s) 1409 forming gases, vapors and or the like of the prescription medication. The device may be equipped to exhaust such gases or substances to an ambient environment, and to communicate with other components 1406, 1407 of a networked system 1400.

In addition, the device 1420 may have the ability to intake and test ambient air quality, as well as output from personal vaporizers (e.g., vaporizer device 1412) by the expedient of simply removing the attached vaporizer 1412 or replacing the vaporizer with a desired pre-treatment system such as a filter. In either case, the Vape-Bot 1420 may include a suction mechanism 1405 comprising, for example, a piston in cylinder 1403 (which doubles as the analysis chamber 1403), a bellows, or an intake fan. The suction mechanism may be set at a constant rate or at a rate designed to simulate human respiration, drawing air in through a vapor path 1404. Once analyzed (or immediately, if no analysis is to be performed) the in-drawn vapor or mixture may be exhausted via the vapor path 1404, or via a different outlet (not shown). Components of the device 1420 may be contained in any suitable housing 1413, illustrated schematically as a cylinder.

Furthermore, the device 1420 may analyze vapor or gaseous substances using at least one of a sensor array 1402 or a gas chromatograph/mass spectrometry system (GC/MS, not shown) installed within the robotic device and coupled to an analysis chamber 1403. Sensor data and spectrometry analysis data may be provided to a data processing and control system 1401 in the device 1420, and utilized for analysis. The processing and control system may analyze the sensor or spectrometer data by comparison to a cached database 1406 for element and level matching, using an engine comprising analysis algorithms. In the alternative, or in addition, measurement data may be securely transmitted to at least one remote database 1406 for analysis and subsequent transmission 1407 back to the robotic device or at least one interface thereof on the instant device such as a user interface display operatively coupled to the device or any authorized third party device, such as a remote authorized system user interface device operatively coupled to the device by a network. Thus, data may be displayed on any web enabled, system authorized device, such as a remote device, and/or may be displayed directly on a user display device (e.g., detail screen) in operative communication with a processor of the device 1420 such as via a data transmission 1407.

Moreover, the device 1420 may perform composition analysis 1409 and may display the results of composition analysis 1409 on a detail screen and/or the web enabled, system authorized device. The composition analysis 1409 may include aggregate, individual, comparative, and/or archival reports presenting both instant and/or historical data on the composition, purity, contamination, identity, and/or the like of the prescription medication(s) 1409 under test, such as to identify the specific variety of prescription medication from among a family of related prescription medications or to identify the presence, absence, and/or concentration of impurities in the prescription medication (e.g., formaldehyde, pesticides, etc.) whether residing directly in the prescription medication, or provided by a carrier of the prescription medication such as an oil, resin, container, and/or the like, or to determine the purity, strength, ratio, composition, and/or any other desired feature of the prescription medication(s) under test, whether in conjunction with comparison to local historical data or remote historical data or date regarding known prescription medication formulations as may be stored in a cached database 1406.

As used herein, "analyzing" and "analysis" may mean various different operations. For instance, the composition analysis 1409 may also include evaluating the prescription medication, or classifying the prescription medication, such as according to a stored taxonomy from a database, comparing the composition of one sample of prescription medication to the composition of another sample or samples of prescription medication(s), validating that the prescription medication conforms to expected parameters, such as composition, absence of impurities, purity, ratio of compounded prescription medications, and/or the like, refuting a prior classification of the prescription medication, such as to correct misidentification, and/or cataloging the prescription medication, such as to store a database of varieties, to organize prescription medications according to composition, absence of impurities, purity, ratio of compounded prescription medications and/or the like, and/or to permit a user to store individualized notes regarding the prescription medication, such as to permit custom catalogs or storage of treatment plans or custom prescription medication formulations and/or compounds.

Analysis may further include determining various data, such as mass spectrometry, PH testing, genetic testing, particle and cellular testing, synthetic molecular analysis, sensor based testing, diagnostic testing, and wellness testing of the prescription medication. This data may be relied upon by a processor to perform the analysis discussed herein. The outcome of the analysis may be data characterizing the prescription medication, which may then (as discussed) be displayed as a composition analysis 1409 according to the system and methods discussed herein.

A purity analysis may include a variety of user readable dialogs displayed at a user interface device. For instance, such user readable dialogs may include lighted signal lights, gauges, boxes, forms, check marks, avatars, visual images, graphic designs, lists, active calibrations (such as of this or another device, substance mixing and compounding apparatus and the like), calculations, 2D interactive fractal designs, 3D fractal designs, 2D representations of a vapor device, 3D representations of a vapor devices, or any other representative mechanism as desired.

Novel aspects of the vapor device 1420 and system 1400, and methods for their use, may include a portable, robotic pharmaceutical testing apparatus that can be used in the home or at a commercial establishment to provide a rapid and accurate analysis of output from a personal vaporizer 1412. For example, constituents of vapor output may be analyzed to detect the purity and potency of the vapor or other material emitted by the vaporizer, from which repeatable information about the material under test may be obtained and compared to a database of similarly tested materials. The The device 1420 also be used to track vapor residue (e.g., particulate or non-volatile residuals), levels of inhalation of specific chemicals, impact of different draw rates or respiration patterns on vaporizer output and determinations of positive and negative impacts of vapor inhalation usage. This information may be based not only on the chemical raw data gauged at intake by the device, but also on comparisons of that data to other known data in local or remote databases. Such comparisons can be made a static environment or dynamic sensor data environment. For example, the device 1420 may be equipped with any number of sensor components or targets, including, for example, PH gauges, human/animal/plant or simulated tissue and any other number of other materials testing beds.

As an ancillary function, the Vape-Bot 1420 may also be used to distribute desired vapor into environments based upon a specific order or setting of the system. This vapor does not require a human to inhale the vapor. Instead, the vapor may be delivered via an outtake exhaust system, which may exhaust in a steady, rhythmic or sporadic output stream. Once the desired level of the desired vapor elements have been disbursed by the device 1420, the device may then cease to deliver such elements until there is another need. This need may be determined by demand of an authorized party, or triggered via a sensor reading within a space that the robotic vapor device 1420 is serving with customized vapor. The vapor may be pure vapor or may contain non-vaporizable elements as well. The vapor or other non-vaporizable elements may be medicine, therapeutic materials, material for promoting or protecting wellness, aromatherapy materials, or substances for recreational use, e.g., psychoactive substances, flavorings or odors for entertainment purposes, or for enhancing a virtual reality simulation. The device 1420 may also test ambient air to make sure it is in compliance with safety, medical and generally needed or desired guidelines.

The system 1400 and device 1420 may be instantly, remotely or self-powered via a battery or self-powering mechanism, such as a solar cell, hand crank, fuel cell, electrochemical cell, wind turbine and the like. For example, a portable device may include a battery or other power source 1408 capable of off-the-grid power, or may be connected to an external power source. The device 1420 may further include a self-calibration system utilizing a base of molecular sensing levels associated with a specific set of vapor intake cartridges utilized specifically for the calibration of the device. Such calibration cartridges may be installed in the inlet of the suction mechanism 1405, replacing the personal vaporizer 1412, or in a different inlet. These vapor calibration cartridges may be manufactured to output specified and calibrated concentrations on specific substances when exposed to a specific suction profile of the Vape-Bot 1420. Thus, such cartridges may be used to calibrate the sensor capabilities of the Vape-Bot 1420 and verify sensor readings by the device. Readings by the device 1420 that do not meet the known levels of the test vapor cartridge may be used to indicate a need to repair, replace or recalibrate sensor equipment via the sensor grid, mass spectrometry equipment and database veracity.

The Vape-Bot 1420 may include a gas chromatograph and mass spectrometer (GC-MS) that includes a gas chromatograph with its output coupled to an input of the mass spectrometer (not shown). Further details of a GC-MS adapted for use in the Vape-Bot are provided below in connection with FIG. 15. After the vapor being analyzed by the device is ionized and separated via exposure to charging fields the results may then be correlated against existing results in a database local to the device 1420, or the results may be transmitted for correlating against a remote database server. A remote server 1406 may then transmit 1407 the result back to at least one of the device 1420, or any authorized third party device(s) or a user interface instant to the primary device. Additionally, at any point in an ionization process or any other spectrometry process configured inside the device 1420 where measurement data may be capable of providing a useful result via extrapolation, then at least one of visual images along with hard data of the results of the spectrometry may be captured and analyzed instantly to correlate a result against a local database or transmitted for the same purpose.

Multiple robotic vapor devices 1420 in use for testing of pharmaceuticals, nutraceuticals, herbs, flavorings, supplements or foods may share data to view normalized aggregate levels, aggregate, store and analyze data, while refining and creating state of art the testing and analysis protocols as a result of viewing best practices and results. In addition, statistical data regarding characteristics and qualities of these consumables may thus be collected and used for diverse beneficial purposes.

Accordingly, aspects of the disclosure concern a system, method and device including a robotic pharmaceutical testing device, where the device functions also as a remote data sharing device. In an aspect, the device utilizes mass spectrometry to analyze a sample material, for example a pharmaceutical, nutraceutical, herb, flavoring, supplement or food. In another aspect, data analysis of the samples obtained from the RVD via mass spectrometry may be performed in at least one of the instant device or a remote device. For example, where the data analysis performed at least one of locally or remotely via correlative database, an analysis result may be transmitted back to the at least one of the RVD, an interface instant to the RVD, an authorized third party device or the like.

In other aspects, a system, method and device including an RVD may be used for sample conditioning. In such embodiments, an RVD may formulate conditioning data based upon at least one of a default setting, a remote authorized order, results of a real time or archival data analysis and system rules. The RVD may apply such control sources or parameters to determine customized sample conditioning processes for a coupled sample conditioning device, for example, a coupled vaporizer device. An RVD and a detachable vaporizer coupled to the RVD may coordinate operation by communication between connected processors, to provide the same or similar output as an RVD with vaporization capabilities. A system of multiple RVDs may share data with each other and with at least one central or sub central database. The shared data or analyzed data may be used to alter settings of at least one networked device, e.g., any one of the multiple RVD's or any sample conditioning device coupled to it.

Figure 15:
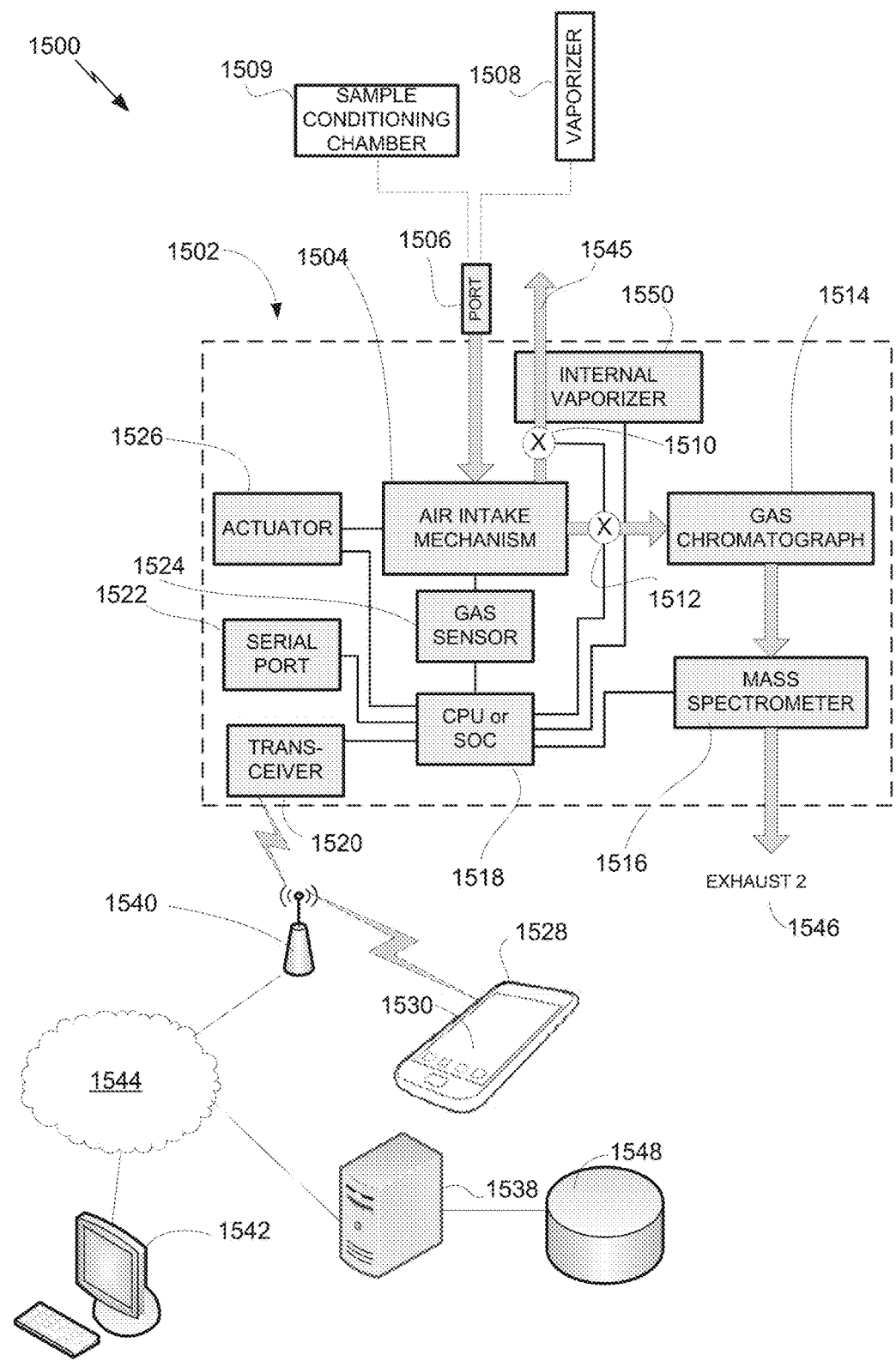
FIG. 15 is a schematic diagram illustrating alternative aspects of an analysis device for analyzing prescription medications.

Referring to FIG. 15, alternative or additional aspects of a system 1500 for testing of a personal vapor device are illustrated. The system 1500 may include an assembly 1502, also called a pharmaceutical testing apparatus (or called a chemical analysis device), which may be enclosed in a housing of portable form factor. The assembly 1502 may include a suction mechanism configured to draw an output from a sample conditioning device 1509 (for example a personal vaporizer 1508) placed in an inlet port 1506 of the assembly 1502. Moreover, the assembly 1502 may include a suction mechanism configured to draw an on output into/through an analysis chamber 1403 (FIG. 14) in which gas, vapor, smoke and/or the like emitted from a prescription medication or other test material are analyzed using one or more sensor circuits. The air intake mechanism 1504 may be, or may include, a variable volume, variable speed mechanism, for example, a variable-volume piston pump, variable expansion bellows or variable speed gas pump. The air intake 1504 may be in fluid communication with at least one of a chemical testing assembly (1524 or 1514/1516), an exhaust port to ambient air (1545 or 1546), or a network communication device (1520 or 1522).

The pharmaceutical testing apparatus 1502 may further include a processor 1518, for example, a central processing unit (CPU) or system on a chip (SOC) operatively coupled to at least one of the air intake mechanism 1504, the chemical testing assembly (1524 or 1514/1516), or the network communication device (1520 or 1522). As illustrated, the processor 1518 is communicatively coupled to all three of the air intake mechanism 1504, the chemical testing assembly (1524 or 1514/1516), or the network communication device (1520 or 1522). The processor may comprise an analysis module and a communication module, as will be discussed further herein with reference to FIG. 16. The analysis module of the processor may be operatively coupled to the chemical testing assembly (1524 or 1514/1516) while the communications module may be operatively coupled to the network communication device (1520 or 1522). The coupling to the air intake mechanism 1504 is via an actuator 1526, for example a motor, and may include other components as known in the art, for example a motor driving circuit.

For embodiments of the assembly 1502 that include the chemical testing assembly (1524 and/or 1514/1516), the processor may be further configured to receive measurement data from the chemical testing assembly via a communications module of the processor. The chemical testing assembly may include at least one of a gas sensor circuit 1524, or a GC/MS assembly 1514, 1516.

The processor 1518 may be configured to perform at least one of analyzing the measurement data by an analysis module of the processor 1518, sending the measurement data to a network node 1528 (e.g., a smartphone, notepad computer, laptop computer, desktop computer, server, etc.), or receiving an analysis of the measurement data from the network node 1528. Accordingly, the pharmaceutical testing apparatus 1502 may further include a user interface port 1522 or 1520, wherein the processor is configured to determine a material to be measured based on an input from the user interface port. The user interface port may comprise a wired interface, for example a serial port 1522 such as a Universal Serial Bus (USB) port, an Ethernet port, or other suitable wired connection. The user interface port may comprise a wireless interface, for example a transceiver 1522 using any suitable wireless protocol, for example Wifi (IEEE 802.11), Bluetooth™, infrared, or other wireless standard. The user interface port may be configured to couple to at least one of a vaporizer 1508 or a mobile computing device 1528, and either of these 1508, 1528 may include a user interface for receiving user input. For example, a mobile computing device 1528 may include a touchscreen 1530 for both display output and user input.

The processor 1518 may be configured to activate a gas or vapor sensor circuit based on the material to be measured. For example, a user may indicate that formaldehyde is of particular concern, via a user interface 1530 of the mobile device 1528. In response to this input, the processor may activate an electrochemical or other sensor circuit that is specialized for sensing formaldehyde. This may include opening a valve 1510 to exhaust via a first exhaust port 1546 bypassing the GC/MS components 1514, 1516. In an alternative, or in addition, the processor 1518 may activate the GC/MS components 1514, 1516, including closing the first exhaust valve 1510 and opening a second valve 1512 leading to the GC 1514 and MS 1516 to a second exhaust 1546. A filter component may be interposed between the GC 1514 and suction mechanism 1504 (or sample chamber) to prevent non-gaseous products from fouling the GC component 1514.

In an aspect, the suction mechanism 1504 further comprises at least one of a variable stroke piston, variable stroke bellows, or a rotary gas pump or fan. The mechanism 1504 may include a sample analysis chamber; for example, the cylinder of a piston pump may double as a sample chamber, with sensors embedded in a cylinder end. In an alternative, or in addition, the pump mechanism 1504 may be in fluid communication with a separate analysis chamber (not shown). The mechanism 1504 may further be configured to draw air or vapor at a variable rate. For example, the suction mechanism 1504 may be configured to draw air into an interior volume at a rate controlled at least in part by the processor 1518. In further embodiments a prescription medication may be placed in the interior volume of the sample chamber 1509, and air drawn into the sample chamber 1509 passing over/through the prescription medication.

The pharmaceutical testing apparatus 1502 may include at least one of an internal vaporizer (not shown) or a control coupling (e.g., via a connector in port 1506 or via a wireless coupling) to a sample conditioning chamber 1506, which for example may be, or may include, a detachable vaporizer 1508 for personal use, or a specialized conditioning chamber. The processor 1518 may be configured to control vapor output of at least one of the internal vaporizer 1550 or the detachable vaporizer 1508. In various embodiments, the internal vaporizer 1550 may be combined with, or coupled to, the sample conditioning chamber 1509 and used in sample conditioning. For example, the internal vaporizer 1550 may be used to heat the sample under test and/or to expose the sample to a known reactant, catalyst, diluent, solvent, or other reagent. When used for sample conditioning, an exhaust port 1545 of the internal vaporizer may be coupled to the input port 1506, using tubing or the like (not shown). In an aspect, the tubing may be removable so that the vaporizer 1550 can be used for treating room air, when desired, by coupling the exhaust 1545 to an ambient environment.

In an aspect, the processor 1518 may be configured to control the vapor output of the vaporizer 1508 or an internal vaporizer 1550 for a defined vapor concentration target in a sample chamber 1509 or other confined space, over a defined period of time. For example, a defined concentration of a reagent for a substance under test may be targeted, with real-time feedback analyzed and used for control via the assembly's gas sensing circuits 1524, 1514/1516. Thus, the pharmaceutical testing apparatus may be used as a feedback controlled or open-loop controlled vapor dispensing device for the sample chamber; or by coupling to different space, even for a room or other confined space. In any case, the processor may be configured to control the vapor output based on at least one of a default setting, a remote authorized order, current measurement data, archived measurement data, system rules, or a custom formulation of multiple vaporizable materials, in addition to, or instead of, feedback data.

In related aspects, the vaporizer 1550 (or 1508) may be coupled to one or more containers containing a vaporizable material, for example a fluid. For example, coupling may be via wicks, via a valve, or by some other structure. The coupling mechanism may operate independently of gravity, such as by capillary action or pressure drop through a valve. The vaporizer may be configured to vaporize the vaporizable material from one or more containers at controlled rates, and/or in response to suction applied by the assembly 1502, and/or in response to control signals from the assembly 1502. In operation, the vaporizer 1508 may vaporize or nebulize the vaporizable material, producing reagent aerosol or vapor. In embodiments, the vaporizer may include a heater coupled to a wick, or a heated wick. A heating circuit may include a nickel-chromium wire or the like, with a temperature sensor (not shown) such as a thermistor or thermocouple. Within definable limits, by controlling suction-activated power to the heating element, a rate of vaporization may be controlled. At minimum, control may be provided between no power (off state) and one or more powered states. Other control mechanisms may also be suitable.

The processor 1518 may be coupled to any one or more of the vaporizers 1550, 1508 via an electrical circuit, configured to control a rate at which the vaporizer 1550, 1508 vaporizes the vaporizable material. In operation, the processor 1518 may supply a control signal to the vaporizer 1550, 1508 that controls the rate of vaporization. A transceiver port 1520 is coupled to the processor, and the processor may transmit data determining the rate to a receiver on the detachable vaporizer 1508. Thus, the vaporization rate of the detachable vaporizer 1508 may be remotely controllable from the assembly 1502, by providing the data.

The processor 1518 may be, or may include, any suitable microprocessor or microcontroller, for example, a low-power application-specific controller (ASIC) designed for the task of controlling a vaporizer as described herein, or (less preferably) a general-purpose central processing unit, for example, one based on 80×86 architecture as designed by Intel™ or AMD™, or a system-on-a-chip as designed by ARM™, or a custom-designed system-on-a-chip optimized for gas analysis and other operations of the assembly 1502 as described. The processor 1518 may be communicatively coupled to auxiliary devices or modules of the vaporizing apparatus 1502, using a bus or other coupling. Optionally, the processor 1518 and some or all of its coupled auxiliary devices or modules may be housed within or coupled to a housing substantially enclosing the suction mechanism 1504, the processor 1518, the transceiver port 1520, and other illustrated components.

The assembly 1502 and housing may be configured together in a form factor of an friendly robot, a human bust, a sleek electronic appliance, or other desired form. For instance, the assembly 1502 (and/or the chemical analysis device alone or together with the entire assembly 1502) may be a component of at least one of a Vape-Bot™, a microvapor device, a vapor pipe, an e-cigarette, an e-cigar, a hybrid handset and vapor device and/or the like. Thus, one may appreciate that a joint analysis and consumption apparatus may be provided where the chemical analysis device performs chemical analysis of the prescription medication at the point of consumption of the prescription medication by a user and/or the point of diffusion of the smoke, vapor, fluid, offgas, and/or the like of the prescription medication into an airspace and/or consumption by a user. In various embodiments, the chemical analysis device inhibits operation of the joint analysis and consumption apparatus such as in response to a quantity of an impurity exceeding a stored first impurity threshold.

In related aspects, the assembly 1502 includes a memory device (not shown) coupled to the processor 1518. The memory device may include a random access memory (RAM) holding program instructions and data for rapid execution or processing by the processor during control of the assembly 1502. When the assembly 1502 is powered off or in an inactive state, program instructions and data may be stored in a long-term memory, for example, a non-volatile magnetic, optical, or electronic memory storage device (also not shown). Either or both of the RAM or the storage device may comprise a non-transitory computer-readable medium holding program instructions, that when executed by the processor 1518, cause the apparatus 1502 to perform a method or operations as described herein. Program instructions may be written in any suitable high-level language, for example, C, C++, C#, or Java™, and compiled to produce machine-language code for execution by the processor. Program instructions may be grouped into functional modules, to facilitate coding efficiency and comprehensibility. It should be appreciated that such modules, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. In other words, the modules may be high-level modules only.

In a related aspect, the processor 1518 may receive a user identifier associated with the apparatus 1508 and/or mobile computing device 1528 and store the user identifier in a memory. A user identifier may include or be associated with user biometric data, that may be collected by a biometric sensor or camera included in the assembly 1502 or in a connected or communicatively coupled ancillary device 1528, such as, for example, a smart phone executing a vaporizer interface application. The processor 1518 may generate data indicating a quantity of the vaporizable material tested or consumed by any one of the vaporizers 1550, 1508 in a defined period of time, and save the data in the memory device. The processor 1518 and other electronic components may be powered by a suitable battery, as known in the art, or other power source.

The apparatus 1502 may include a gas chromatograph and mass spectrometer (GC-MS) that includes a gas chromatograph 1514 with its output coupled to an input of the mass spectrometer 1516 and then to an exhaust 1546. The gas chromatograph may include a capillary column which depends on the column's dimensions (length, diameter, film thickness) as well as the phase properties (e.g. 5% phenyl polysiloxane). The difference in the chemical properties between different molecules in a mixture and their relative affinity for the stationary phase of the column will promote separation of the molecules as the sample travels the length of the column. The molecules are retained by the column and then elute (come off) from the column at different times (called the retention time), and this allows the mass spectrometer downstream to capture, ionize, accelerate, deflect, and detect the ionized molecules separately. The mass spectrometer does this by breaking each molecule into ionized fragments and detecting these fragments using their mass-to-charge ratio. These and other details of the GC/MS may be as known in the art.

The gas sensor circuit 1524 may include an array of one or more as sensors, any one or more of which may be independently controllable and readable by the processor 1518. Any one or more of the sensors of the array may be, or may include, an electrochemical sensor configured to detect an electrical signal generated by a chemical reaction between a component of the sensor and the gas analyte. Any one or more of the sensors of the array may be, or may include, a carbon nanotube sensor, which may be considered a variety of electro chemical sensor. Many different electrochemical sensors are known in the art for detecting specific materials. Any one or more of the sensors of the array may be, or may include, an infrared absorption sensor that measures an amount of absorption of infrared radiation at different wavelengths. Any one or more of the sensors of the array may be, or may include, a semiconductor electrochemical sensor, which changes semi conductive properties in response to a chemical reaction between a component of the sensor and an analyte. Any other suitable gas or vapor sensor may be user. The gas sensor circuit 1524 may also include gas sensors of other types, for example, optical sensors for measuring vapor density, color or particle size, temperature sensors, motion sensors, flow speed sensors, microphones or other sensing devices.

In related aspects, the assembly may include a transmitter port 1520 coupled to the processor. The memory may hold a designated network address, and the processor 1518 may provide data indicating measurement data of vapor or other material analyzed, or amount of material emitted by the vaporizer to the sample chamber, an identity of the material under test, if known, and related information, to the designated network address in association with the user identifier, via the transmitter port 1520.

An ancillary device, such as a smartphone 1528, tablet computer, or similar device, may be coupled to the transmitter port 1514 via a wired coupling 1522 or wireless coupling 1520. The ancillary device 1528 may be coupled to the processor 1518 for providing user control input to a gas measurement or vaporizer control process operated executing on the processor 1518. User control input may include, for example, selections from a graphical user interface or other input textual or directional commands) generated via a touch screen 1530, keyboard, pointing device, microphone, motion sensor, camera, or some combination of these or other input devices, which may be incorporated in the ancillary device 1528. A display 1530 of the ancillary device 1528 may be coupled to a processor therein, for example via a graphics processing unit (not shown) integrated in the ancillary device 1528. The display 1530 may include, for example, a flat screen color liquid crystal (LCD) display illuminated by light-emitting diodes (LEDs) or other lamps, a projector driven by an LED display or by a digital light processing (DLP) unit, or other digital display device. User interface output driven by the processor 1518 may be provided to the display device 1530 and output as a graphical display to the user. Similarly, an amplifier/speaker or other audio output transducer of the ancillary device 1528 may be coupled to the processor 1518 via an audio processing system. Audio output correlated to the graphical output and generated by the processor 1518 in conjunction with the ancillary device 1528 may be provided to the audio transducer and output as audible sound to the user.

The ancillary device 1528 may be communicatively coupled via an access point 1540 of a wireless telephone network, local area network (LAN) or other coupling to a wide area network (WAN) 1544, for example, the Internet. A server 1538 may be coupled to the WAN 1544 and to a database 1548 or other data store, and communicate with the apparatus 1502 via the WAN and coupled device 1528. In alternative embodiments, functions of the ancillary device 1528 may be built directly into the apparatus 1502, if desired. Functions or data of the apparatus 1502 and/or system 1500 may also be accessed or controlled via a client terminal (e.g., personal computer) 1542.

Figure 16:
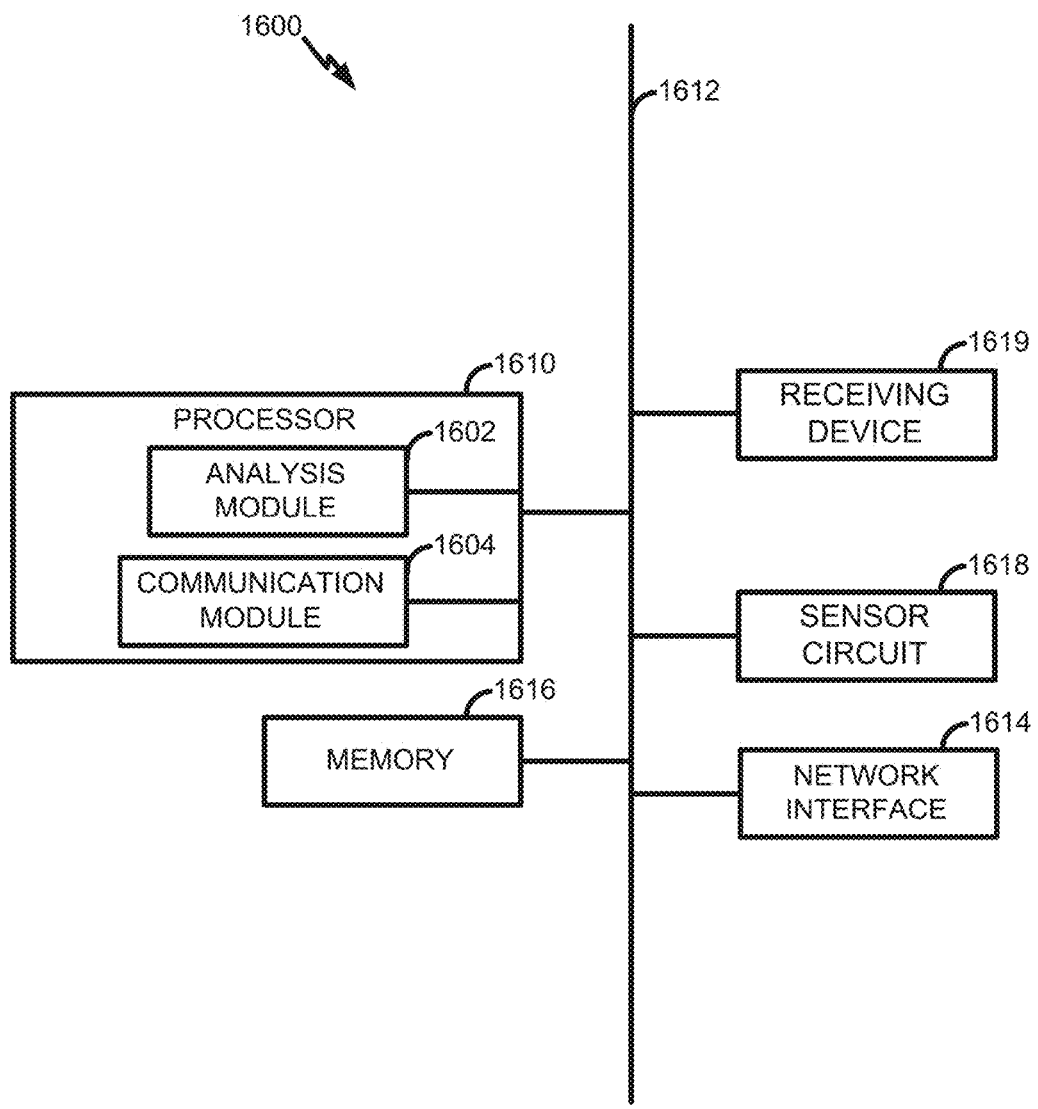
FIG. 16 is a block diagram illustrating components of an apparatus or system for analyzing prescription medications.

FIG. 16 is a block diagram illustrating components of an apparatus or system 1600 for analyzing prescription medications, in accord with the foregoing examples. The apparatus or system 1600 may include additional or more detailed components as described herein. For example, the processor 1610 and memory 1616 may contain an instantiation of a controller for an MID as described herein. As depicted, the apparatus or system 1600 may include functional blocks that can represent functions implemented by a processor, software, or combination thereof (e.g., firmware).

As illustrated in FIG. 16, the apparatus or system 1600 may comprise a component 1619 for receiving, by a testing assembly, at least one of smoke, vapor, liquid, solid, or gas from a prescription medication into the testing assembly. The component 1602 may be, or may include, a means for the receiving, for example, a sample chamber with or without a coupled vaporizer, or, personal vaporizer, or a suction mechanism, each of the foregoing as described above.

The apparatus or system 1600 may further include an electrical component or module 1602 for analysis of a sample, including a prescription medication or the like, for example. Said means may include the processor 1610 comprising an analysis module 1602. The processor 1610 may be coupled to the memory 1616, and to the network interface 1614 (via the communication module 1604) and a gas sensor circuit 1618 or GC/MS equipment (via the analysis module 1602), the processor executing an algorithm based on program instructions stored in the memory. Such algorithm may include a sequence of more detailed operations, for example, activating a sensor circuit, receiving measurement data from the circuit, and comparing the measurement data from the circuit to characteristic data from a database or the like. The algorithm may include other, more detailed operations, for example as described in herein.

The apparatus or system 1600 may further comprise an electrical component 1604 for transmitting analysis data characterizing the prescription medication, in response to the analyzing. The component 1604 may be, or may include, a means for transmitting or otherwise electronically communicating analysis data characterizing the prescription medication, in response to the analyzing. Said means may include the processor 1610 coupled to the memory 1616, and to the network interface 1614, the processor executing an algorithm based on program instructions stored in the memory. Such algorithm may include a sequence of more detailed operations, for example, receiving a send instruction, preparing a data packet at an application layer, providing the packet to a lower communication layer, and waiting to receive a response packet.

The apparatus 1600 may include a processor module 1610 having at least one processor, in the case of the apparatus 1600 configured as a controller configured to operate sensor circuit 1618 and receiving device 1619 and other components of the apparatus. The processor 1610, in such case, may be in operative communication with the memory 1616, interface 1614 or dispenser/vaporizer 1618 via a bus 1612 or similar communication coupling. The processor 1610 may effect initiation and scheduling of the processes or functions performed by electrical components 1602-1604.

In related aspects, the apparatus 1600 may include a network interface module operable for communicating with a server over a computer network. The apparatus may include a sensor network 1618 for sensing a vaporizable material, for example, one or more of the sensors described herein above, or a GC/MS system. The apparatus may include a receiving device 1619, as described herein above, for conditioning a sample and drawing an emitted material from a sample chamber or the like. In further related aspects, the apparatus 1600 may optionally include a module for storing information, such as, for example, a memory device/module 1616. The computer readable medium or the memory module 1616 may be operatively coupled to the other components of the apparatus 1600 via the bus 1612 or the like. The memory module 1616 may be adapted to store computer readable instructions and data for enabling the processes and behavior of the modules 1602-1604, and subcomponents thereof, or of the methods disclosed herein. The memory module 1616 may retain instructions for executing functions associated with the modules 1602-1604. While shown as being external to the memory 1616, it is to be understood that the modules 1602-1604 can exist within the memory 1616.

Figure 17:
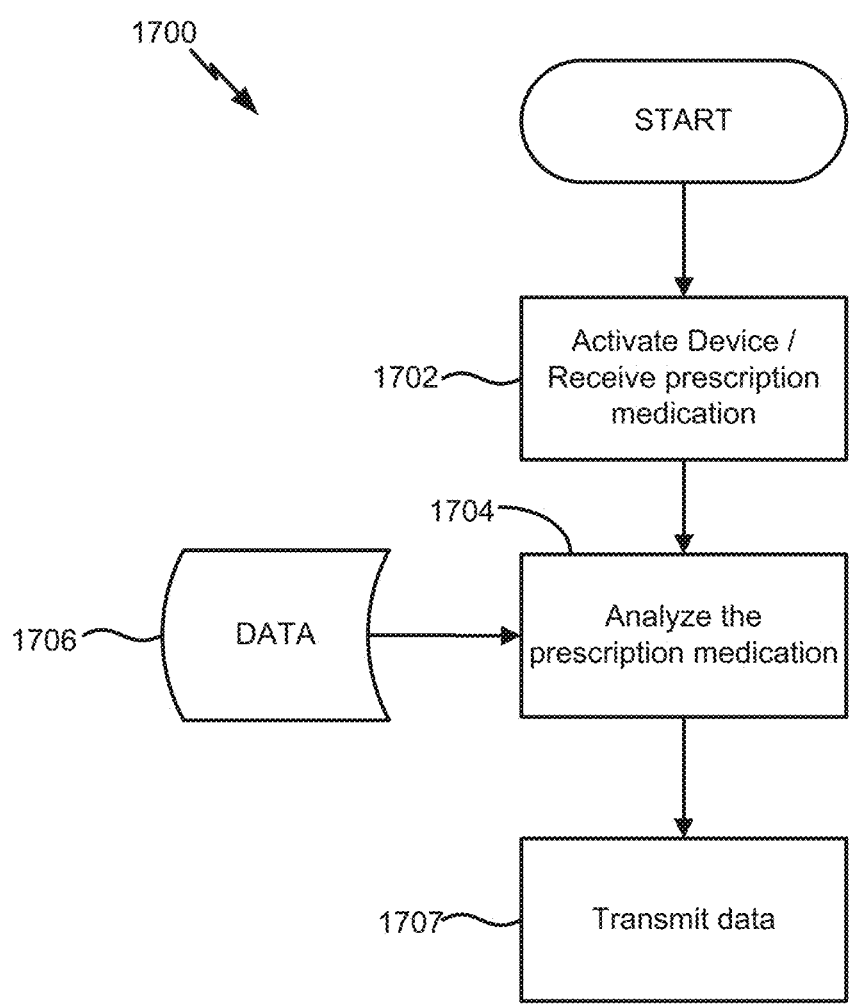
FIG. 17 illustrates an exemplary method.

An example of a control and analysis algorithm (e.g., method for analyzing prescription medication) 1700 is illustrated by FIG. 17, for execution by a processor of an RVD as described herein, which includes independently controllable gas sensor array and GC/MS equipment. The algorithm 1700 may be triggered by activation of the device at 1702, for example when a user places a vaporizer in an inlet port of the RVD and/or a biological sample in a sample chamber and activates a power-on switch or control. In other words, the method may include receiving, by a chemical testing assembly, at least one of smoke, vapor, fluid, solid, or offgas from a prescription medication into the chemical testing assembly. At 1704, the processor may obtain a set of test or measurement parameters, based on locally stored and/or remotely obtained data 1706, including for example (optionally) user identifier, past use records including inhalation patterns and materials used, and any relevant criteria. For example, for a new user with no past use who wants to test a vaporizer prior to purchase, the processor may select default median criteria and receive input via a user interface or the like concerning materials of concern to the prospective purchaser. For further example, for a known user with past use data, the processor may obtain inhalation patterns and materials of concern from a user profile stored on the vaporizer, in the RVD, and/or in another network node. Still further, if there is no test objective based on a user, such as if the RVD is to work in room air treatment mode only, the processor may select a use and measurement parameters specific for a specified desired room air treatment. The processor may further analyze by an analysis module of the processor operatively coupled to the chemical testing assembly the prescription medication.

At 1707, the processor transmits, by a communications module of the processor, data characterizing the prescription medication, in response to the analyzing of step 1704.

At any relevant point in the process, the processor may perform various additional operations, and/or control operations (in contrast to analysis operations). While the discussion above relates to analysis operations, the processor may also do control operations. For instance, such operations may be performed at steps 1704 and/or 1707, and may include the processor sending control data to an actuator for a suction mechanism, which causes the suction mechanism to draw a volume of a specified amount according to a specified flow rate. The flow rate for the draw may be constant or variable based on a rate curve.

Once a volume is drawn, or during the drawing simulated inhalation) process, the processor determines whether GC/MS is to be used for any analysis. The determination may be based on the measurement parameters obtained and/or otherwise determined at 1704.

If no GC/MS analysis is called for at 1704, the processor may receive data from a gas sensor array exposed to the gas analysis chamber that holds the indrawn vapor. For example, the processor may switch on one or more sensors of the sensor array, based on the measurement parameters, and read sensor data from any activated sensor circuits at one or more input pins. Sensor data may be digital, or may be converted by an A/D converter interposed between an analog sensor and the processor. In an alternative, an integrated sensor device may output a digital signal indicating a measurement value. The processor may use the sensor reading to derive an analysis result. The processor may transmit data characterizing the prescription medication, in response to the analysis results, such as at 1707.

Figure 18:
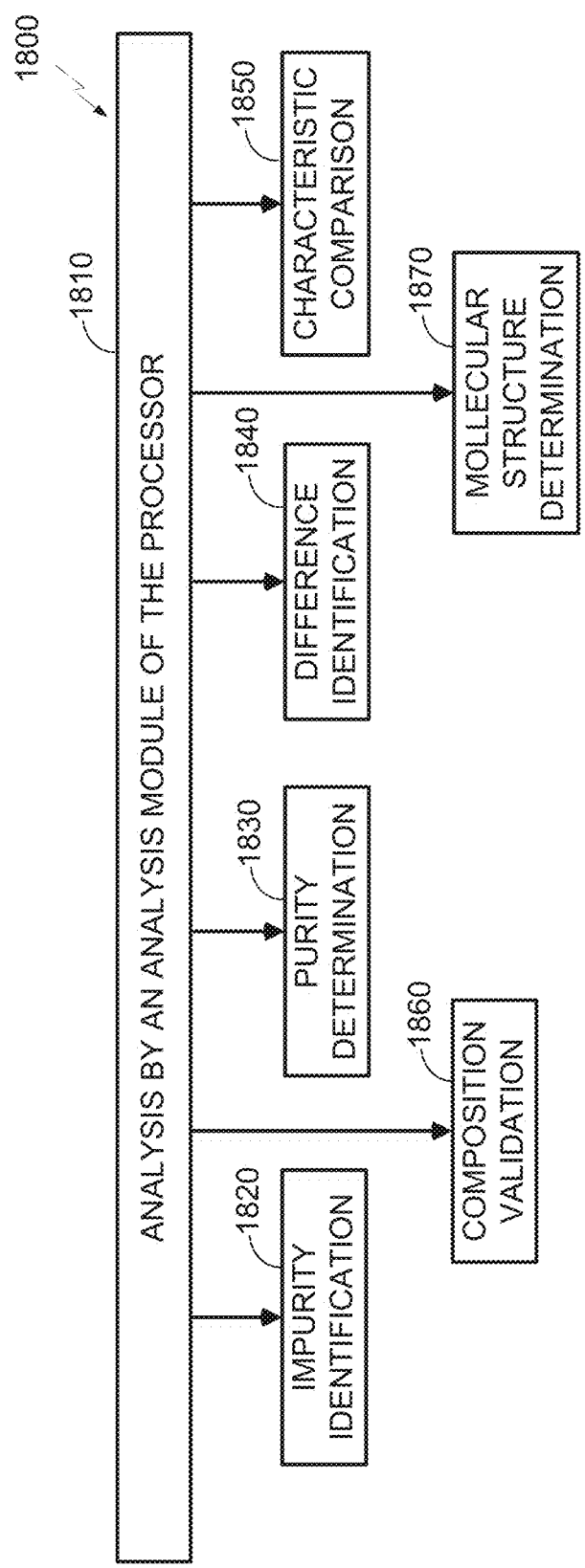
FIG. 18 illustrates an exemplary method.
Figure 19:
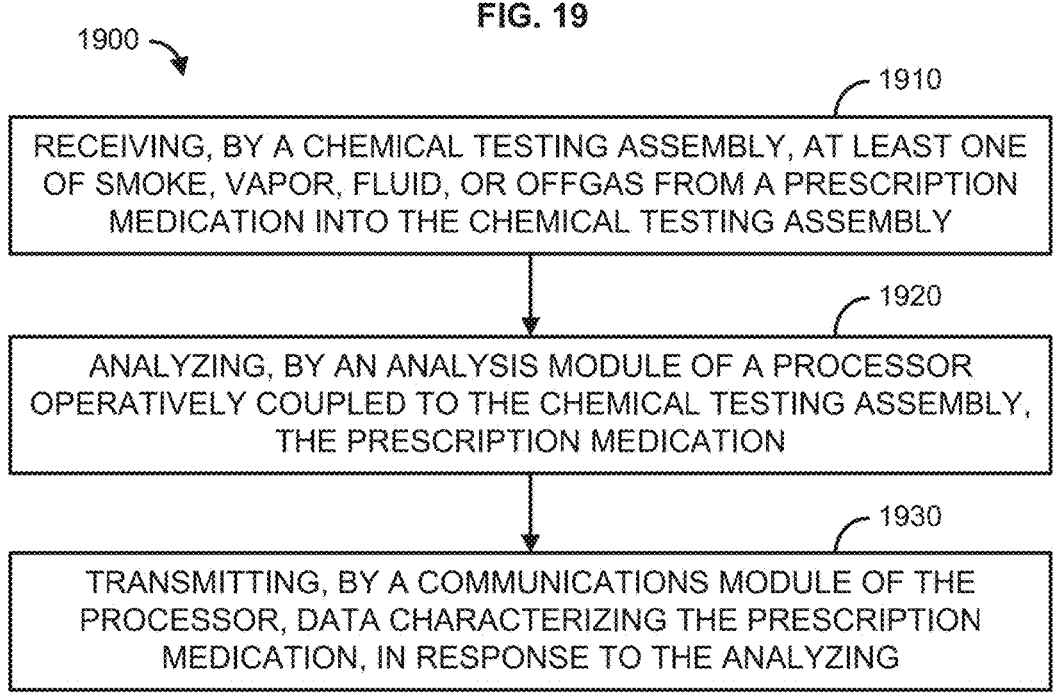
FIG. 19 illustrates an exemplary method.
Figure 20:
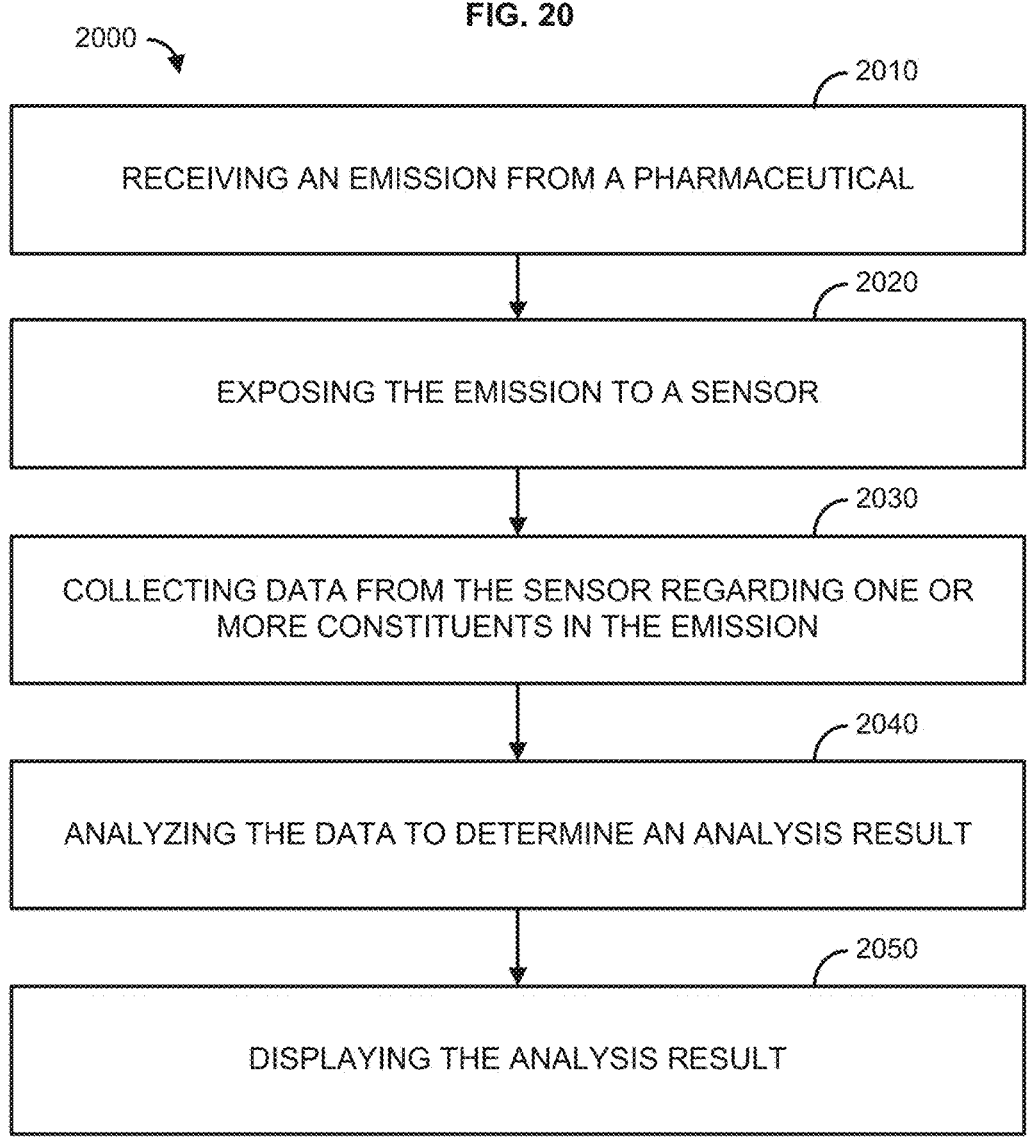
FIG. 20 illustrates an exemplary method.
Figure 21:
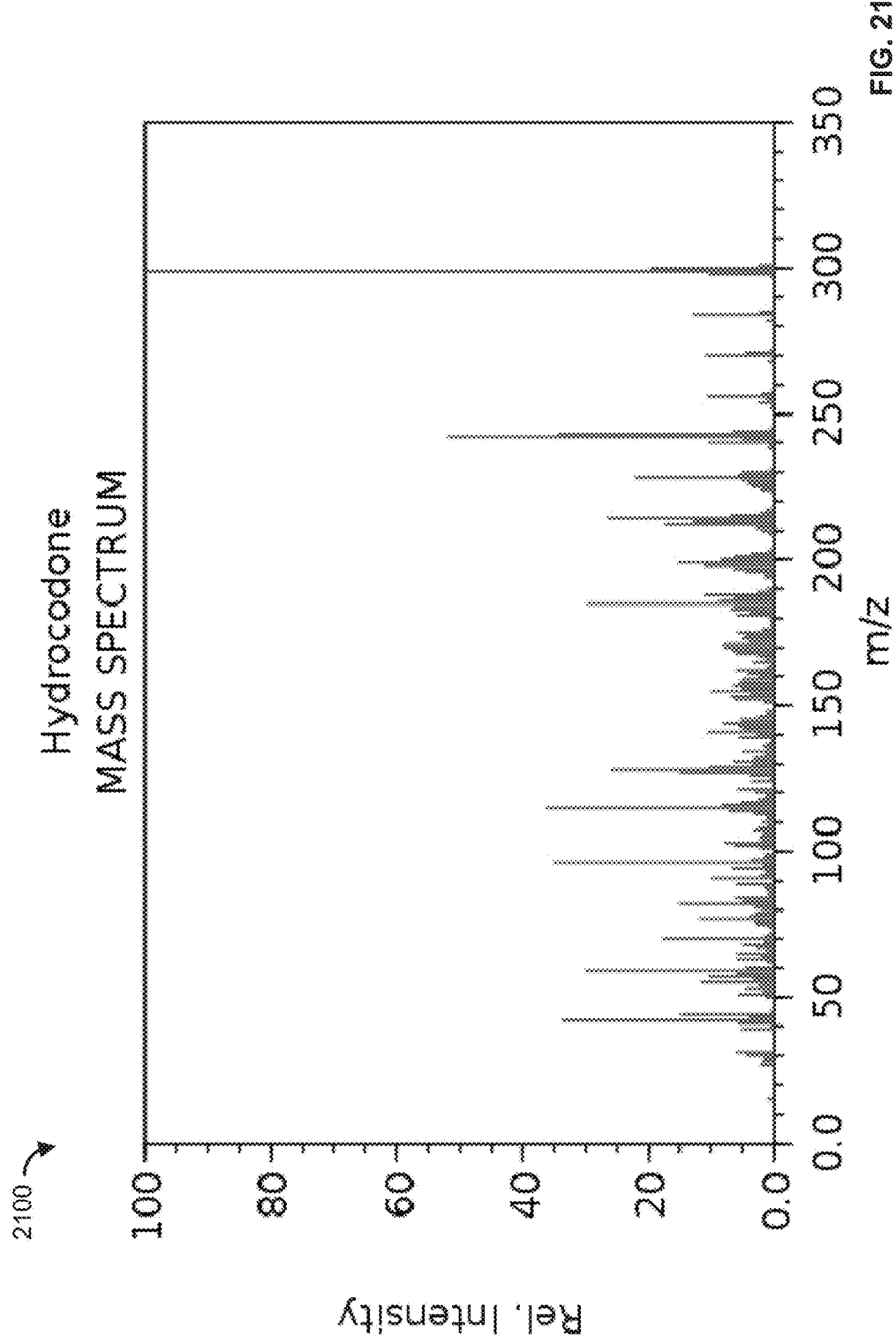
FIG. 21 illustrates an example chemical signature.
Figure 22:
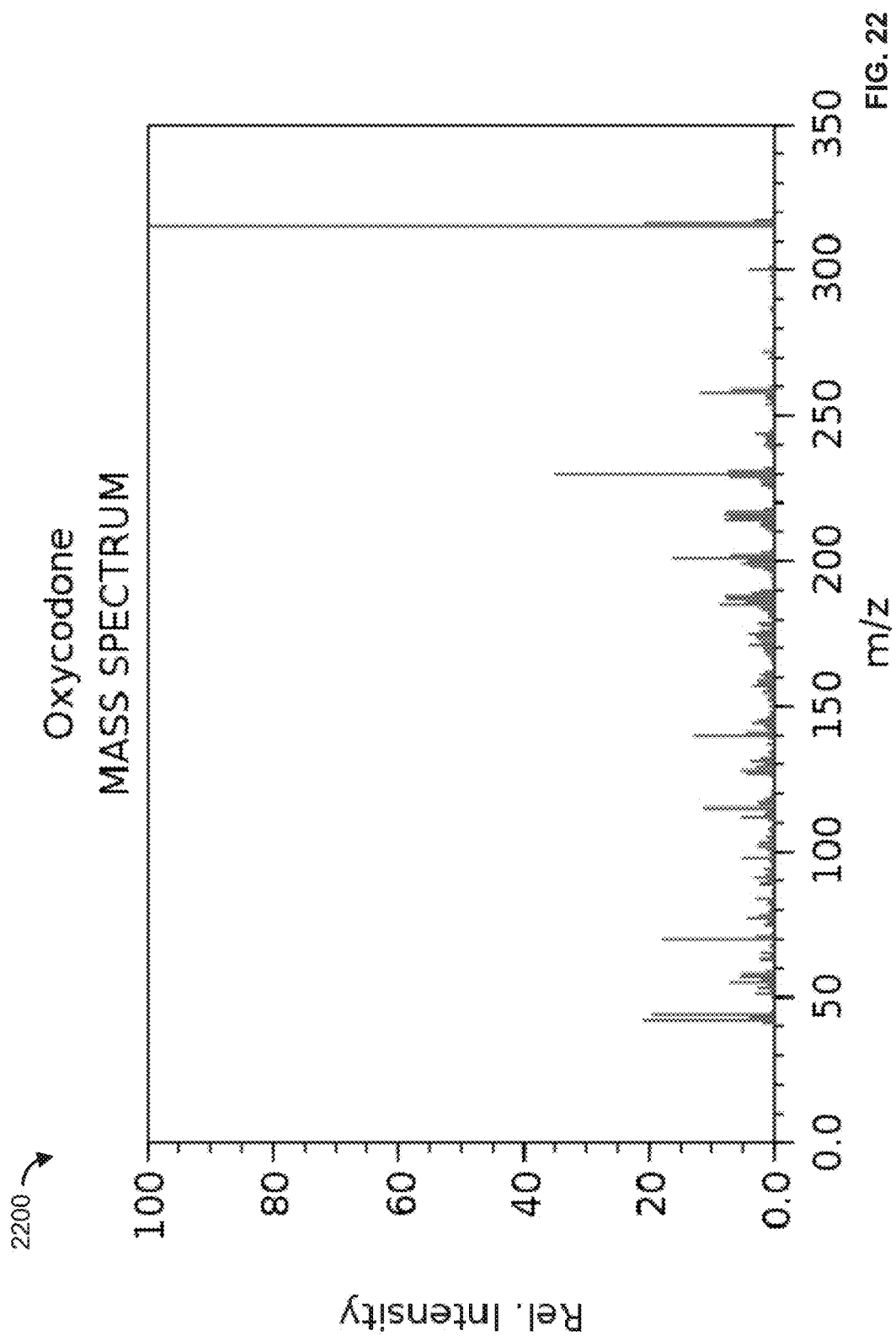
FIG. 22 illustrates an example chemical signature.
Figure 23:
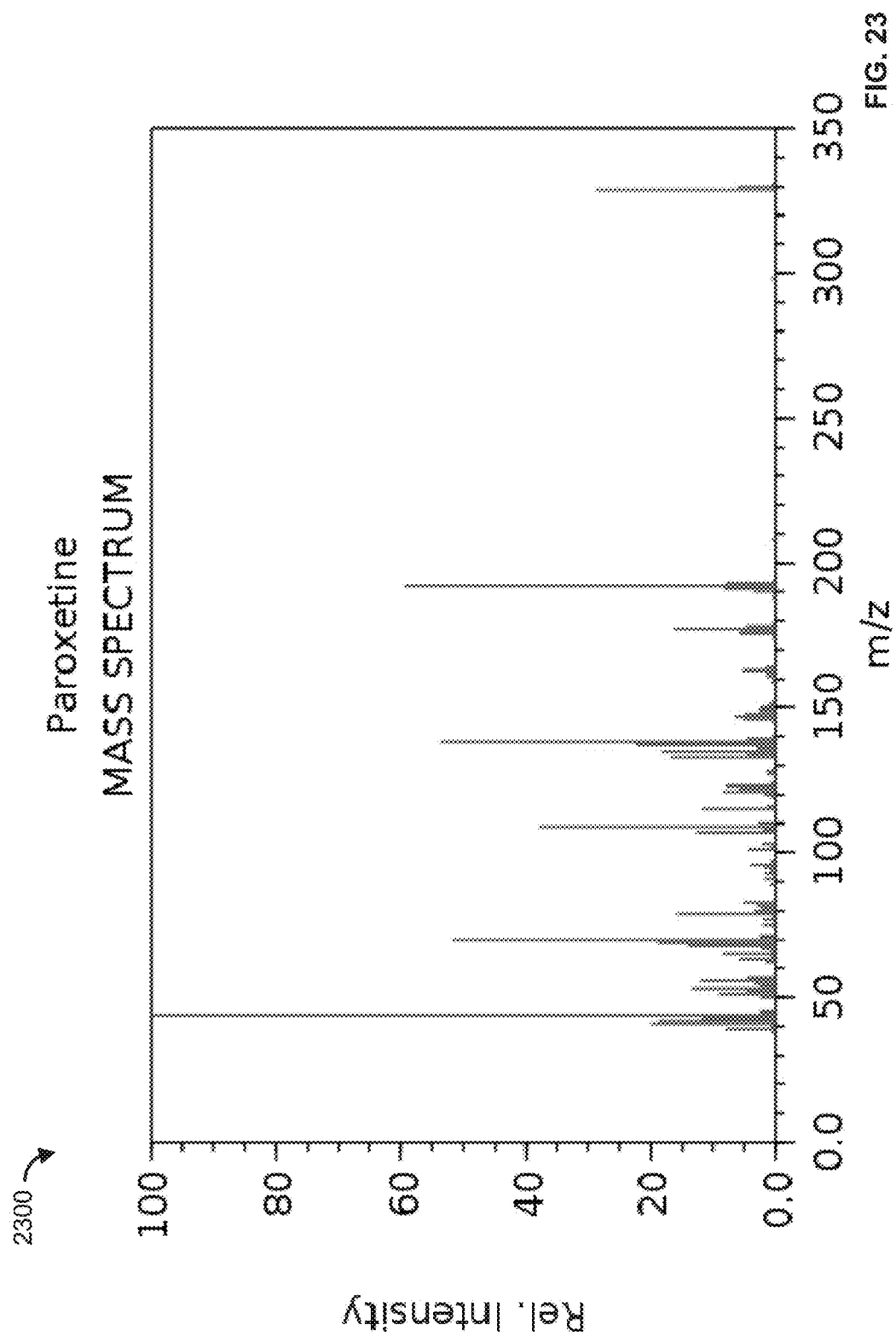
FIG. 23 illustrates an example chemical signature.
Figure 24:
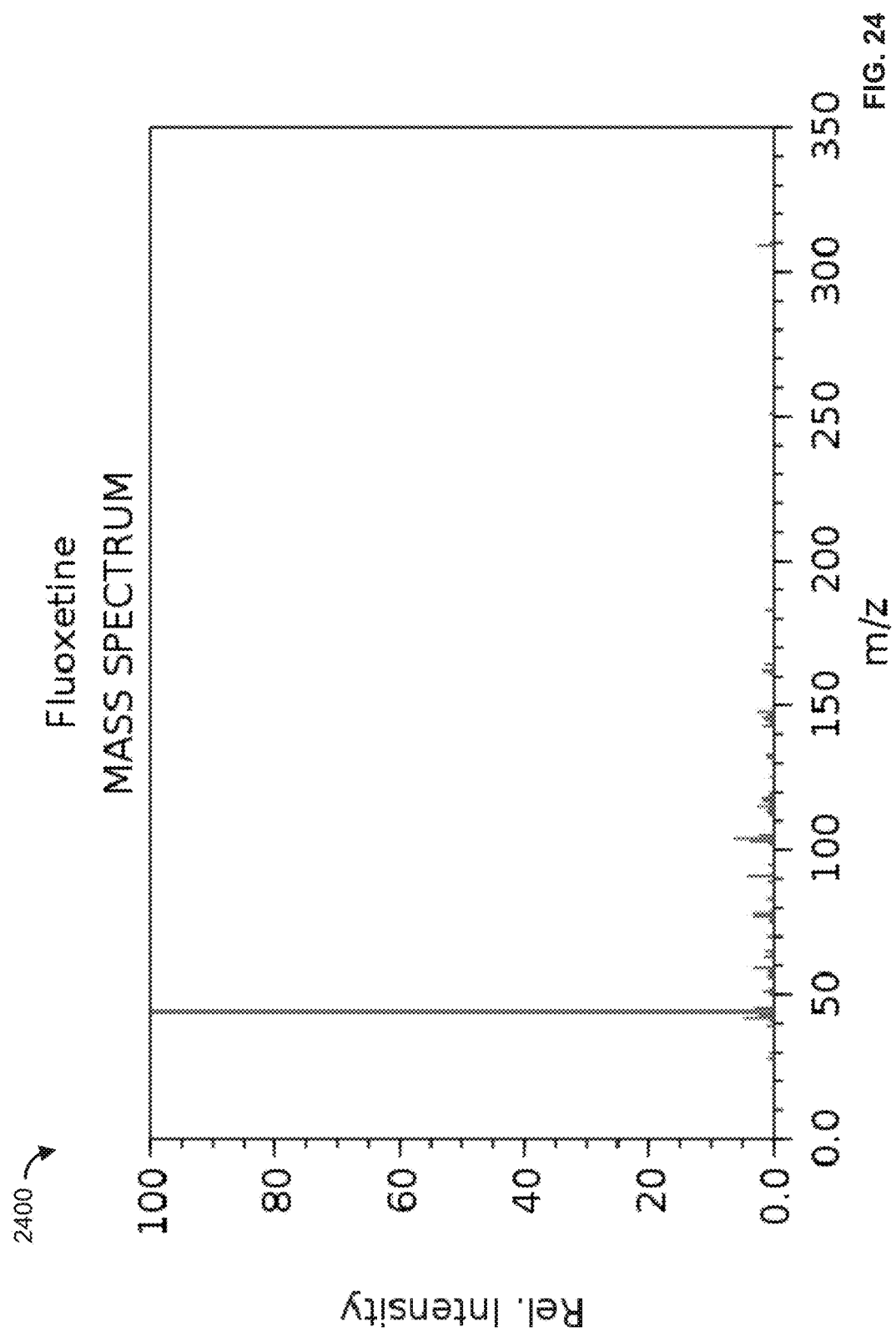
FIG. 24 illustrates an example chemical signature.

In view the foregoing, and by way of additional example, FIG. 18, FIG. 19, and FIG. 20 show aspects of a method or methods for controlling a vaporizer, as may be performed by a vaporizing device as described herein, alone or in combination with other elements of the systems and/or the methods disclosed. The vapor analysis device may include at least one gas sensing circuit, a suction mechanism, and a processor. Referring to FIG. 18, the method 1800 of analyzing the prescription medication, by an analysis module of a processor operatively coupled to the chemical testing assembly is disclosed in further detail.

The method 1800 may include an analysis 1810 by an analysis module of a processor of the prescription medication (such as by analysis of its vapor, fluid, offgas, smoke, and/or the like). The analysis may include sub steps 1820, 1830, 1840, 1850, 1860, 1870, and/or 1880, which may have further sub steps. In various embodiments, the analysis 1810 comprises evaluating, classifying, comparing, validating, refuting a prior classification of, and cataloging the prescription medication. This may produce analysis data including mass spectrometry, PH testing, genetic testing, particle and cellular testing, synthetic molecular analysis, sensor based testing, diagnostic testing, and/or wellness testing.

For instance, an analysis 1810 may include a step of impurity identification (step 1820). Impurity identification may comprise determining a quantity of a first impurity in the at least one of smoke, vapor, extracted fluid or offgas and may further comprise comparing the quantity of the first impurity to a stored first impurity threshold. Impurity identification may comprise determining an identity of a first impurity of the prescription medication. For instance; impurity identification may comprise determining whether a first impurity is lead, feces, fillers, cellulose, pathogens, placebo ingredients, and/or sugars. Impurity identification may comprise determining whether the prescription medication comprises a proper molecular element of the prescription medication in an unbalanced molecular form.

An analysis 1810 may include a step of purity determination (step 1830). Purity determination may comprise determining a purity of the prescription medication.

An analysis 1810 may include a step of difference identification (step 1840). Difference identification may include comparing characteristics of the product to a matching database of known characteristics of known prescription medications and determining at least a first difference between the product and at least one known prescription medication, wherein the analysis data comprises the first difference.

An analysis 1810 may include a step of characteristic comparison (step 1850). Characteristic comparison may include comparing characteristics of the product to a matching database of known characteristics of known prescription medications and matching the product to a known prescription medication, wherein the analysis data comprises a characteristic comparison.

An analysis 1810 may include a step of composition validation (step 1860). Composition validation may include identification of an identity of a prescription medication and a validation of a composition of a prescription medication.

An analysis 1810 may include a step of molecular structure determination (step 1870). Molecular structure determination may include a determination of a molecular structure of a prescription medication. For instance, wherein the device may further comprise an instant matching database of known characteristics of known prescription medications, and the molecular structure may be determined by comparing characteristics of the prescription medication to the instant matching database of known characteristics of known prescription medications. Moreover, the device may be operatively coupled by a network to a remote matching database of known characteristics of known prescription medications, and the molecular structure may be determined by comparing characteristics of the prescription medication to the remote matching database of known characteristics of known prescription medications.

Any step or substep may be performed independently, in any sequence, or in parallel with any other step or substep as desired. At various points during method 1800, such as at steps 1820, 1830, 1840, 1850, 1860, 1870, and/or 1880 and/or before, after, and/or between such steps, the processor may control a rate of operation of the suction mechanism. For example, the processor may control a speed at which a piston in a fixed or variable-volume piston pump is operated. For further example, the processor may control a rate at which a bellows is expanded, or the speed of a rotary air pump, or of any other type of air pump. For instance, in response to a determination that the amount of a impurity exceeds a stored first impurity threshold, the processor may stop the operation of the suction mechanism. In further embodiments, the suction mechanism is not stopped, but a user-readable warning is generated and indicated by at least one of a user interface device and a remote authorized system user device.

The gas sensing circuit, may measure at least one vapor constituent in a vapor drawn from a vaporizer by the suction mechanism.

Each of these various steps and sub steps may be performed in any operable order, and some steps and sub steps are not necessarily performed in every embodiment of the method, and the presence of any one of the step or substep does not necessarily require that any other of these additional operations also be performed.

The processor may receive measurement data from the gas sensing circuit. The processor may analyze the measurement data, or send the measurement data to a network node. The measuring may include at least one of gas chromatography, mass spectrometry, electrochemical detecting, carbon nanotube detecting, infrared absorption, or semiconductor electrochemical sensing.

With reference to both FIG. 17 and FIG. 18, the method 1700 may further include subsequent to steps 1704 and 1810, dispensing a vapor from the vaporizer via an exhaust of the suction mechanism. The processor may control the dispensing of the vapor output for obtaining a defined vapor concentration target in a confined space, including for example a sample condition chamber or ambient room space. The processor may determine a quantity of the vapor to dispense based on at least one of a default setting, a remote authorized order, current measurement data, archived measurement data, system rules, or a custom formulation of multiple vaporizable materials.

In another aspect, the method 1700 may include at 1702 drawing air into an interior volume at orate controlled at least in part by the processor. Thus, the apparatus may be used for regular or non-vaporized air sensing, for example as performed for environmental analysis. Accordingly, the method 1700 and 1800 may include, at 1704 and 1810, measuring, by the gas sensing circuit, at least one gaseous constituent in the air. The method 1700 may further include, at 1707, transmitting measurement data indicating a quantity of the gaseous constituent (in response to analysis step 1810 of method 1800) to a remote network node. Using a distributed network of like analyzers, environmental data may thereby be collected from a wide area and used for any desired purpose.

Finally, with reference to FIG. 19, a method 1900 of analyzing prescription medication in connection with various systems, methods, and devices disclosed herein is disclosed. The method 1900 may include receiving, by a chemical testing assembly, at least one of smoke, vapor, fluid, solid, or offgas from a prescription medication, into the chemical testing assembly (step 1910), analyzing, an analysis module of a processor operatively coupled to the chemical testing assembly, the prescription medication (step 1920), and transmitting, by a communications module of the processor, data characterizing the prescription medication, in response to the analyzing (step 1930). Various steps, substeps, systems, apparatuses, and the like may be incorporated into the method, and may interoperate with the method according to the teachings herein.

The analyzing further can comprise determining a quantity of a first impurity in the at least one of smoke, vapor, liquid, solid or gas. The analyzing can further comprise comparing the quantity of the first impurity to a stored first impurity threshold and wherein the method further can comprise indicating, by at least one of an user interface device and a remote authorized system user interface device, a user-readable warning in response to the quantity of the first impurity exceeding the stored first impurity threshold.

The transmitting can comprise at least one of transmitting data to a remote processor for at least one of analyzing, classifying, comparing, validating, refuting, and cataloging the material. The results of the analyzing can be returned for display by a user interface device.

The analyzing can comprise at least one of mass spectrometry, PH testing, genetic testing, particle and cellular testing, synthetic molecular analysis, sensor based testing, diagnostic testing, and wellness testing. The method can further comprising decarboxylating at least a portion of the prescription medication by the testing assembly, wherein the receiving can be in response to the decarboxylating.

The method can further comprise displaying, by a user interface device configured to display in response to the transmitting, at least one of: lighted signal lights, gauges, boxes, forms, check marks, avatars, visual images, graphic designs, lists, active calibrations or calculations, 2D interactive fractal designs, 3D fractal designs, 2D representation of a vapor device, 3D representation of the vapor device.

In an aspect, chemical analysis device for prescription medication is disclosed comprising a testing assembly configured to collect a product comprising at least one of smoke, vapor, liquid, solid, or gas from the prescription medication and a processor operatively coupled to the testing assembly and configured to analyze the collected product to determine an analysis result. The processor can be configured to analyze the product by at least one of evaluating, classifying, comparing, validating, refuting a prior classification of and cataloging the prescription medication. The processor can be configured to provide measurement data from the testing assembly to a remote processor, via a network and the analyzing can comprise receiving by the processor the analysis result from the remote processor. The testing assembly can provide measurement data by at least one of mass spectrometry, PH testing, genetic testing, particle and cellular testing, synthetic molecular analysis, sensor based testing, diagnostic testing, and wellness testing.

The chemical analysis device can further comprise a user interface device configured to display in response to the measurement data at least one of: lighted signal lights, gauges, boxes, forms, check marks, avatars, visual images, graphic designs, lists, active calibrations or calculations, 2D interactive fractal designs, 3D fractal designs, 2D representation of a vapor device, 3D representation of the vapor device. The chemical analysis device can further comprise a user interface display operatively coupled to the processor whereby at least one of the measurement data or the analysis result can be displayed.

The chemical analysis device can further comprise a remote authorized system user interface device operatively coupled to the processor by a network, wherein at least one of the measurement data or the analysis result can be displayed by the remote authorized system user interface device. The testing assembly can be a component of at least one of: a vapebot, a microvapor device, a vapor pipe, an e-cigarette, an e-cigar, a hybrid handset and vapor device.

The processor can be configured to analyze the product by comparing characteristics of the product to a matching database of known characteristics of known prescription medications and matching the product to a known prescription medication, wherein the analysis data can comprise a characteristic comparison. The processor can be configured to analyze the product by comparing characteristics of the product to a matching database of known characteristics of known prescription medications and determining at least a first difference between the product and at least one known prescription medication, wherein the analysis result can comprise the first difference. The chemical analysis device can further comprise a remote authorized system user interface device operatively coupled to the processor by a network, wherein at least one of the measurement data or the analysis result can be displayed by the remote authorized system user interface device. The analysis result can comprise an identification of an identity of a prescription medication and a validation of a composition of a prescription medication. The analysis data can comprise a determination of a molecular structure of a prescription medication. The chemical analysis device can further comprise a matching database of known characteristics of known prescription medications, wherein the molecular structure can be determined by comparing characteristics of the prescription medication to the instant matching database of known characteristics of known prescription medications. The chemical analysis device can be operatively coupled by a network to a remote matching database of known characteristics of known prescription medications, wherein the molecular structure can be determined by comparing characteristics of the prescription medication to the remote matching database of known characteristics of known prescription medications.

The analysis result can comprise a determination of a purity of the prescription medication. The analysis result can comprise a determination of the identity of a first impurity of the prescription medication. The first impurity of the prescription medication can comprise at least one of: lead, feces, fillers, cellulose, pathogens, placebo ingredients, and sugars. The first impurity of the prescription medication can comprise a proper molecular element of the prescription medication in an unbalanced molecular form.

In an aspect, an apparatus is disclosed comprising an intake, configured to receive an emission from a pharmaceutical, a sensor; coupled to the intake, configured for detecting one or more constituents in the emission, a processor, configured for, collecting data from the sensor regarding the one or more constituents, and analyzing the data to determine an analysis result, and a display device, coupled to the vaporizer component, configured for displaying the analysis result. The emission can comprise a particle, a smoke, a vapor, a fluid, or a gas.

The apparatus can further comprise an analysis chamber configured for causing the pharmaceutical to create the emission. The analysis chamber can be configured for one or more of, vaporizing the pharmaceutical, heating the pharmaceutical, cooling the pharmaceutical, or mechanically altering the pharmaceutical. The analysis chamber can be configured for decarboxylating the pharmaceutical. The sensor can comprise at least one of a gas chromatograph, a mass spectrometer, an electrochemical detector, a pH sensor, a genetic sensor, a carbon nanotube detector, an infrared absorption sensor, an optical image sensor, a particle or cell detector, a semiconductor electrochemical sensor, or a temperature sensor. The sensor can be further configured to detect one or more of, an identity of the one or more constituents, a type of the one or more constituents, a mixture of the one or more constituents, a temperature, a color, a concentration, a quantity, a toxicity, a pH, a vapor density, or a particle size.

Analyzing the data to determine an analysis result can comprise determining a molecular structure of the pharmaceutical. The analysis result can comprise a determination of a purity of the pharmaceutical. The analysis result can comprise a determination of an identity of an impurity of the pharmaceutical. The impurity of the pharmaceutical can comprise at least one of: lead, feces, fillers, cellulose, pathogens, placebo ingredients, and sugars. The impurity of the pharmaceutical can comprise a proper molecular element of the pharmaceutical in an unbalanced molecular form.

Analyzing the data to determine an analysis result can comprise determining a quantity of the impurity. Analyzing the data to determine an analysis result can comprise comparing the quantity of the impurity to a stored impurity threshold and displaying a warning in response to the quantity of the impurity exceeding the stored impurity threshold.

Analyzing the data to determine an analysis result can comprise determining a chemical signature of the emission based on the data and comparing the chemical signature to a database of chemical signatures. The processor can be further configured to store the chemical signature in the database as a new signature if the chemical signature is not found in the database of chemical signatures.

The apparatus can further comprise a network access device configured for transmitting the data to a computing device. The network access device can be further configured to receive the analysis result from the computing device. The processor can be configured for sharing data with a user interface device via the network access device. The user interface device can be configured to display a graphical user interface for controlling one or more functions of the apparatus.

The apparatus can further comprise a vaporizer component that can comprise a heating element for vaporizing the one or more vaporizable materials, a vibrating mesh for nebulizing the mixed vaporizable material into a mist, an atomizer for atomizing the mixed vaporizable material into an aerosol, or an ultrasonic nebulizer for nebulizing the mixed vaporizable material into a mist.

In an aspect, a method 2000 comprising receiving an emission from a pharmaceutical at 2010, exposing the emission to a sensor at 2020, collecting data from the sensor regarding one or more constituents in the emission at 2030, analyzing the data to determine an analysis result at 2040, and displaying the analysis result at 2050. The emission can comprise a particle, a smoke, a vapor, a fluid, or a gas.

The method 2000 can further comprise causing the pharmaceutical to create the emission. Causing the pharmaceutical to create the emission can comprise one or more of, vaporizing the pharmaceutical, heating the pharmaceutical, cooling the pharmaceutical, or mechanically altering the pharmaceutical. Causing the pharmaceutical to create the emission can comprise decarboxylating at least a portion of the pharmaceutical.

The sensor can comprise at least one of a gas chromatograph, a mass spectrometer, an electrochemical detector, a pH sensor, a genetic sensor, a carbon nanotube detector, an infrared absorption sensor, an optical image sensor, a particle or cell detector, a semiconductor electrochemical sensor, or a temperature sensor.

The sensor is configured to detect one or more of, an identity of the one or more constituents, a type of the one or more constituents, a mixture of the one or more constituents, a temperature, a color, a concentration, a quantity, a toxicity, a pH, a vapor density, or a particle size.

Analyzing the data to determine an analysis result can comprise determining a molecular structure of the pharmaceutical. The analysis result can comprise a determination of a purity of the pharmaceutical. The analysis result can comprise a determination of an identity of an impurity of the pharmaceutical. The impurity of the pharmaceutical can comprise at least one of: lead, feces, fillers, cellulose, pathogens, placebo ingredients, and sugars. The impurity of the pharmaceutical can comprise a proper molecular element of the pharmaceutical in an unbalanced molecular form. Analyzing the data to determine an analysis result can comprise determining a quantity of the impurity. Analyzing the data to determine an analysis result can comprise comparing the quantity of the impurity to a stored impurity threshold and displaying a warning in response to the quantity of the impurity exceeding the stored impurity threshold. Analyzing the data to determine an analysis result can comprise determining a chemical signature of the emission based on the data and comparing the chemical signature to a database of chemical signatures.

The method 2000 can further comprise storing the chemical signature in the database as a new signature if the chemical signature is not found in the database of chemical signatures.

The method 2000 can further comprise transmitting the data to a computing device and receiving the analysis result from the computing device.

In view of the exemplary systems described supra, methodologies that can be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks can be required to implement the methodologies described herein. Additionally, it should be further appreciated that the methodologies disclosed herein are capable of being stored on an article of manufacture to facilitate transporting and transferring such methodologies to computers.

Those of skill would further appreciate that the various illustrative logical blocks, modules, circuits, and algorithm steps described in connection with the aspects disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component," "module," "system," and the like are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components may reside within a process and/or thread of execution and a component can be localized on one computer and/or distributed between two or more computers.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, an "aerosol" has the same meaning as "vapor," except for requiring the presence of at least one of particles or droplets. A substantial fraction means 10% or greater; however, it should be appreciated that higher fractions of small (<3 micron) particles or droplets can be desirable, up to and including 100%. It should further be appreciated that, to simulate smoke, average particle or droplet size can be less than three microns, for example, can be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

Various aspects presented in terms of systems can comprise a number of components, modules, and the like. It is to be understood and appreciated that the various systems may include additional components, modules, etc. and/or may not include all of the components, modules, etc. discussed in connection with the figures. A combination of these approaches can also be used.

In addition, the various illustrative logical blocks, modules, and circuits described in connection with certain aspects disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein can be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor can read information from, and write information to, the storage medium. In the alternative, the storage medium can be integral to the processor. The processor and the storage medium may reside in an ASIC or may reside as discrete components in another device.

Furthermore, the one or more versions can be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Those skilled in the art will recognize many modifications can be made to this configuration without departing from the scope of the disclosed aspects.

The previous description of the disclosed aspects is provided to enable any person skilled in the art to make or use the present disclosure. Various modifications to these aspects will be readily apparent to those skilled in the art, and the generic principles defined herein can be applied to other embodiments without departing from the spirit or scope of the disclosure. Thus; the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. A pharmaceutical analysis device comprising:
   a device processor operable for controlling the pharmaceutical analysis device;
   at least one intake configured to receive at least a portion of at least one emission generated from a pharmaceutical composition;
   at least one sensing component operatively coupled to the device processor and controlled in part by the device processor, wherein the at least one sensing component is configured to be in contact with at least a portion of the at least one emission generated from the pharmaceutical composition, wherein the at least one sensing component is operable to detect a plurality of constituent data associated with at least one constituent present in the at least one emission generated from the pharmaceutical composition;
   a memory operatively coupled to the device processor, wherein the memory is operable to store a plurality of standard pharmaceutical composition parameters, wherein the standard pharmaceutical composition parameters include at least one of a presence of at least one specified constituent in the pharmaceutical composition, a specified amount of at least one constituent in the pharmaceutical composition, an absence of at least one constituent in the pharmaceutical composition, a specified ratio between a plurality of specified constituents in the pharmaceutical composition, and combinations thereof; and
   at least one power source operatively coupled to the device processor and operable to generate a supply of power for the operation of the pharmaceutical analysis device;
   wherein the device processor is further operable to,
      receive at least a portion of the plurality of detected constituent data from the at least one sensing component,
      compare at least a portion of the plurality of detected constituent data for the at least one emission generated by the pharmaceutical composition to at least a portion of the plurality of standard pharmaceutical composition parameters and generate a plurality of comparison data therefrom,
      determine, based on at least a portion of the plurality of comparison data, whether the pharmaceutical composition is in accordance with at least one of the plurality of standard pharmaceutical composition parameters, and
      determine, based on at least a portion of at least one of the plurality of comparison data and the plurality of detected constituent data, the purity of the pharmaceutical composition.

2. The pharmaceutical analysis device of claim 1, wherein the device processor is further operable to determine, based on at least a portion of the plurality of detected constituent data, at least one emission quality, and generate a plurality of emission quality data therefrom.

3. The pharmaceutical analysis device of claim 2, wherein the at least one emission generated from the pharmaceutical composition comprises at least one of a vapor, a smoke, a gas, a fluid, and combinations thereof.

4. The pharmaceutical analysis device of claim 2, further comprising a sample chamber configured to receive the pharmaceutical composition therein, wherein the sample chamber is operable to subject the pharmaceutical composition to at least one test condition for a predetermined period of time so as to generate at least one emission therefrom, wherein the sample chamber is in fluid communication with the at least one intake for providing the at least one generated emission thereto.

5. The pharmaceutical analysis device of claim 4, wherein the at least one test condition to which the pharmaceutical composition is subjected comprises at least one of vaporizing at least a portion of the pharmaceutical composition, increasing the temperature of the pharmaceutical composition, decreasing the temperature of the pharmaceutical composition, changing a chemical composition of the pharmaceutical composition, altering a mechanical property of the pharmaceutical composition, and combinations thereof.

6. The pharmaceutical analysis device of claim 2, wherein the at least one sensing component is selected from the group of sensing components consisting of: a biochemical/chemical sensor, a genetic sensor, a thermal sensor, a radiation sensor, a mechanical sensor, an optical sensor, a magnetic sensor, an electrical sensor, and combinations thereof.

7. The pharmaceutical analysis device of claim 6, wherein the at least one sensing component is operable to detect at least one of an identification of a constituent in the at least one emission, an amount of a constituent in the at least one emission, a temperature of the at least one emission, a color of the at least one emission, a concentration of the at least one emission, an emission pH, an emission density, a particle size of a constituent in the at least one emission, a toxicity level of the at least one emission, and combinations thereof.

8. The pharmaceutical analysis device of claim 2, wherein the device processor is further operable to determine, based on at least a portion of at least one of the plurality of comparison data and the plurality of detected constituent data, whether the pharmaceutical composition comprises an impurity.

9. The pharmaceutical analysis device of claim 2, further comprising a display operatively coupled to the device processor, wherein the display is operable to display at least a portion of at least one of the plurality of comparison data and the plurality of emission quality data.

10. The pharmaceutical analysis device of claim 2, further comprising an input/output device operatively coupled to the device processor and controlled in part by the device processor, wherein the input/output device is operable to transmit at least a portion of at least one of the plurality of comparison data and the plurality of emission quality data to a remote device for processing thereof.

11. A method for analyzing at least one emission generated from a pharmaceutical composition by a pharmaceutical analysis device, wherein the pharmaceutical analysis device comprises (a) a device processor operable for controlling the pharmaceutical analysis device, (b) at least one intake configured to receive emissions generated from the pharmaceutical composition, (c) at least one sensing component operable to detect a plurality of constituent data associated with at least one constituent present in emissions generated from the pharmaceutical composition, and (d) a memory operable to store a plurality of standard pharmaceutical composition parameters, wherein the standard pharmaceutical composition parameters include at least one of a presence of at least one specified constituent in the pharmaceutical composition, a specified amount of at least one constituent in the pharmaceutical composition, an absence of at least one constituent in the pharmaceutical composition, a specified ratio between a plurality of specified constituents in the pharmaceutical composition, and combinations thereof, the method comprising:
receiving, via the at least one air intake, at least one emission generated from the pharmaceutical composition;
detecting, by the at least one sensing component, a plurality of constituent data associated with at least one constituent present in the at least one emission generated from the pharmaceutical composition;
comparing, by the device processor, at least a portion of the plurality of detected constituent data for the at least one emission generated by the pharmaceutical composition to at least a portion of the plurality of standard pharmaceutical composition parameters and generating a plurality of comparison data therefrom;
determining, by the device processor, based on at least a portion of the plurality of comparison data, whether the pharmaceutical composition is in accordance with at least one of the plurality of standard pharmaceutical composition parameter; and
determining, by the device processor, based on at least a portion of at least one of the plurality of comparison data and the plurality of detected constituent data, the purity of the pharmaceutical composition.

12. The method of claim 11, further comprising:
determining, by the device processor, at least one emission quality based on at least a portion of the plurality of detected constituent data;
generating, by the device processor, a plurality of emission quality data therefrom; and
displaying, via an associated display, at least a portion of at least one of the plurality of comparison data and the plurality of emission quality data.

13. The method of claim 12, further comprising transmitting, via an associated input/output device, at least a portion of at least one of the plurality of comparison data and the plurality of emission quality data to a remote device for processing thereof.

14. The method of claim 11, wherein the at least one emission generated from the pharmaceutical composition comprises at least one of a vapor, a smoke, a gas, a fluid, and combinations thereof.

15. The method of claim 11, further comprising subjecting the pharmaceutical composition to at least one test condition for a predetermined period of time so as to generate at least one emission therefrom and providing the at least one emission to the at least one intake.

16. The method of claim 15, wherein the at least one test condition to which the pharmaceutical composition is subjected comprises at least one of vaporizing at least a portion of the pharmaceutical composition, increasing the temperature of the pharmaceutical composition, decreasing the temperature of the pharmaceutical composition, changing a chemical composition of the pharmaceutical composition, altering a mechanical property of the pharmaceutical composition, and combinations thereof.

17. The method of claim 11, wherein the detecting a plurality of constituent data comprises detecting at least one of an identification of a constituent in the at least one emission, an amount of a constituent in the at least one emission, a temperature of the at least one emission, a color of the at least one emission, a concentration of the at least one emission, an emission pH, an emission density, a particle size of a constituent in the at least one emission, a toxicity level of the at least one emission, and combinations thereof.

18. The method of claim 11, further comprising determining, by the device processor, based on at least a portion of at least one of the plurality of comparison data and the plurality of detected constituent data, whether the pharmaceutical composition comprises an impurity.

* * * * *